United States Patent
Gaines et al.

(10) Patent No.: US 12,252,697 B2
(45) Date of Patent: Mar. 18, 2025

(54) HERBICIDE TOLERANT PLANTS AND PRODUCTION AND DETECTION OF SAME

(71) Applicants: Colorado State University Research Foundation, Fort Collins, CO (US); University of Adelaide, Adelaide (AU)

(72) Inventors: Todd Gaines, Fort Collins, CO (US); Marcelo Rodrigues Alves De Figueiredo, Fort Collins, CO (US); Anita Küpper, Fort Collins, CO (US); Christopher Preston, Fort Collins, CO (US)

(73) Assignees: Colorado State University Research Foundation, Fort Collins, CO (US); University of Adelaide, Adelaide (AU)

( * ) Notice: Subject to any disclaimer, the term of this patent is extended or adjusted under 35 U.S.C. 154(b) by 437 days.

(21) Appl. No.: 17/310,994

(22) PCT Filed: Mar. 11, 2020

(86) PCT No.: PCT/US2020/022118
§ 371 (c)(1),
(2) Date: Sep. 3, 2021

(87) PCT Pub. No.: WO2020/185907
PCT Pub. Date: Sep. 17, 2020

(65) Prior Publication Data
US 2022/0127633 A1   Apr. 28, 2022

Related U.S. Application Data

(60) Provisional application No. 62/963,630, filed on Jan. 21, 2020, provisional application No. 62/816,773, filed on Mar. 11, 2019.

(51) Int. Cl.
*C12N 15/82* (2006.01)
*C07K 14/415* (2006.01)
*C12Q 1/6895* (2018.01)

(52) U.S. Cl.
CPC ........ *C12N 15/8274* (2013.01); *C07K 14/415* (2013.01); *C12Q 1/6895* (2013.01)

(58) Field of Classification Search
None
See application file for complete search history.

(56) References Cited

U.S. PATENT DOCUMENTS

| 2004/0216190 A1 | 10/2004 | Kovalic |
| 2009/0144847 A1 | 6/2009 | Shaikh et al. |
| 2015/0082478 A1 | 3/2015 | Cigan et al. |

FOREIGN PATENT DOCUMENTS

WO   WO-2018191663 A1 * 10/2018 ........... C07K 14/415

OTHER PUBLICATIONS

Lavy et al (2016) Constitutive auxin response in Physcomitrella reveals complex interactions between Aux/IAA and ARF proteins eLife 5:e13325 (Year: 2016).*
LeClere 2018 (PNAS 115:13 p. E2911-E2920) (Year: 2018).*
Preston et al 2015 (Pest Management 71: p. 1523-1528) (Year: 2015).*
Figueiredo et al 2022 (PNAS 119:9, p. 1-9) (Year: 2022).*
International Searching Authority in connection with PCT/US20/22118 filed Mar. 11, 2020, "The International Search Report and The Written Opinion of the International Searching Authority, or the Declaration", 31 pages, mailed Aug. 7, 2020.
LeClere et al., "Cross-resistance to dicamba, 2,4-D, and fluroxypyr in Kochia scoparia is endowed by a mutation in an AUX/IAA gene", PNAS, vol. 115, No. 13, pp. E2911-E2920, 2018.

* cited by examiner

Primary Examiner — Matthew R Keogh
(74) Attorney, Agent, or Firm — McKee, Voorhees & Sease, PLC

(57) ABSTRACT

The present invention refers to a plant or plant part comprising a polynucleotide encoding an herbicide tolerant IAA2 polypeptide having a deleted or disrupted degron tail region, the expression of said polynucleotide confers to the plant or plant part tolerance to synthetic auxin herbicides, such as 2,4-D. The present invention relates to methods and plants and that have a deleted or disrupted degron tail region of the IAA2 protein obtained by gene editing, transformation, mutagenesis, breeding, and the like.

7 Claims, 13 Drawing Sheets
Specification includes a Sequence Listing.

MAYEKVNELNLKDTELRLGLPGTEQVKEEQEVSCVRSNKRQFQIDNEENREEEES
TPPTKTQIVGWPPVRSYRKNNNSVSYVKVSMDGAPYLRKIDLKTYKNYPELLKAL
ENMFKFTVGEYCEREGYKGSEVVPTYEDKDGDWMLVGDVPWDMFSSSCKRLRIMK
GSDDSSL

*FIG.1*

| | | |
|---|---|---|
| KFK39590.1 | ---------------------------------------------------------- | 0 |
| VVA98621.1 | ---------------------------------------------------------- | 0 |
| XP_002865542.1 | ---------------------------------------------------------- | 0 |
| ADL70486.1 | ---------------------------------------------------------- | 0 |
| ADC29363.1 | ---------------------------------------------------------- | 0 |
| NP_188943.1 | ---------------------------------------------------------- | 0 |
| NP_001326722.1 | MGGLKLRVPLLSPCLFLAFHASDNTSLSSFNPNEDAP--LYISLSPFLQNSSTSSPRTR? | 58 |
| ADL70491.1 | ---------------------------------------------------------- | 0 |
| AAB97164.1 | ---------------------------------------------------------- | 0 |
| XP_006298679.1 | ---------------------------------------------------------- | 0 |
| XP_010466600.1 | ---------------------------------------------------------- | 0 |
| XP_018486538.1 | ---------------------------------------------------------- | 0 |
| XP_018486510.1 | ---------------------------------------------------------- | 0 |
| XP_018486509.1 | ---------------------------------------------------------- | 0 |
| VDD45187.1 | MGGHSVCVLPLSPCLILAFHAPDNFYLSSFKPNFYASSPTFIYLSPISSKSIINQTHQQE | 60 |
| XP_013638497.1 | ---------------------------------------------------------- | 0 |
| XP_023562911.1 | MGGHSVCVLPLSPCLILAFHAPDNFYLSSFKPNFYASSPTFIYLSPISSKSIINQTHQQE | 60 |
| CDY10692.1 | ---------------------------------------------------------- | 0 |
| VDC71733.1 | MGGHSVCVLPLSPCLILAFDAPDNFYLSSFKPNFYASSPTFIYLSPISSKSIINQTHQQE | 60 |
| XP_009145242.1 | ---------------------------------------------------------- | 0 |
| XP_022575253.1 | MGGHSVCVLPLSPCLILAFDAPDNFYLSSFKPNFYASSPTFIYLSPISSKSIINQTHQQE | 60 |
| RID71991.1 | ---------------------------------------------------------- | 0 |
| XP_013625564.1 | MDGQSVYVFPLSPCLILASHAPDNFYLSSFYPNFYASSPTFIYLSPLFSSSTKLTMKKNH | 60 |
| VDC94217.1 | ---------------------------------------------------------- | 0 |
| XP_022572324.1 | -------MLPTTSLSL-------PLHLT-------SMHL-LPPVYISLSLKPIINQ----?-H | 36 |
| XP_018434635.1 | ---------------------------------------------------------- | 0 |
| XP_013636218.1 | ---------------------------------------------------------- | 0 |
| XP_013751214.1 | ---------------------------------------------------------- | 0 |
| XP_013643498.1 | MGGHSVCVPPLSPCLFLAFHAPDNISLSSFRPNFYASSPSCIYLSFSKPIINQ----?-H | 55 |
| CDY40837.1 | ---------------------------------------------------------- | 0 |
| XP_013751366.1 | ---------------------------------------------------------- | 0 |
| XP_009108345.1 | ---------------------------------------------------------- | 0 |
| XP_006406101.1 | ---------------------------------------------------------- | 0 |
| IAA2_full_protein_S | ---------------------------------------------------------- | 0 |
| IAA2_deletion_protein_R | ---------------------------------------------------------- | 0 |

FIG. 2A

| | | | |
|---|---|---|---|
| KFK39590.1 | ---------------------------- | ------------MAY-EKVNELNLKDTELRLGLPGTEEE | 26 |
| VVA98621.1 | ---------------------------- | ------------MAY-EKVNELNLKDTELRLGLPGTEQE | 26 |
| XP_002865542.1 | ---------------------------- | ------------MAY-EKVNELNLKDTELRLGLPGTEQE | 26 |
| ADL70485.1 | ---------------------------- | ------------MAY-EKVNELNLKDTELCLGLPGRTEE | 26 |
| ADC29363.1 | ---------------------------- | ------------MAY-EKVNELNLKDTELCLGLPGRTEK | 26 |
| NP_186943.1 | ---------------------------- | ------------MAY-EKVNELNLKDTELCLGLPGRTEK | 26 |
| NP_001326722.1 | RRRTRQE-EQ-STQ-ENTQEG-NTKIDIDPKAMAY-EKVNELNLKDTELCLGLPGRTEK | 113 |
| ADL70491.1 | ---------------------------- | ------------MAY-EKVNELNLKDTELCLGLPGRTEK | 26 |
| AAB97164.1 | ---------------------------- | ------------MAY-EKVNELNLKDTELCLGLPGRTEK | 26 |
| XP_006298679.1 | ---------------------------- | ------------MAY-EKVNELNLKDTELCLGLPGRTEE | 26 |
| XP_010466600.1 | ---------------------------- | ------------MAYEKRVNELNLKDTELCLGLPGRTEE | 27 |
| XP_018486538.1 | ---------------------------- | ------------MAY-EKVNELNLKDTELRLGLPGTE-K | 25 |
| XP_018486510.1 | ---------------------------- | ------------MAY-EKVNELNLKDTELRLGLPGTE-Q | 25 |
| XP_018486509.1 | ---------------------------- | ------------MAY-EKVNELNLKDTELRLGLPGTE-Q | 25 |
| VDD45187.1 | QYQEQEQEQEKDF--------------- | ------AERNLDFEKKMAY-EKVNELNLKDTELRLGLPGTG-Q | 108 |
| XP_013638497.1 | ---------------------------- | ------------MAY-EKVNELNLKDTELRLGLPGTG-Q | 25 |
| XP_022552911.1 | QYQEQEQEQEKDF--------------- | ------A--NLDFEKKMAY-EKVNELNLKDTELRLGLPGTG-Q | 106 |
| CDY10692.1 | ---------------------------- | ------------MAY-EKVNELNLKDTELRLGLPGTG-Q | 25 |
| VDC71733.1 | QYQEQEQEQEKDS--------------- | ------AERNLDCEKKMAY-EKVNELNLKDTELRLGLPGTG-Q | 108 |
| XP_009145242.1 | ---------------------------- | ------------MAY-EKVNELNLKDTELRLGLPGTG-Q | 25 |
| XP_022575253.1 | QYQEQEQEQEKDS--------------- | ------ANLDCEKKMAY-EKVNELNLKDTELRLGLPGTG-Q | 106 |
| RID71991.1 | ---------------------------- | ------------MTY-EKVNELNLKDTELRLGLPGTE-Q | 25 |
| XP_013625564.1 | --NKNKREILQHFSQKKTTQEHREIMFLILKKTMTY-ERVNELNLKDTELRLGLPGTE-Q | 116 |
| VDC94217.1 | ---------------------------- | ------------MTY-EKVNELNLKDTELRLGLPGTE-Q | 25 |
| XP_022572324.1 | ---QQEQEEQGFCFGNATKTY-RERL-LDLERKMAY-EKVNELNLKDTELRLGLPGTE-Q | 89 |
| XP_018434635.1 | ---------------------------- | ------------MAY-EKVNELNLKDTELRLGLPGTE-Q | 25 |
| XP_013636218.1 | ---------------------------- | ------------MAY-EKVNELNLKDTELRLGLPGTE-Q | 25 |
| XP_013751214.1 | ----KQEQEEEQGFCFGYITQRHIERGV-LILKKMAY-ERVNELNLKDTELRLGLPGIE-Q | 109 |
| XP_013643498.1 | ---------------------------- | ------------MAY-EKVNELNLKDTELRLGLPGIE-Q | 25 |
| CDY40837.1 | ---------------------------- | ------------MAY-EKVNELNLKDTELRLGLPGIE-Q | 25 |
| XP_013751366.1 | ---------------------------- | ------------MAY-EKVNELNLKDTELRLGLPGTE-Q | 25 |
| XP_009108345.1 | ---------------------------- | ------------MAY-EKVNELNLKDTELRLGLPGTD-E | 25 |
| XP_006406101.1 | ---------------------------- | ------------MAY-EKVNELNLKDTELRLGLPGTE-Q | 25 |
| IAA2_full_protein_S | ---------------------------- | ------------MAY-EKVNELNLKDTELRLGLPGTE-Q | 25 |
| IAA2_deletion_protein_R | ---------------------------- | ------------ | : |

| ID | Sequence | Pos |
|---|---|---|
| KFK39590.1 | FVPTYEDKDGDWMLVGDVPWDMFSSSCKRLRIMKGSDAPALDSSL- | 174 |
| VVA98621.1 | FVPTYEDKDGDWMLVGDVPWDMFSSSCKRLRIMKGSDAPALDSSL- | 177 |
| XP_002865542.1 | FVPTYEDKDGDWMLVGDVPWDMFSSSCKRLRIMKGSDAPALDSSL- | 174 |
| ADL70486.1 | FVPTYEDKDGDWMLVGDVPWDMFSSSCKRLRIMKGSDAPALDSSL- | 174 |
| ADC29363.1 | FVPTYEDKDGDWMLVGDVPWDMFSSSCKRLRIMKGSDAPALDSSL- | 174 |
| NP_186943.1 | FVPTYEDKDGDWMLVGDVPWDMFSSSCKRLRIMKGSDAPALDSSL- | 174 |
| NP_001326722.1 | FVPTYEDKDGDWMLVGDVPWDMFSSSCKRLRIMKGSDAPALDSSL- | 261 |
| ADL70491.1 | FVPTYEDKDGDWMLVGDVPWDMFSSSCKRLRIMKGSDAPALDSSL- | 174 |
| AAB97164.1 | FVPTYEDKDGDWMLVGDVPWDMFSSSCKRLRIMKGSDAPALDSSSL | 174 |
| XP_006298679.1 | FVPTYEDKDGDWMLVGDVPWDMFSSSCKRLRIMKGSDAPTLDASL- | 174 |
| XP_010466600.1 | FVPTYEDKDGDWMLVGDVPWDMFSSSCKRLRIMKGSDAPTLDASL- | 174 |
| XP_018486538.1 | VVPTYEDKDGDWMLVGDVPWDMFSSSCKRLRIMKGPDALALDSGL- | 171 |
| XP_018486510.1 | VVPTYEDKDGDWMLVGDVPWDMFSSSCKRLRIMKGSDALALDSAL- | 175 |
| XP_018486509.1 | VVPTYEDKDGDWMLVGDVPWDMFSSSCKRLRIMKGSDALALDSAL- | 185 |
| VDD45187.1 | VVPTYEDKDGDWMLVGDVPWDMFSSSCKRLRIMKGSDALALDSAL- | 255 |
| XP_013638497.1 | VVPTYEDKDGDWMLVGDVPWDMFSSSCKRLRIMKGSDALALDSAL- | 172 |
| XP_022552911.1 | VVPTYEDKDGDWMLVGDVPWDMFSSSCKRLRIMKGSDALALDSAL- | 253 |
| CDY10692.1 | VVPTYEDKDGDWMLVGDVPWDMFSSSCKRLRIMKGSDALALDSAL- | 172 |
| VDC71733.1 | VVPTYEDKDGDWMLVGDVPWDMFSSSCKRLRIMKGSDALALDSAL- | 255 |
| XP_009145242.1 | VVPTYEDKDGDWMLVGDVPWDMFSSSCKRLRIMKGSDALALDSAL- | 172 |
| XP_022575253.1 | VVPTYEDKDGDWMLVGDVPWDMFSSSCKRLRIMKGSDALALDSAL- | 253 |
| RID71991.1 | VLPTYEDKDGDWMLVGDVPWDMFSSSCKRLRIMKGSDALVLDSAL- | 171 |
| XP_013625564.1 | VIPTYEDKDGDWMLVGDVPWDMFSSSCKRLRIMKGSDALALDSAL- | 171 |
| VDC94217.1 | VIPTYEDKDGDWMLVGDVPWDMFSSSCKRLRIMKGSDALALDSAL- | 262 |
| XP_022572324.1 | VIPTYEDKDGDWMLVGDVPWDMFSSSCKRLRIMKGSDALALDSAL- | 171 |
| XP_018434635.1 | VVPTYEDKDGDWMLVGDVPWDMFSSSCKRLRIMKGSDALALDSALL | 236 |
| XP_013636218.1 | VVPTYEDKDGDWMLVGDVPWDMFSSSCKRLRIMKGSDALALDSAL- | 171 |
| XP_013751214.1 | VVPTYEDKDGDWMLVGDVPWDMFSSSCKRLRIMKGSDALALDSAL- | 171 |
| XP_013643498.1 | VVPTYEDKDGDWMLVGDVPWDMFSSSCKRLRIMKGSDALALDSAL- | 255 |
| CDY40837.1 | VVPTYEDKDGDWMLVGDVPWDMFSSSCKRLRIMKGSDALALDSAL- | 171 |
| XP_013751366.1 | VVPTYEDKDGDWMLVGDVPWDMFSSSCKRLRIMKGSDALALDSAL- | 171 |
| XP_009103345.1 | VVPTYEDKDGDWMFVGDVPWDMFSSSCKRLRIMKGSDALALDSAL- | 173 |
| XP_006406101.1 | VVPTYEDKDGDVFWDMFVGDVPWDMFSSSCKRLRIMKGSDADSSL---- | 172 |
| IAA2_full_protein_S | VVPTYEDKDGDWMLVGDVPWDMFSSSCKRLRIMKGSDDSSL----- | 163 |
| IAA2_deletion_protein_R | .:************************************ | |

| Fold change | Gene | Function |
|---|---|---|
| ↓ 0.1 | PRP39-2 | Tetratricopeptide repeat (TPR)-like superfamily protein |
| ↓ 0.3 | AUX/IAA2 | Auxin-responsive protein |
| ↓ 0.5 | SNARE-like protein | Involved in vacuolar sorting and storage |
| ↑ 5.7 | Glycoprotein ABCB13 | Cellular auxin efflux-transporter |

SEQUENCE LISTING

<160> NUMBER OF SEQ ID NOS: 75

<210> SEQ ID NO 1
<211> LENGTH: 172
<212> TYPE: PRT
<213> ORGANISM: Sisymbrium orientale

<400> SEQUENCE: 1

```
Met Ala Tyr Glu Lys Val Asn Glu Leu Asn Leu Lys Asp Thr Glu Leu
1               5                   10                  15

Arg Leu Gly Leu Pro Gly Thr Glu Gln Val Lys Glu Glu Gln Glu Val
            20                  25                  30

Ser Cys Val Arg Ser Asn Lys Arg Gln Phe Gln Ile Asp Asn Glu Glu
        35                  40                  45

Asn Arg Glu Glu Glu Ser Thr Pro Pro Thr Lys Thr Gln Ile Val
    50                  55                  60

Gly Trp Pro Pro Val Arg Ser Tyr Arg Lys Asn Asn Asn Ser Val Ser
65                  70                  75                  80

Tyr Val Lys Val Ser Met Asp Gly Ala Pro Tyr Leu Arg Lys Ile Asp
                85                  90                  95

Leu Lys Thr Tyr Lys Asn Tyr Pro Glu Leu Leu Lys Ala Leu Glu Asn
            100                 105                 110

Met Phe Lys Phe Thr Val Gly Glu Tyr Cys Glu Arg Glu Gly Tyr Lys
        115                 120                 125

Gly Ser Glu Val Val Pro Thr Tyr Glu Asp Lys Asp Gly Asp Trp Met
    130                 135                 140

Leu Val Gly Asp Val Pro Trp Asp Met Phe Ser Ser Ser Cys Lys Arg
145                 150                 155                 160

Leu Arg Ile Met Lys Gly Ser Asp Asp Ser Ser Leu
                165                 170
```

<210> SEQ ID NO 2
<211> LENGTH: 519
<212> TYPE: DNA
<213> ORGANISM: Sisymbrium orientale

<400> SEQUENCE: 2

```
atggcgtacg agaaagtcaa tgagcttaac cttaaggaca cagagcttcg tcttggatta      60
cctggaacag agcaagttaa agaagaacaa gaggtttctt gcgttagaag caacaagcgt     120
caattccaaa tcgataacga ggaaaaccgt gaggaagaag aatctacacc tcctacgaaa     180
actcaaatcg ttggttggcc tccggtgaga tcttaccgta agaacaacaa cagtgtgagc     240
tatgtgaaag tgagtatgga cggagcacca tacctccgca aaatcgatct caaaacatac     300
aaaaactatc cagagcttct caaggcgtta gaaaacatgt tcaagttcac ggtaggtgag     360
tactgtgaaa gagaaggata caaaggatct gaagtcgtac aacgtacga ggataaagat      420 ggagactgga tgttggttgg tgatgttcca tgggatatgt tctcatcctc ttgtaagaga     480
```

```
ctcagaatca tgaaaggatc tgatgactct tccttatga                    519
```

<210> SEQ ID NO 3
<211> LENGTH: 163
<212> TYPE: PRT
<213> ORGANISM: Sisymbrium orientale

<400> SEQUENCE: 3

```
Met Ala Tyr Glu Lys Val Asn Glu Leu Asn Leu Lys Asp Thr Glu Leu
1               5                   10                  15

Arg Leu Gly Leu Pro Gly Thr Glu Gln Val Lys Glu Gln Glu Val
            20                  25                  30

Ser Cys Val Arg Ser Asn Lys Arg Gln Phe Gln Ile Asp Asn Glu Glu
        35                  40                  45

Asn Arg Glu Glu Glu Ser Thr Pro Pro Thr Lys Thr Gln Ile Val
    50                  55                  60

Gly Trp Pro Pro Val Arg Ser Tyr Val Lys Val Ser Met Asp Gly Ala
65                  70                  75                  80

Pro Tyr Leu Arg Lys Ile Asp Leu Lys Thr Tyr Lys Asn Tyr Pro Glu
                85                  90                  95

Leu Leu Lys Ala Leu Glu Asn Met Phe Lys Phe Thr Val Gly Glu Tyr
            100                 105                 110

Cys Glu Arg Glu Gly Tyr Lys Gly Ser Glu Val Val Pro Thr Tyr Glu
        115                 120                 125

Asp Lys Asp Gly Asp Trp Met Leu Val Gly Asp Val Pro Trp Asp Met
    130                 135                 140

Phe Ser Ser Ser Cys Lys Arg Leu Arg Ile Met Lys Gly Ser Asp Asp
145                 150                 155                 160

Ser Ser Leu
```

<210> SEQ ID NO 4
<211> LENGTH: 492
<212> TYPE: DNA
<213> ORGANISM: Sisymbrium orientale

<400> SEQUENCE: 4

```
atggcgtacg agaaagtcaa tgagcttaac cttaaggaca cagagcttcg tcttggatta     60
cctggaacag agcaagttaa agaagaacaa gaggtttctt gcgttagaag caacaagcgt    120
caattccaaa tcgataacga ggaaaaccgt gaggaagaag aatctacacc tcctacgaaa    180
actcaaatcg ttggttggcc tccggtgaga tcttatgtga aagtgagtat ggacggagca    240
ccatacctcc gcaaaatcga tctcaaaaca tacaaaaact atccagagct tctcaaggcg    300
ttagaaaaca tgttcaagtt cacggtaggt gagtactgtg aaagagaagg atacaaagga    360
tctgaagtcg taccaacgta cgaggataaa gatggagact ggatgttggt tggtgatgtt    420
ccatgggata tgttctcatc ctcttgtaag agactcagaa tcatgaaagg atctgatgac    480
tcttccttat ga                                                        492
```

<210> SEQ ID NO 5
<211> LENGTH: 9
<212> TYPE: PRT
<213> ORGANISM: Sisymbrium orientale

<400> SEQUENCE: 5

```
Tyr Arg Lys Asn Asn Asn Ser Val Ser
1               5
```

<210> SEQ ID NO 6
<211> LENGTH: 174
<212> TYPE: PRT
<213> ORGANISM: Arabis alpina

<400> SEQUENCE: 6

Met Ala Tyr Glu Lys Val Asn Glu Leu Asn Leu Lys Asp Thr Glu Leu
1               5                   10                  15

Arg Leu Gly Leu Pro Gly Thr Glu Glu Val Lys Gln Glu Gln Glu
            20                  25                  30

Val Ser Cys Val Arg Ser Asn Lys Arg Gln Phe Asp Glu Glu Thr Arg
                35                  40                  45

Asp Glu Gln Glu Ser Met Pro Pro Thr Lys Thr Gln Ile Val Gly Trp
        50                  55                  60

Pro Pro Val Arg Ser Tyr Arg Lys Asn Asn Ser Val Ser Tyr Val
65                  70                  75                  80

Lys Val Ser Met Asp Gly Ala Pro Tyr Leu Arg Lys Ile Asp Leu Lys
                85                  90                  95

Thr Tyr Lys Asn Tyr Pro Glu Leu Leu Lys Ala Leu Glu Asn Met Phe
            100                 105                 110

Lys Phe Thr Ile Gly Glu Tyr Ser Glu Arg Glu Gly Tyr Lys Gly Ser
        115                 120                 125

Gly Phe Val Pro Thr Tyr Glu Asp Lys Asp Gly Asp Trp Met Leu Val
    130                 135                 140

Gly Asp Val Pro Trp Asp Met Phe Ser Ser Cys Lys Arg Leu Arg
145                 150                 155                 160

Ile Met Lys Gly Ser Glu Ala Pro Ala Leu Asp Ser Ser Leu
                165                 170

<210> SEQ ID NO 7
<211> LENGTH: 177
<212> TYPE: PRT
<213> ORGANISM: Arabis nemorensis

<400> SEQUENCE: 7

Met Ala Tyr Glu Lys Val Asn Glu Leu Asn Leu Lys Asp Thr Glu Leu
1               5                   10                  15

Arg Leu Gly Leu Pro Gly Thr Glu Gln Glu Val Lys Gln Glu Lys Glu
            20                  25                  30

Val Ser Cys Val Arg Ser Asn Lys Arg Gln Phe Asp Glu Glu Thr Leu
                35                  40                  45

Asn Glu Glu Glu Ser Met Pro Pro Thr Lys Thr Gln Ile Val Gly Trp
        50                  55                  60

Pro Pro Val Arg Ser Tyr Arg Lys Asn Asn Asn Asn Ser Val Ser
65                  70                  75                  80

Tyr Val Lys Val Ser Met Asp Gly Ala Pro Tyr Leu Arg Lys Ile Asp
                85                  90                  95

Leu Lys Thr Tyr Lys Asn Tyr Gln Glu Leu Leu Lys Ala Leu Glu Asn
            100                 105                 110

Met Phe Lys Phe Thr Ile Gly Glu Tyr Asn Glu Arg Glu Gly Tyr Lys
        115                 120                 125

Arg Gly Ser Gly Phe Val Pro Thr Tyr Glu Asp Lys Asp Gly Asp Trp
    130                 135                 140

Met Leu Val Gly Asp Val Pro Trp Asp Met Phe Ser Ser Cys Lys
145                 150                 155                 160

```
Arg Leu Arg Ile Met Lys Gly Ser Asp Ala Pro Ala Leu Asp Ser Ser
                165                 170                 175

Leu

<210> SEQ ID NO 8
<211> LENGTH: 174
<212> TYPE: PRT
<213> ORGANISM: Arabidopsis lyrata

<400> SEQUENCE: 8

Met Ala Tyr Glu Lys Val Asn Glu Leu Asn Leu Lys Asp Thr Glu Leu
1               5                   10                  15

Cys Leu Gly Leu Pro Gly Arg Thr Glu Glu Ile Lys Glu Glu Gln Glu
                20                  25                  30

Val Ser Cys Val Lys Ser Asn Asn Lys Arg Gln Phe Glu Asp Thr Arg
            35                  40                  45

Glu Glu Glu Glu Ser Thr Pro Pro Thr Lys Thr Gln Ile Val Gly Trp
    50                  55                  60

Pro Pro Val Arg Ser Ser Arg Lys Asn Asn Asn Ser Val Ser Tyr Val
65                  70                  75                  80

Lys Val Ser Met Asp Gly Ala Pro Tyr Leu Arg Lys Ile Asp Leu Lys
                85                  90                  95

Thr Tyr Lys Asn Tyr Pro Glu Leu Leu Lys Ala Leu Glu Asn Met Phe
            100                 105                 110

Lys Val Thr Ile Gly Glu Tyr Cys Glu Arg Glu Gly Tyr Lys Gly Ser
        115                 120                 125

Gly Phe Val Pro Thr Tyr Glu Asp Lys Asp Gly Asp Trp Met Leu Val
130                 135                 140

Gly Asp Val Pro Trp Asp Met Phe Ser Ser Ser Cys Lys Arg Leu Arg
145                 150                 155                 160

Ile Met Lys Gly Ser Asp Ala Pro Ala Leu Asp Ser Ser Leu
                165                 170

<210> SEQ ID NO 9
<211> LENGTH: 174
<212> TYPE: PRT
<213> ORGANISM: Arabidopsis thaliana

<400> SEQUENCE: 9

Met Ala Tyr Glu Lys Val Asn Glu Leu Asn Leu Lys Asp Thr Glu Leu
1               5                   10                  15

Cys Leu Gly Leu Pro Gly Arg Thr Glu Lys Ile Lys Glu Glu Gln Glu
                20                  25                  30

Val Ser Cys Val Lys Ser Asn Asn Lys Arg Leu Phe Glu Glu Thr Arg
            35                  40                  45

Asp Glu Glu Glu Ser Ile Pro Pro Thr Lys Thr Gln Ile Val Gly Trp
    50                  55                  60

Pro Pro Val Arg Ser Ser Arg Lys Asn Asn Ser Val Ser Tyr Val
65                  70                  75                  80

Lys Val Ser Met Asp Gly Ala Pro Tyr Leu Arg Lys Ile Asp Leu Lys
                85                  90                  95

Thr Tyr Lys Asn Tyr Pro Glu Leu Leu Lys Ala Leu Glu Asn Met Phe
            100                 105                 110

Lys Val Met Ile Gly Glu Tyr Cys Glu Arg Glu Gly Tyr Lys Gly Ser
        115                 120                 125

Gly Phe Val Pro Thr Tyr Glu Asp Lys Asp Gly Asp Trp Met Leu Val
```

```
                130                 135                 140
Gly Asp Val Pro Trp Asp Met Phe Ser Ser Cys Lys Arg Leu Arg
145                 150                 155                 160

Ile Met Lys Gly Ser Asp Ala Pro Ala Leu Asp Ser Ser Leu
                165                 170

<210> SEQ ID NO 10
<211> LENGTH: 174
<212> TYPE: PRT
<213> ORGANISM: Arabidopsis thaliana

<400> SEQUENCE: 10

Met Ala Tyr Glu Lys Val Asn Glu Leu Asn Leu Lys Asp Thr Glu Leu
1               5                   10                  15

Cys Leu Gly Leu Pro Gly Arg Thr Glu Lys Ile Lys Glu Glu Gln Glu
                20                  25                  30

Val Ser Cys Val Lys Ser Asn Asn Lys Arg Leu Phe Glu Glu Thr Arg
            35                  40                  45

Asp Glu Glu Glu Ser Thr Pro Pro Thr Lys Thr Gln Ile Val Gly Trp
        50                  55                  60

Pro Pro Val Arg Ser Ser Arg Lys Asn Asn Thr Ser Val Ser Tyr Val
65                  70                  75                  80

Lys Val Ser Met Asp Gly Ala Pro Tyr Leu Arg Lys Ile Asp Leu Lys
                85                  90                  95

Thr Tyr Lys Asn Tyr Pro Glu Leu Leu Lys Ala Leu Glu Asn Met Phe
                100                 105                 110

Lys Val Met Ile Gly Glu Tyr Cys Glu Arg Glu Gly Tyr Lys Gly Ser
                115                 120                 125

Gly Phe Val Pro Thr Tyr Glu Asp Lys Asp Gly Asp Trp Met Leu Val
            130                 135                 140

Gly Asp Val Pro Trp Asp Met Phe Ser Ser Cys Lys Arg Leu Arg
145                 150                 155                 160

Ile Met Lys Gly Ser Asp Ala Pro Ala Leu Asp Ser Ser Leu
                165                 170

<210> SEQ ID NO 11
<211> LENGTH: 174
<212> TYPE: PRT
<213> ORGANISM: Arabidopsis thaliana

<400> SEQUENCE: 11

Met Ala Tyr Glu Lys Val Asn Glu Leu Asn Leu Lys Asp Thr Glu Leu
1               5                   10                  15

Cys Leu Gly Leu Pro Gly Arg Thr Glu Lys Ile Lys Glu Glu Gln Glu
                20                  25                  30

Val Ser Cys Val Lys Ser Asn Asn Lys Arg Leu Phe Glu Glu Thr Arg
            35                  40                  45

Asp Glu Glu Glu Ser Thr Pro Pro Thr Lys Thr Gln Ile Val Gly Trp
        50                  55                  60

Pro Pro Val Arg Ser Ser Arg Lys Asn Asn Ser Val Ser Tyr Val
65                  70                  75                  80

Lys Val Ser Met Asp Gly Ala Pro Tyr Leu Arg Lys Ile Asp Leu Lys
                85                  90                  95

Thr Tyr Lys Asn Tyr Pro Glu Leu Leu Lys Ala Leu Glu Asn Met Phe
                100                 105                 110

Lys Val Met Ile Gly Glu Tyr Cys Glu Arg Glu Gly Tyr Lys Gly Ser
```

```
                    115                 120                 125
Gly Phe Val Pro Thr Tyr Glu Asp Lys Asp Gly Asp Trp Met Leu Val
                130                 135                 140

Gly Asp Val Pro Trp Asp Met Phe Ser Ser Cys Lys Arg Leu Arg
145                 150                 155                 160

Ile Met Lys Gly Ser Asp Ala Pro Ala Leu Asp Ser Ser Leu
                165                 170

<210> SEQ ID NO 12
<211> LENGTH: 261
<212> TYPE: PRT
<213> ORGANISM: Arabidopsis thaliana

<400> SEQUENCE: 12

Met Gly Gly Leu Lys Leu Arg Val Pro Leu Ser Pro Cys Leu Phe
1               5                   10                  15

Leu Ala Phe His Ala Ser Asp Asn Thr Ser Leu Ser Ser Phe Asn Pro
                20                  25                  30

Asn Phe Asp Ala Pro Leu Tyr Ile Ser Leu Ser Pro Phe Leu Gln Asn
            35                  40                  45

Ser Ser Thr Ser Ser Pro Arg Thr Arg Thr Arg Arg Arg Arg Thr Arg
50                  55                  60

Gln Glu Glu Gln Ser Thr Gln Glu Asn Thr Gln Glu Gly Asn Thr Lys
65                  70                  75                  80

Ile Asp Ile Asp Pro Lys Ala Met Ala Tyr Glu Lys Val Asn Glu Leu
                85                  90                  95

Asn Leu Lys Asp Thr Glu Leu Cys Leu Gly Leu Pro Gly Arg Thr Glu
                100                 105                 110

Lys Ile Lys Glu Glu Gln Glu Val Ser Cys Val Lys Ser Asn Asn Lys
            115                 120                 125

Arg Leu Phe Glu Glu Thr Arg Asp Glu Glu Glu Ser Thr Pro Pro Thr
130                 135                 140

Lys Thr Gln Ile Val Gly Trp Pro Pro Val Arg Ser Ser Arg Lys Asn
145                 150                 155                 160

Asn Asn Ser Val Ser Tyr Val Lys Val Ser Met Asp Gly Ala Pro Tyr
                165                 170                 175

Leu Arg Lys Ile Asp Leu Lys Thr Tyr Lys Asn Tyr Pro Glu Leu Leu
            180                 185                 190

Lys Ala Leu Glu Asn Met Phe Lys Val Met Ile Gly Glu Tyr Cys Glu
        195                 200                 205

Arg Glu Gly Tyr Lys Gly Ser Gly Phe Val Pro Thr Tyr Glu Asp Lys
    210                 215                 220

Asp Gly Asp Trp Met Leu Val Gly Asp Val Pro Trp Asp Met Phe Ser
225                 230                 235                 240

Ser Ser Cys Lys Arg Leu Arg Ile Met Lys Gly Ser Asp Ala Pro Ala
                245                 250                 255

Leu Asp Ser Ser Leu
            260

<210> SEQ ID NO 13
<211> LENGTH: 174
<212> TYPE: PRT
<213> ORGANISM: Arabidopsis thaliana
<220> FEATURE:
<221> NAME/KEY: misc_feature
<222> LOCATION: (38)..(38)
<223> OTHER INFORMATION: Xaa can be any naturally occurring amino acid
```

<400> SEQUENCE: 13

Met Ala Tyr Glu Lys Val Asn Glu Leu Asn Leu Lys Asp Thr Glu Leu
1               5                   10                  15

Cys Leu Gly Leu Pro Gly Arg Thr Glu Lys Ile Lys Glu Glu Gln Glu
            20                  25                  30

Val Ser Cys Val Lys Xaa Asn Asn Lys Arg Leu Phe Glu Glu Thr Arg
        35                  40                  45

Asp Glu Glu Ser Thr Pro Pro Thr Lys Thr Gln Ile Val Gly Trp
    50                  55                  60

Pro Pro Val Arg Ser Ser Arg Lys Asn Asn Ser Val Ser Tyr Val
65                  70                  75                  80

Lys Val Ser Met Asp Gly Ala Pro Tyr Leu Arg Lys Ile Asp Leu Lys
                85                  90                  95

Thr Tyr Lys Asn Tyr Pro Glu Leu Leu Lys Ala Leu Glu Asn Met Phe
            100                 105                 110

Lys Val Met Ile Gly Glu Tyr Cys Glu Arg Glu Gly Tyr Lys Gly Ser
            115                 120                 125

Gly Phe Val Pro Thr Tyr Glu Asp Lys Asp Gly Asp Trp Met Leu Val
130                 135                 140

Gly Asp Val Pro Trp Asp Met Phe Ser Ser Cys Lys Arg Leu Arg
145                 150                 155                 160

Ile Met Lys Gly Ser Asp Ala Pro Ala Leu Asp Ser Ser Leu
                165                 170

<210> SEQ ID NO 14
<211> LENGTH: 174
<212> TYPE: PRT
<213> ORGANISM: Arabidopsis thaliana

<400> SEQUENCE: 14

Met Ala Tyr Glu Lys Val Asn Glu Leu Asn Leu Lys Asp Thr Glu Leu
1               5                   10                  15

Cys Leu Gly Leu Pro Gly Arg Thr Glu Lys Ile Lys Glu Glu Gln Glu
            20                  25                  30

Val Ser Cys Val Lys Ile Asn Asn Lys Arg Leu Phe Glu Glu Thr Arg
        35                  40                  45

Asp Glu Glu Ser Thr Pro Pro Thr Lys Thr Gln Ile Val Gly Trp
    50                  55                  60

Pro Pro Val Arg Ser Ser Arg Lys Asn Asn Ser Val Ser Tyr Val
65                  70                  75                  80

Lys Val Ser Met Asp Gly Ala Pro Tyr Leu Arg Lys Ile Asp Leu Lys
                85                  90                  95

Thr Tyr Lys Asn Tyr Pro Glu Leu Leu Lys Ala Leu Glu Asn Met Phe
            100                 105                 110

Lys Val Met Ile Gly Glu Tyr Cys Glu Arg Glu Gly Tyr Lys Gly Ser
            115                 120                 125

Gly Phe Val Pro Thr Tyr Glu Asp Lys Asp Gly Asp Trp Met Leu Val
130                 135                 140

Gly Asp Val Pro Trp Asp Met Phe Ser Ser Cys Lys Arg Leu Arg
145                 150                 155                 160

Ile Met Lys Gly Ser Asp Ala Pro Ala Leu Asp Ser Ser Leu
                165                 170

<210> SEQ ID NO 15

```
<211> LENGTH: 174
<212> TYPE: PRT
<213> ORGANISM: Capsella rubella

<400> SEQUENCE: 15

Met Ala Tyr Glu Lys Val Asn Glu Leu Asn Leu Lys Asp Thr Glu Leu
1               5                   10                  15

Cys Leu Gly Leu Pro Gly Arg Thr Glu Glu Ile Lys Gln Glu Gln Glu
            20                  25                  30

Val Ser Cys Val Arg Ser Asn Asn Lys Arg Gln Phe Glu Glu Thr Leu
        35                  40                  45

Asp Asp Glu Glu Ser Thr Pro Pro Thr Lys Thr Gln Ile Val Gly Trp
    50                  55                  60

Pro Pro Val Arg Ser Tyr Arg Lys Asn Asn Ser Val Ser Tyr Val Lys
65                  70                  75                  80

Val Ser Met Asp Gly Ala Pro Tyr Leu Arg Lys Ile Asp Leu Lys Thr
                85                  90                  95

Tyr Lys Asn Tyr Pro Glu Leu Leu Lys Ala Leu Glu Asn Met Phe Lys
            100                 105                 110

Phe Thr Val Gly Glu Tyr Ser Glu Arg Glu Gly Tyr Lys Gly Ser Gly
        115                 120                 125

Phe Val Pro Thr Tyr Glu Asp Lys Asp Gly Asp Trp Met Leu Val Gly
    130                 135                 140

Asp Val Pro Trp Asp Met Phe Ser Ser Cys Lys Arg Leu Arg Ile
145                 150                 155                 160

Met Lys Gly Ser Asp Ala Pro Ala Leu Asp Ser Ser Ser Leu
            165                 170

<210> SEQ ID NO 16
<211> LENGTH: 174
<212> TYPE: PRT
<213> ORGANISM: Camelina sativa

<400> SEQUENCE: 16

Met Ala Tyr Glu Lys Val Asn Glu Leu Asn Leu Lys Asp Thr Glu
1               5                   10                  15

Leu Cys Leu Gly Leu Pro Gly Arg Thr Glu Glu Ile Lys Glu Glu Gln
            20                  25                  30

Glu Val Ser Cys Val Lys Ser Asn Asn Lys Arg Gln Phe Glu Glu Thr
        35                  40                  45

Arg Asp Glu Glu Glu Ser Thr Pro Pro Thr Lys Thr Gln Ile Val Gly
    50                  55                  60

Trp Pro Pro Val Arg Ser Tyr Arg Lys Asn Asn Ser Val Ser Tyr Val
65                  70                  75                  80

Lys Val Ser Met Asp Gly Ala Pro Tyr Leu Arg Lys Ile Asp Leu Lys
                85                  90                  95

Thr Tyr Lys Asn Tyr Pro Glu Leu Leu Lys Ala Leu Glu Asn Met Phe
            100                 105                 110

Lys Phe Thr Val Gly Glu Tyr Ser Glu Arg Glu Gly Tyr Lys Gly Ser
        115                 120                 125

Gly Phe Val Pro Thr Tyr Glu Asp Lys Asp Gly Asp Trp Met Leu Val
    130                 135                 140

Gly Asp Val Pro Trp Asp Met Phe Ser Ser Cys Lys Arg Leu Arg
145                 150                 155                 160

Ile Met Lys Gly Ser Asp Ala Pro Thr Leu Asp Ala Ser Leu
            165                 170
```

<210> SEQ ID NO 17
<211> LENGTH: 171
<212> TYPE: PRT
<213> ORGANISM: Raphanus sativus

<400> SEQUENCE: 17

```
Met Ala Tyr Glu Lys Val Asn Glu Ile Asn Leu Lys Asp Thr Glu Leu
1               5                   10                  15

Arg Leu Gly Leu Pro Gly Thr Glu Lys Val Lys Glu Glu Gln Asp Val
            20                  25                  30

Ser Cys Val Arg Ser Ile Lys Arg Gln Tyr Gln Ser Asp Asn Glu Glu
        35                  40                  45

Glu Ser Thr Pro Pro Thr Lys Thr Gln Ile Val Gly Trp Pro Pro Val
    50                  55                  60

Arg Ser Tyr Arg Lys Asn Asn Asn Ser Val Ser Tyr Val Lys Val Ser
65                  70                  75                  80

Met Asp Gly Ala Pro Tyr Leu Arg Lys Ile Asp Leu Lys Thr Tyr Lys
                85                  90                  95

Asn Tyr Pro Glu Leu Leu Arg Glu Leu Glu Asn Met Phe Lys Cys Thr
            100                 105                 110

Ile Gly Glu Tyr Asn Glu Arg Glu Gly Tyr Asn Gly Ser Glu Val Val
        115                 120                 125

Pro Thr Tyr Glu Asp Lys Asp Gly Asp Trp Met Leu Val Gly Asp Val
    130                 135                 140

Pro Trp Asp Met Phe Ser Ser Cys Lys Arg Leu Arg Ile Met Lys
145                 150                 155                 160

Gly Pro Asp Ala Leu Ala Leu Asp Ser Gly Leu
                165                 170
```

<210> SEQ ID NO 18
<211> LENGTH: 175
<212> TYPE: PRT
<213> ORGANISM: Raphanus sativus

<400> SEQUENCE: 18

```
Met Ala Tyr Glu Lys Val Asn Glu Leu Asn Leu Lys Asp Thr Glu Leu
1               5                   10                  15

Arg Leu Gly Leu Pro Gly Thr Glu Gln Val Lys Glu Glu Gln Asp Val
            20                  25                  30

Ser Cys Val Arg Ser Asn Lys Arg Gln Leu Gln Ser Asp Asn Glu Glu
        35                  40                  45

Glu Ser Thr Thr Pro Pro Thr Lys Thr Gln Ile Val Gly Trp Pro Pro
    50                  55                  60

Val Arg Ser Tyr Arg Lys Asn Asn Asn Asn Asn Ser Val Ser Tyr
65                  70                  75                  80

Val Lys Val Ser Met Asp Gly Ala Pro Tyr Leu Arg Lys Ile Asp Leu
                85                  90                  95

Lys Thr Tyr Lys Asn Tyr Pro Glu Leu Leu Lys Ala Leu Glu Asn Met
            100                 105                 110

Phe Lys Phe Thr Ile Gly Glu Tyr Cys Glu Arg Glu Gly Tyr Lys Gly
        115                 120                 125

Ser Glu Val Val Pro Thr Tyr Glu Asp Lys Asp Gly Asp Trp Met Leu
    130                 135                 140

Val Gly Asp Val Pro Trp Asp Met Phe Ser Ser Cys Lys Arg Leu
145                 150                 155                 160
```

```
Arg Ile Met Lys Gly Ser Asp Ala Leu Ala Leu Asp Ser Ala Leu
                165                 170                 175
```

<210> SEQ ID NO 19
<211> LENGTH: 185
<212> TYPE: PRT
<213> ORGANISM: Raphanus sativus

<400> SEQUENCE: 19

```
Met Ala Tyr Glu Lys Val Asn Glu Leu Asn Leu Lys Asp Thr Glu Leu
1               5                   10                  15

Arg Leu Gly Leu Pro Gly Thr Glu Gln Val Lys Glu Glu Gln Asp Val
            20                  25                  30

Ser Cys Val Arg Ser Asn Lys Arg Gln Leu Gln Ser Asp Asn Glu Glu
        35                  40                  45

Glu Ser Thr Thr Pro Thr Lys Thr Gln Ile Val Gly Trp Pro Pro
    50                  55                  60

Val Arg Ser Tyr Arg Lys Asn Asn Asn Asn Asn Asn Asn Asn Asn
65                  70                  75                  80

Asn Asn Asn Asn Asn Asn Ser Val Ser Tyr Val Lys Val Ser Met Asp
                85                  90                  95

Gly Ala Pro Tyr Leu Arg Lys Ile Asp Leu Lys Thr Tyr Lys Asn Tyr
            100                 105                 110

Pro Glu Leu Leu Lys Ala Leu Glu Asn Met Phe Lys Phe Thr Ile Gly
        115                 120                 125

Glu Tyr Cys Glu Arg Glu Gly Tyr Lys Gly Ser Glu Val Val Pro Thr
130                 135                 140

Tyr Glu Asp Lys Asp Gly Asp Trp Met Leu Val Gly Asp Val Pro Trp
145                 150                 155                 160

Asp Met Phe Ser Ser Ser Cys Lys Arg Leu Arg Ile Met Lys Gly Ser
                165                 170                 175

Asp Ala Leu Ala Leu Asp Ser Ala Leu
            180                 185
```

<210> SEQ ID NO 20
<211> LENGTH: 255
<212> TYPE: PRT
<213> ORGANISM: Brassica oleracea

<400> SEQUENCE: 20

```
Met Gly Gly His Ser Val Cys Val Leu Pro Leu Ser Pro Cys Leu Ile
1               5                   10                  15

Leu Ala Phe His Ala Pro Asp Asn Phe Tyr Leu Ser Ser Phe Lys Pro
            20                  25                  30

Asn Phe Tyr Ala Ser Ser Pro Thr Phe Ile Tyr Leu Ser Pro Ile Ser
        35                  40                  45

Ser Lys Ser Ile Ile Asn Gln Thr His Gln Gln Glu Gln Tyr Gln Glu
    50                  55                  60

Gln Glu Gln Glu Gln Glu Lys Asp Phe Ala Glu Arg Asn Leu Asp Phe
65                  70                  75                  80

Glu Lys Lys Met Ala Tyr Glu Lys Val Asn Glu Leu Asn Leu Lys Asp
                85                  90                  95

Thr Glu Leu Arg Leu Gly Leu Pro Gly Thr Gly Gln Val Lys Glu Glu
            100                 105                 110

Gln Glu Val Ser Cys Val Arg Ser Asn Lys Arg Gln His Gln Ser Asp
        115                 120                 125
```

```
Asn Glu Glu Ser Thr Pro Pro Thr Lys Thr Gln Ile Val Gly Trp
    130                 135                 140

Pro Pro Val Arg Ser Tyr Arg Lys Asn Asn Asn Ser Val Val Ser Tyr
145                 150                 155                 160

Val Lys Val Ser Lys Asp Gly Ala Pro Tyr Leu Arg Lys Ile Asp Leu
                165                 170                 175

Lys Thr Tyr Lys Asn Tyr Ser Glu Leu Leu Lys Glu Leu Glu Asn Met
                180                 185                 190

Phe Lys Phe Thr Ile Gly Glu Tyr Ser Glu Arg Glu Gly Tyr Arg Gly
            195                 200                 205

Ser Gly Val Val Pro Thr Tyr Glu Asp Lys Asp Gly Asp Trp Met Leu
    210                 215                 220

Val Gly Asp Val Pro Trp Asp Met Phe Ser Ser Cys Lys Arg Leu
225                 230                 235                 240

Arg Ile Met Lys Gly Ser Asp Ala Leu Ala Leu Asp Ser Ala Leu
                245                 250                 255

<210> SEQ ID NO 21
<211> LENGTH: 172
<212> TYPE: PRT
<213> ORGANISM: Brassica oleracea

<400> SEQUENCE: 21

Met Ala Tyr Glu Lys Val Asn Glu Leu Asn Leu Lys Asp Thr Glu Leu
1               5                   10                  15

Arg Leu Gly Leu Pro Gly Thr Gly Gln Val Lys Glu Glu Gln Glu Val
            20                  25                  30

Ser Cys Val Arg Ser Asn Lys Arg Gln His Gln Ser Asp Asn Glu Glu
        35                  40                  45

Glu Ser Thr Pro Pro Thr Lys Thr Gln Ile Val Gly Trp Pro Pro Val
    50                  55                  60

Arg Ser Tyr Arg Lys Asn Asn Asn Ser Val Val Ser Tyr Val Lys Val
65                  70                  75                  80

Ser Lys Asp Gly Ala Pro Tyr Leu Arg Lys Ile Asp Leu Lys Thr Tyr
                85                  90                  95

Lys Asn Tyr Ser Glu Leu Leu Lys Glu Leu Glu Asn Met Phe Lys Phe
            100                 105                 110

Thr Ile Gly Glu Tyr Ser Glu Arg Glu Gly Tyr Arg Gly Ser Gly Val
        115                 120                 125

Val Pro Thr Tyr Glu Asp Lys Asp Gly Asp Trp Met Leu Val Gly Asp
    130                 135                 140

Val Pro Trp Asp Met Phe Ser Ser Ser Cys Lys Arg Leu Arg Ile Met
145                 150                 155                 160

Lys Gly Ser Asp Ala Leu Ala Leu Asp Ser Ala Leu
                165                 170

<210> SEQ ID NO 22
<211> LENGTH: 253
<212> TYPE: PRT
<213> ORGANISM: Brassica napus

<400> SEQUENCE: 22

Met Gly Gly His Ser Val Cys Val Leu Pro Leu Ser Pro Cys Leu Ile
1               5                   10                  15

Leu Ala Phe His Ala Pro Asp Asn Phe Tyr Leu Ser Ser Phe Lys Pro
            20                  25                  30
```

```
Asn Phe Tyr Ala Ser Ser Pro Thr Phe Ile Tyr Leu Ser Pro Ile Ser
        35                  40                  45

Ser Lys Ser Ile Ile Asn Gln Thr His Gln Gln Glu Gln Tyr Gln Glu
 50                  55                  60

Gln Glu Gln Glu Gln Glu Lys Asp Phe Ala Asn Leu Asp Phe Glu Lys
 65                  70                  75                  80

Lys Met Ala Tyr Glu Lys Val Asn Glu Leu Asn Leu Lys Asp Thr Glu
                 85                  90                  95

Leu Arg Leu Gly Leu Pro Gly Thr Gly Gln Val Lys Glu Glu Gln Glu
                100                 105                 110

Val Ser Cys Val Arg Ser Asn Lys Arg Gln His Gln Ser Asp Asn Glu
                115                 120                 125

Glu Glu Ser Thr Pro Pro Thr Lys Thr Gln Ile Val Gly Trp Pro Pro
        130                 135                 140

Val Arg Ser Tyr Arg Lys Asn Asn Asn Ser Val Val Ser Tyr Val Lys
145                 150                 155                 160

Val Ser Lys Asp Gly Ala Pro Tyr Leu Arg Lys Ile Asp Leu Lys Thr
                165                 170                 175

Tyr Lys Asn Tyr Ser Glu Leu Leu Lys Glu Leu Glu Asn Met Phe Lys
                180                 185                 190

Phe Thr Ile Gly Glu Tyr Ser Glu Arg Glu Gly Tyr Arg Gly Ser Gly
                195                 200                 205

Val Val Pro Thr Tyr Glu Asp Lys Asp Gly Asp Trp Met Leu Val Gly
        210                 215                 220

Asp Val Pro Trp Asp Met Phe Ser Ser Cys Lys Arg Leu Arg Ile
225                 230                 235                 240

Met Lys Gly Ser Asp Ala Leu Ala Leu Asp Ser Ala Leu
                245                 250

<210> SEQ ID NO 23
<211> LENGTH: 172
<212> TYPE: PRT
<213> ORGANISM: Brassica napus

<400> SEQUENCE: 23

Met Ala Tyr Glu Lys Val Asn Glu Leu Asn Leu Lys Asp Thr Glu Leu
1               5                   10                  15

Arg Leu Gly Leu Pro Gly Thr Gly Gln Val Lys Glu Glu Gln Glu Val
                20                  25                  30

Ser Cys Val Arg Ser Asn Lys Arg Gln His Gln Ser Asp Asn Glu Glu
        35                  40                  45

Glu Ser Thr Pro Pro Thr Lys Thr Gln Ile Val Gly Trp Pro Pro Val
 50                  55                  60

Arg Ser Tyr Arg Lys Asn Asn Asn Ser Val Val Ser Tyr Val Lys Val
65                  70                  75                  80

Ser Met Asp Gly Ala Pro Tyr Leu Arg Lys Ile Asp Leu Lys Thr Tyr
                85                  90                  95

Lys Asn Tyr Ser Glu Leu Leu Lys Glu Leu Glu Asn Met Phe Lys Phe
                100                 105                 110

Thr Ile Gly Glu Tyr Ser Glu Arg Glu Gly Tyr Arg Gly Ser Gly Val
                115                 120                 125

Val Pro Thr Tyr Glu Asp Lys Asp Gly Asp Trp Met Leu Val Gly Asp
        130                 135                 140

Val Pro Trp Asp Met Phe Ser Ser Cys Lys Arg Leu Arg Ile Met
```

```
            145                 150                 155                 160
Lys Gly Ser Asp Ala Leu Ala Leu Asp Ser Ala Leu
                165                 170

<210> SEQ ID NO 24
<211> LENGTH: 255
<212> TYPE: PRT
<213> ORGANISM: Brassica rapa

<400> SEQUENCE: 24

Met Gly Gly His Ser Val Cys Val Leu Pro Leu Ser Pro Cys Leu Ile
1               5                   10                  15

Leu Ala Phe Asp Ala Pro Asp Asn Phe Tyr Leu Ser Ser Phe Lys Pro
                20                  25                  30

Asn Phe Tyr Ala Ser Ser Pro Thr Phe Ile Tyr Leu Ser Pro Ile Ser
            35                  40                  45

Ser Lys Ser Ile Ile Asn Gln Thr His Gln Gln Glu Gln Tyr Gln Glu
    50                  55                  60

Gln Glu Gln Glu Gln Glu Lys Asp Ser Ala Glu Arg Asn Leu Asp Cys
65                  70                  75                  80

Glu Lys Lys Met Ala Tyr Glu Lys Val Asn Glu Leu Asn Leu Lys Asp
                85                  90                  95

Thr Glu Leu Arg Leu Gly Leu Pro Gly Thr Gly Gln Val Lys Glu Glu
            100                 105                 110

Lys Glu Val Ser Cys Val Arg Ser Asn Lys Arg Gln His Gln Ser Asp
        115                 120                 125

Asn Glu Glu Glu Ser Thr Pro Pro Thr Lys Thr Gln Ile Val Gly Trp
130                 135                 140

Pro Pro Val Arg Ser Tyr Arg Lys Asn Asn Ser Val Val Ser Tyr
145                 150                 155                 160

Val Lys Val Ser Met Asp Gly Ala Pro Tyr Leu Arg Lys Ile Asp Leu
                165                 170                 175

Lys Thr Tyr Lys Asn Tyr Ser Glu Leu Leu Lys Glu Leu Glu Asn Met
            180                 185                 190

Phe Lys Phe Thr Ile Gly Glu Tyr Ser Glu Arg Glu Gly Tyr Arg Gly
        195                 200                 205

Ser Gly Val Val Pro Thr Tyr Glu Asp Lys Asp Gly Asp Trp Met Leu
    210                 215                 220

Val Gly Asp Val Pro Trp Asp Met Phe Ser Ser Cys Lys Arg Leu
225                 230                 235                 240

Arg Ile Met Lys Gly Ser Asp Ala Leu Ala Leu Asp Ser Ala Leu
                245                 250                 255

<210> SEQ ID NO 25
<211> LENGTH: 172
<212> TYPE: PRT
<213> ORGANISM: Brassica rapa

<400> SEQUENCE: 25

Met Ala Tyr Glu Lys Val Asn Glu Leu Asn Leu Lys Asp Thr Glu Leu
1               5                   10                  15

Arg Leu Gly Leu Pro Gly Thr Gly Gln Val Lys Glu Glu Lys Glu Val
                20                  25                  30

Ser Cys Val Arg Ser Asn Lys Arg Gln His Gln Ser Asp Asn Glu Glu
            35                  40                  45

Glu Ser Thr Pro Pro Thr Lys Thr Gln Ile Val Gly Trp Pro Pro Val
```

```
            50                  55                  60
Arg Ser Tyr Arg Lys Asn Asn Ser Val Ser Tyr Val Lys Val
 65                  70                  75                  80

Ser Met Asp Gly Ala Pro Tyr Leu Arg Lys Ile Asp Leu Lys Thr Tyr
                     85                  90                  95

Lys Asn Tyr Ser Glu Leu Leu Lys Glu Leu Glu Asn Met Phe Lys Phe
                    100                 105                 110

Thr Ile Gly Glu Tyr Ser Glu Arg Glu Gly Tyr Arg Gly Ser Gly Val
                115                 120                 125

Val Pro Thr Tyr Glu Asp Lys Asp Gly Asp Trp Met Leu Val Gly Asp
            130                 135                 140

Val Pro Trp Asp Met Phe Ser Ser Ser Cys Lys Arg Leu Arg Ile Met
145                 150                 155                 160

Lys Gly Ser Asp Ala Leu Ala Leu Asp Ser Ala Leu
                165                 170

<210> SEQ ID NO 26
<211> LENGTH: 253
<212> TYPE: PRT
<213> ORGANISM: Brassica napus

<400> SEQUENCE: 26

Met Gly Gly His Ser Val Cys Val Leu Pro Leu Ser Pro Cys Leu Ile
 1               5                  10                  15

Leu Ala Phe Asp Ala Pro Asp Asn Phe Tyr Leu Ser Ser Phe Lys Pro
                 20                  25                  30

Asn Phe Tyr Ala Ser Ser Pro Thr Phe Ile Tyr Leu Ser Pro Ile Ser
                 35                  40                  45

Ser Lys Ser Ile Ile Asn Gln Thr His Gln Gln Glu Gln Tyr Gln Glu
 50                  55                  60

Gln Glu Gln Glu Gln Glu Lys Asp Ser Ala Asn Leu Asp Cys Glu Lys
 65                  70                  75                  80

Lys Met Ala Tyr Glu Lys Val Asn Glu Leu Asn Leu Lys Asp Thr Glu
                 85                  90                  95

Leu Arg Leu Gly Leu Pro Gly Thr Gly Gln Val Lys Glu Glu Lys Glu
                100                 105                 110

Val Ser Cys Val Arg Ser Asn Lys Arg Gln His Gln Ser Asp Asn Glu
                115                 120                 125

Glu Glu Ser Thr Pro Pro Thr Lys Thr Gln Ile Val Gly Trp Pro Pro
            130                 135                 140

Val Arg Ser Tyr Arg Lys Asn Asn Asn Ser Val Val Ser Tyr Val Lys
145                 150                 155                 160

Val Ser Met Asp Gly Ala Pro Tyr Leu Arg Lys Ile Asp Leu Lys Thr
                165                 170                 175

Tyr Lys Asn Tyr Ser Glu Leu Leu Lys Glu Leu Glu Asn Met Phe Lys
                180                 185                 190

Phe Thr Ile Gly Glu Tyr Ser Glu Arg Glu Gly Tyr Arg Gly Ser Gly
                195                 200                 205

Val Val Pro Thr Tyr Glu Asp Lys Asp Gly Asp Trp Met Leu Val Gly
            210                 215                 220

Asp Val Pro Trp Asp Met Phe Ser Ser Ser Cys Lys Arg Leu Arg Ile
225                 230                 235                 240

Met Lys Gly Ser Asp Ala Leu Ala Leu Asp Ser Ala Leu
                245                 250
```

<210> SEQ ID NO 27
<211> LENGTH: 171
<212> TYPE: PRT
<213> ORGANISM: Brassica rapa

<400> SEQUENCE: 27

Met Ala Tyr Glu Lys Val Asn Glu Leu Asn Leu Lys Asp Thr Glu Leu
1               5                   10                  15

Arg Leu Gly Leu Pro Gly Thr Glu Gln Ala Lys Glu Glu Gln Glu Val
            20                  25                  30

Ser Cys Val Arg Ser Ser Lys Arg Gln Leu Gln Ser Asp Asn Glu Glu
        35                  40                  45

Glu Ser Thr Pro Pro Thr Lys Ser Gln Ile Val Gly Trp Pro Pro Val
    50                  55                  60

Arg Ser Tyr Arg Lys Asn Asn Asn Ser Val Ser Tyr Val Lys Val Ser
65                  70                  75                  80

Met Asp Gly Ala Pro Tyr Leu Arg Lys Ile Asp Leu Lys Thr Tyr Lys
                85                  90                  95

Asn Tyr Pro Glu Leu Leu Lys Ala Leu Glu Asn Met Phe Lys Phe Thr
            100                 105                 110

Ile Gly Glu Tyr Ser Glu Arg Glu Gly Tyr Lys Gly Ser Gly Val Leu
        115                 120                 125

Pro Thr Tyr Glu Asp Lys Asp Gly Asp Trp Met Leu Val Gly Asp Val
    130                 135                 140

Pro Trp Asp Met Phe Ser Ser Cys Lys Arg Leu Arg Ile Met Lys
145                 150                 155                 160

Gly Ser Asp Ala Leu Val Leu Asp Ser Ala Leu
                165                 170

<210> SEQ ID NO 28
<211> LENGTH: 171
<212> TYPE: PRT
<213> ORGANISM: Brassica oleracea

<400> SEQUENCE: 28

Met Thr Tyr Glu Lys Val Asn Glu Leu Asn Leu Lys Asp Thr Glu Leu
1               5                   10                  15

Arg Leu Gly Leu Pro Gly Thr Glu Gln Ala Lys Glu Glu Gln Glu Val
            20                  25                  30

Ser Cys Val Arg Ser Asn Lys Arg Gln Leu Gln Ser Asp Asn Glu Glu
        35                  40                  45

Glu Ser Thr Pro Pro Thr Lys Thr Gln Ile Val Gly Trp Pro Pro Val
    50                  55                  60

Arg Ser Tyr Arg Lys Asn Asn Asn Ser Val Ser Tyr Val Lys Val Ser
65                  70                  75                  80

Met Asp Gly Ala Pro Tyr Leu Arg Lys Ile Asp Leu Lys Thr Tyr Lys
                85                  90                  95

Asn Tyr Pro Glu Leu Leu Lys Ala Leu Glu Asn Met Phe Lys Phe Thr
            100                 105                 110

Ile Gly Glu Tyr Ser Glu Arg Glu Gly Tyr Lys Gly Ser Gly Val Ile
        115                 120                 125

Pro Thr Tyr Glu Asp Lys Asp Gly Asp Trp Met Leu Val Gly Asp Val
    130                 135                 140

Pro Trp Asp Met Phe Ser Ser Cys Lys Arg Leu Arg Ile Met Lys
145                 150                 155                 160

Gly Ser Asp Ala Leu Ala Leu Asp Ser Ala Leu
                165                 170

<210> SEQ ID NO 29
<211> LENGTH: 262
<212> TYPE: PRT
<213> ORGANISM: Brassica oleracea

<400> SEQUENCE: 29

Met Asp Gly Gln Ser Val Tyr Val Pro Pro Leu Ser Pro Cys Leu Ile
1               5                   10                  15

Leu Ala Ser His Ala Pro Asp Asn Phe Tyr Leu Ser Ser Phe Tyr Pro
            20                  25                  30

Asn Phe Tyr Ala Ser Ser Pro Thr Phe Ile Tyr Leu Ser Pro Leu Phe
        35                  40                  45

Ser Ser Ser Thr Lys Leu Thr Asn Lys Lys Asn His Asn Lys Asn Lys
    50                  55                  60

Arg Arg Ile Leu Gln His Phe Ser Gln Lys Lys Thr Thr Gln Glu His
65                  70                  75                  80

Arg Glu Ile Asn Phe Leu Ile Leu Lys Lys Thr Met Thr Tyr Glu Lys
                85                  90                  95

Val Asn Glu Leu Asn Leu Lys Asp Thr Glu Leu Arg Leu Gly Leu Pro
            100                 105                 110

Gly Thr Glu Gln Ala Lys Glu Glu Gln Glu Val Ser Cys Val Arg Ser
        115                 120                 125

Asn Lys Arg Gln Leu Gln Ser Asp Asn Glu Glu Ser Thr Pro Pro
    130                 135                 140

Thr Lys Thr Gln Ile Val Gly Trp Pro Pro Val Arg Ser Tyr Arg Lys
145                 150                 155                 160

Asn Asn Asn Ser Val Ser Tyr Val Lys Val Ser Met Asp Gly Ala Pro
                165                 170                 175

Tyr Leu Arg Lys Ile Asp Leu Lys Thr Tyr Lys Asn Tyr Pro Glu Leu
            180                 185                 190

Leu Lys Ala Leu Glu Asn Met Phe Lys Phe Thr Ile Gly Glu Tyr Ser
        195                 200                 205

Glu Arg Glu Gly Tyr Lys Gly Ser Gly Val Ile Pro Thr Tyr Glu Asp
    210                 215                 220

Lys Asp Gly Asp Trp Met Leu Val Gly Asp Val Pro Trp Asp Met Phe
225                 230                 235                 240

Ser Ser Ser Cys Lys Arg Leu Arg Ile Met Lys Gly Ser Asp Ala Leu
                245                 250                 255

Ala Leu Asp Ser Ala Leu
            260

<210> SEQ ID NO 30
<211> LENGTH: 171
<212> TYPE: PRT
<213> ORGANISM: Brassica napus

<400> SEQUENCE: 30

Met Thr Tyr Glu Lys Val Asn Glu Leu Asn Leu Lys Asp Thr Glu Leu
1               5                   10                  15

Arg Leu Gly Leu Pro Gly Thr Glu Gln Ala Lys Glu Glu Gln Glu Val
            20                  25                  30

Ser Cys Val Arg Ser Ser Lys Arg Gln Leu Gln Ser Asp Asn Glu Glu
        35                  40                  45

```
Glu Ser Thr Pro Pro Thr Lys Ser Gln Ile Val Gly Trp Pro Pro Val
 50                  55                  60

Arg Ser Tyr Arg Lys Asn Asn Asn Ser Val Ser Tyr Val Lys Val Ser
 65                  70                  75                  80

Met Asp Gly Ala Pro Tyr Leu Arg Lys Ile Asp Leu Lys Thr Tyr Lys
                 85                  90                  95

Asn Tyr Pro Glu Leu Leu Lys Ala Leu Glu Asn Met Phe Lys Phe Thr
            100                 105                 110

Ile Gly Glu Tyr Ser Glu Arg Glu Gly Tyr Lys Gly Ser Gly Val Ile
        115                 120                 125

Pro Thr Tyr Glu Asp Lys Asp Gly Asp Trp Met Leu Val Gly Asp Val
    130                 135                 140

Pro Trp Asp Met Phe Ser Ser Ser Cys Lys Arg Leu Arg Ile Met Lys
145                 150                 155                 160

Gly Ser Asp Ala Leu Ala Leu Asp Ser Ala Leu
                165                 170

<210> SEQ ID NO 31
<211> LENGTH: 236
<212> TYPE: PRT
<213> ORGANISM: Raphanus sativus

<400> SEQUENCE: 31

Met Leu Pro Thr Thr Ser Leu Ser Leu Pro Leu Thr Leu Thr Ser Met
  1               5                  10                  15

His Leu Leu Pro Pro Val Tyr Ile Ser Leu Ser Leu Lys Pro Ile Ile
                 20                  25                  30

Asn Gln Thr His Gln Gln Glu Gln Glu Glu Gln Gly Phe Cys Phe
             35                  40                  45

Gly Asn His Thr Arg Thr Tyr Arg Glu Arg Leu Leu Asp Leu Glu Lys
         50                  55                  60

Met Ala Tyr Glu Lys Val Asn Glu Leu Asn Leu Lys Asp Thr Glu Leu
 65                  70                  75                  80

Arg Leu Gly Leu Pro Gly Thr Glu Gln Asp Lys Glu Gln Glu Val
                 85                  90                  95

Ser Cys Val Arg Ser Ile Lys Arg Gln Leu Gln Ser Asp Asn Glu Glu
            100                 105                 110

Ala Ser Pro Pro Thr Lys Thr Gln Ile Val Gly Trp Pro Pro Val
        115                 120                 125

Arg Ser Tyr Arg Lys Asn Asn Asn Ser Val Ser Tyr Val Lys Val Ser
    130                 135                 140

Met Asp Gly Ala Pro Tyr Leu Arg Lys Ile Asp Leu Lys Thr Tyr Lys
145                 150                 155                 160

Asn Tyr Ala Glu Leu Leu Lys Gly Leu Glu Asn Met Phe Lys Phe Thr
                165                 170                 175

Ile Gly Glu Tyr Cys Glu Arg Glu Gly Tyr Lys Gly Ser Gly Val Val
            180                 185                 190

Pro Thr Tyr Glu Asp Lys Asp Gly Asp Trp Met Leu Val Gly Asp Val
        195                 200                 205

Pro Trp Asp Met Phe Ser Ser Ser Cys Lys Arg Leu Arg Ile Met Lys
    210                 215                 220

Gly Ser Asp Ala Leu Ala Leu Asp Ser Ala Leu Leu
225                 230                 235

<210> SEQ ID NO 32
```

```
<211> LENGTH: 171
<212> TYPE: PRT
<213> ORGANISM: Brassica oleracea

<400> SEQUENCE: 32

Met Ala Tyr Glu Lys Val Asn Glu Leu Asn Leu Lys Asp Thr Glu Leu
1               5                   10                  15

Arg Leu Gly Leu Pro Gly Ile Glu Gln Asp Lys Glu Glu Gln Glu Val
                20                  25                  30

Ser Cys Val Arg Ser Asn Lys Arg Gln Leu Gln Ser Asp Asn Glu Glu
            35                  40                  45

Glu Ser Thr Leu Pro Thr Lys Thr Gln Ile Val Gly Trp Pro Pro Val
50                  55                  60

Arg Ser Tyr Arg Lys Lys Asn Asn Ser Val Ser Tyr Val Lys Val Ser
65                  70                  75                  80

Met Asp Gly Ala Pro Tyr Leu Arg Lys Ile Asp Leu Lys Thr Tyr Lys
                85                  90                  95

Asn Tyr Pro Glu Leu Leu Lys Ala Leu Glu Asn Leu Phe Lys Phe Thr
            100                 105                 110

Ile Gly Glu Tyr Ser Glu Arg Asp Gly Tyr Lys Gly Ser Gly Val Val
        115                 120                 125

Pro Thr Tyr Glu Asp Lys Asp Gly Asp Trp Met Leu Val Gly Asp Val
130                 135                 140

Pro Trp Asp Met Phe Ser Ser Ser Cys Lys Arg Leu Arg Ile Met Lys
145                 150                 155                 160

Gly Ser Asp Ala Leu Ala Leu Asp Ser Ala Leu
                165                 170

<210> SEQ ID NO 33
<211> LENGTH: 171
<212> TYPE: PRT
<213> ORGANISM: Brassica napus

<400> SEQUENCE: 33

Met Ala Tyr Glu Lys Val Asn Glu Leu Asn Leu Lys Asp Thr Glu Leu
1               5                   10                  15

Arg Leu Gly Leu Pro Gly Ile Glu Gln Asp Lys Glu Glu Gln Glu Val
                20                  25                  30

Ser Cys Val Arg Ser Asn Lys Arg Gln Leu Gln Ser Asp Asn Glu Glu
            35                  40                  45

Glu Ser Thr Leu Pro Thr Lys Thr Gln Ile Val Gly Trp Pro Pro Val
50                  55                  60

Arg Ser Tyr Arg Lys Asn Asn Asn Ser Val Ser Tyr Val Lys Val Ser
65                  70                  75                  80

Met Asp Gly Ala Pro Tyr Leu Arg Lys Ile Asp Leu Lys Thr Tyr Lys
                85                  90                  95

Asn Tyr Pro Glu Leu Leu Lys Ala Leu Glu Asn Leu Phe Lys Phe Thr
            100                 105                 110

Ile Gly Glu Tyr Ser Glu Arg Asp Gly Tyr Lys Gly Ser Gly Val Val
        115                 120                 125

Pro Thr Tyr Glu Asp Lys Asp Gly Asp Trp Met Leu Val Gly Asp Val
130                 135                 140

Pro Trp Asp Met Phe Ser Ser Ser Cys Lys Arg Leu Arg Ile Met Lys
145                 150                 155                 160

Gly Ser Asp Ala Leu Ala Leu Asp Ser Ala Leu
                165                 170
```

<210> SEQ ID NO 34
<211> LENGTH: 255
<212> TYPE: PRT
<213> ORGANISM: Brassica napus

<400> SEQUENCE: 34

Met Gly Gly His Ser Val Cys Val Pro Pro Leu Ser Pro Cys Leu Phe
1               5                   10                  15

Leu Ala Phe His Ala Pro Asp Asn Ile Ser Leu Ser Ser Phe Asn Pro
                20                  25                  30

Asn Phe Tyr Ala Ser Ser Pro Ser Cys Ile Tyr Leu Ser Phe Ser Lys
            35                  40                  45

Pro Ile Ile Asn Gln Thr His Lys Gln Glu Gln Glu Glu Glu Gln Gly
50                  55                  60

Phe Cys Phe Gly Tyr Ile Thr Gln Arg His Ile Glu Arg Gly Val Leu
65                  70                  75                  80

Ile Leu Lys Lys Met Ala Tyr Glu Lys Val Asn Glu Leu Asn Leu Lys
                85                  90                  95

Asp Thr Glu Leu Arg Leu Gly Leu Pro Gly Ile Glu Gln Asp Lys Glu
            100                 105                 110

Glu Gln Glu Val Ser Cys Val Arg Ser Asn Lys Arg Gln Leu Gln Ser
        115                 120                 125

Asp Asn Glu Glu Glu Ser Thr Leu Pro Thr Lys Thr Gln Ile Val Gly
130                 135                 140

Trp Pro Pro Val Arg Ser Tyr Arg Lys Asn Asn Asn Ser Val Ser Tyr
145                 150                 155                 160

Val Lys Val Ser Met Asp Gly Ala Pro Tyr Leu Arg Lys Ile Asp Leu
                165                 170                 175

Lys Thr Tyr Lys Asn Tyr Pro Glu Leu Leu Lys Ala Leu Glu Asn Leu
            180                 185                 190

Phe Lys Phe Thr Ile Gly Glu Tyr Ser Glu Arg Asp Gly Tyr Lys Gly
        195                 200                 205

Ser Gly Val Val Pro Thr Tyr Glu Asp Lys Asp Gly Asp Trp Met Leu
210                 215                 220

Val Gly Asp Val Pro Trp Asp Met Phe Ser Ser Ser Cys Lys Arg Leu
225                 230                 235                 240

Arg Ile Met Lys Gly Ser Asp Ala Leu Ala Leu Asp Ser Ala Leu
                245                 250                 255

<210> SEQ ID NO 35
<211> LENGTH: 171
<212> TYPE: PRT
<213> ORGANISM: Brassica napus

<400> SEQUENCE: 35

Met Ala Tyr Glu Lys Val Asn Glu Leu Asn Leu Lys Asp Thr Glu Leu
1               5                   10                  15

Arg Leu Gly Leu Pro Gly Ile Glu Gln Asp Lys Glu Glu Gln Glu Val
                20                  25                  30

Ser Cys Val Arg Ser Asn Lys Arg Gln Leu Gln Ser Asp Asn Glu Glu
            35                  40                  45

Glu Ser Thr Leu Pro Thr Lys Thr Gln Ile Val Gly Trp Pro Pro Val
50                  55                  60

Arg Ser Tyr Arg Lys Asn Asn Asn Ser Val Ser Tyr Val Lys Val Ser
65                  70                  75                  80

```
Met Asp Gly Ala Pro Tyr Leu Arg Lys Ile Asp Leu Lys Thr Tyr Lys
                85                  90                  95

Asn Tyr Pro Glu Leu Leu Lys Ala Leu Glu Asn Leu Phe Lys Phe Thr
            100                 105                 110

Ile Gly Glu Tyr Ser Glu Arg Glu Gly Tyr Lys Gly Ser Gly Val Val
        115                 120                 125

Pro Thr Tyr Glu Asp Lys Asp Gly Asp Trp Met Leu Val Gly Asp Val
    130                 135                 140

Pro Trp Asp Met Phe Ser Ser Cys Lys Arg Leu Arg Ile Met Lys
145                 150                 155                 160

Gly Ser Asp Ala Leu Ala Leu Asp Ser Ala Leu
                165                 170

<210> SEQ ID NO 36
<211> LENGTH: 171
<212> TYPE: PRT
<213> ORGANISM: Brassica napus

<400> SEQUENCE: 36

Met Ala Tyr Glu Lys Val Asn Glu Leu Asn Leu Lys Asp Thr Glu Leu
1               5                   10                  15

Arg Leu Gly Leu Pro Gly Thr Glu Gln Asp Lys Glu Gln Glu Val
            20                  25                  30

Ser Cys Val Arg Ser Asn Lys Arg Gln Leu Gln Ser Asp Asn Glu Glu
        35                  40                  45

Glu Ser Thr Leu Pro Thr Lys Thr Gln Ile Val Gly Trp Pro Pro Val
50                  55                  60

Arg Ser Tyr Arg Lys Asn Asn Asn Ser Val Ser Tyr Val Lys Val Ser
65                  70                  75                  80

Met Asp Gly Ala Pro Tyr Leu Arg Lys Ile Asp Leu Lys Thr Tyr Lys
                85                  90                  95

Asn Tyr Pro Glu Leu Leu Lys Ala Leu Glu Asn Leu Phe Lys Phe Thr
            100                 105                 110

Ile Gly Glu Tyr Ser Glu Arg Glu Gly Tyr Lys Gly Ser Gly Val Val
        115                 120                 125

Pro Thr Tyr Glu Asp Lys Asp Gly Asp Trp Met Leu Val Gly Asp Val
    130                 135                 140

Pro Trp Asp Met Phe Ser Ser Cys Lys Arg Leu Arg Ile Met Lys
145                 150                 155                 160

Gly Ser Asp Ala Leu Ala Leu Asp Ser Ala Leu
                165                 170

<210> SEQ ID NO 37
<211> LENGTH: 171
<212> TYPE: PRT
<213> ORGANISM: Brassica rapa

<400> SEQUENCE: 37

Met Ala Tyr Glu Lys Val Asn Glu Leu Asn Leu Lys Asp Thr Glu Leu
1               5                   10                  15

Arg Leu Gly Leu Pro Gly Thr Glu Gln Asp Lys Glu Gln Glu Val
            20                  25                  30

Ser Cys Val Arg Ser Asn Lys Arg Gln Leu Gln Ser Asp Asn Glu Glu
        35                  40                  45

Glu Ser Thr Leu Pro Thr Lys Thr Gln Ile Val Gly Trp Pro Pro Val
50                  55                  60
```

```
Arg Ser Tyr Arg Lys Asn Asn Ser Val Ser Tyr Val Lys Val Ser
 65                  70                  75                  80

Met Asp Gly Ala Pro Tyr Leu Arg Lys Ile Asp Leu Lys Thr Tyr Lys
                 85                  90                  95

Asn Tyr Pro Glu Leu Leu Lys Ala Leu Glu Asn Leu Phe Lys Phe Thr
            100                 105                 110

Ile Gly Glu Tyr Asn Glu Arg Glu Gly Tyr Lys Gly Ser Gly Val Val
        115                 120                 125

Pro Thr Tyr Glu Asp Lys Asp Gly Asp Trp Met Leu Val Gly Asp Val
130                 135                 140

Pro Trp Asp Met Phe Ser Ser Cys Lys Arg Leu Arg Ile Met Lys
145                 150                 155                 160

Gly Ser Asp Ala Leu Ala Leu Asp Ser Ala Leu
                165                 170

<210> SEQ ID NO 38
<211> LENGTH: 173
<212> TYPE: PRT
<213> ORGANISM: Eutrema salsugineum

<400> SEQUENCE: 38

Met Ala Tyr Glu Lys Val Asn Glu Leu Asn Leu Lys Asp Thr Glu Leu
1               5                   10                  15

Arg Leu Gly Leu Pro Gly Thr Asp Glu Asn Lys Gln Glu Gln Glu Val
                20                  25                  30

Ser Cys Val Lys Ser Asn Lys Arg Gln Phe His Glu Gly Thr Cys Glu
            35                  40                  45

Gln Glu Glu Glu Glu Ser Thr Pro Pro Thr Lys Thr Gln Ile Val
        50                  55                  60

Gly Trp Pro Pro Val Arg Ser Tyr Arg Lys Asn Asn Ser Val Ser
 65                  70                  75                  80

Tyr Val Lys Val Ser Met Asp Gly Ala Pro Tyr Leu Arg Lys Ile Asp
                 85                  90                  95

Leu Lys Thr Tyr Lys Asn Tyr Pro Glu Leu Leu Lys Ala Leu Glu Asn
            100                 105                 110

Met Phe Lys Phe Thr Ile Gly Glu Tyr Ser Glu Arg Glu Gly Tyr Lys
        115                 120                 125

Gly Ser Gly Val Val Pro Thr Tyr Glu Asp Lys Asp Gly Asp Trp Met
130                 135                 140

Leu Val Gly Asp Val Pro Trp Asp Met Phe Ser Ser Ser Cys Lys Arg
145                 150                 155                 160

Leu Arg Ile Met Lys Gly Ser Asp Ala Asp Ser Ser Leu
                165                 170

<210> SEQ ID NO 39
<211> LENGTH: 65
<212> TYPE: PRT
<213> ORGANISM: Helianthus annuus

<400> SEQUENCE: 39

Gly Asn Gly Gly Gly Lys Asn Arg Asn Met Glu Val Ala Val Gly Trp
1               5                   10                  15

Pro Pro Val Cys Ser Tyr Arg Lys Arg Thr Ile Ile Lys Met Tyr Val
                20                  25                  30

Lys Val Ser Met Asp Gly Ala Pro Phe Leu Arg Lys Ile Asp Ile Asn
            35                  40                  45
```

<210> SEQ ID NO 40
<211> LENGTH: 115
<212> TYPE: PRT
<213> ORGANISM: Vitis vinifera

<400> SEQUENCE: 40

Asn Glu Thr Pro Pro Asn His Thr Gly Thr Gly Asn Asn Ser Ser
1               5                   10                  15

Ala Pro Ala Thr Lys Ala Gln Val Val Gly Trp Pro Pro Ile Arg Ser
            20                  25                  30

Phe Arg Lys Asn Thr Leu Ala Thr Thr Ser Lys Asn Thr Glu Val Asp
        35                  40                  45

Gly Lys Ala Gly Pro Gly Ala Leu Phe Val Lys Val Ser Met Asp Gly
    50                  55                  60

Ala Pro Tyr Leu Arg Lys Val Asp Leu Arg Asn Tyr Ser Ala Tyr Gln
65                  70                  75                  80

Glu Leu Ser Ser Ala Leu Glu Lys Met Phe Ser Cys Phe Thr Ile Gly
                85                  90                  95

Gln Tyr Gly Ser His Gly Ala Pro Gly Arg Glu Met Leu Ser Glu Ser
            100                 105                 110

Lys Leu Lys
        115

<210> SEQ ID NO 41
<211> LENGTH: 115
<212> TYPE: PRT
<213> ORGANISM: Glycine max

<400> SEQUENCE: 41

Asn Val Ser Lys Glu Lys Thr Leu Leu Lys Asp Pro Ala Lys Pro Pro
1               5                   10                  15

Ala Lys Ala Gln Val Val Gly Trp Pro Pro Val Arg Ser Tyr Arg Lys
            20                  25                  30

Asn Met Met Ala Val Gln Lys Val Ser Thr Glu Asp Val Ala Glu Lys
        35                  40                  45

Thr Thr Ser Ser Thr Ala Asn Pro Gly Ala Phe Val Lys Val Ser Met
    50                  55                  60

Asp Gly Ala Pro Tyr Leu Arg Lys Val Asp Leu Thr Met Tyr Lys Ser
65                  70                  75                  80

Tyr Lys Glu Leu Ser Asp Ala Leu Ala Lys Met Phe Ser Ser Phe Thr
                85                  90                  95

Met Gly Asn Tyr Gly Ala Gln Gly Met Ile Asp Phe Met Asn Glu Ser
            100                 105                 110

Lys Leu Met
        115

<210> SEQ ID NO 42
<211> LENGTH: 116
<212> TYPE: PRT
<213> ORGANISM: Coffea canephora

<400> SEQUENCE: 42

Gln Glu Lys Lys Pro Gln Val Ser Ala Ala Asn Gly His Ala Ala Ala
1               5                   10                  15

Pro Ala Ala Lys Ala Gln Val Val Gly Trp Pro Pro Ile Arg Ser Phe
                20                  25                  30

Arg Lys Asn Ser Met Ala Ile Asn Pro Pro Lys Thr Asp Glu Asp Ala
            35                  40                  45

Asp Ala Lys Leu Gly Thr Gly Cys Leu Tyr Val Lys Val Ser Met Asp
50                  55                  60

Gly Ala Pro Tyr Leu Arg Lys Val Asp Ile Lys Ile Tyr Ser Ser Tyr
65                  70                  75                  80

Lys Asp Leu Ser Ser Ala Leu Glu Lys Met Phe Ser Cys Phe Thr Ile
                85                  90                  95

Gly Gln Cys Gly Ser His Gly Val His Ile Arg Asp Gly Met Ser Glu
                100                 105                 110

Ser Arg Leu Met
            115

<210> SEQ ID NO 43
<211> LENGTH: 89
<212> TYPE: PRT
<213> ORGANISM: Gossypium raimondii

<400> SEQUENCE: 43

Cys Gly Val Asn Gly Cys Lys Ser Asp Asp Gln Asn Glu Thr Ala Pro
1               5                   10                  15

Pro Pro Pro Lys Ala Gln Ile Val Gly Trp Pro Pro Ile Arg Ser Tyr
                20                  25                  30

Arg Lys Asn Asn Ile Gln Thr Lys Lys Asn Glu Ser Glu Gly Gly Gly
            35                  40                  45

Ile Tyr Val Lys Val Ser Met Asp Gly Ala Pro Tyr Leu Arg Lys Ile
50                  55                  60

Asp Leu Lys Val Tyr Ser Gly Tyr Pro Glu Leu Leu Gln Ala Ile Glu
65                  70                  75                  80

Asn Met Phe Lys Phe Thr Ile Val Leu
                85

<210> SEQ ID NO 44
<211> LENGTH: 79
<212> TYPE: PRT
<213> ORGANISM: Sisymbrium orientale

<400> SEQUENCE: 44

Asn Glu Glu Asn Arg Glu Glu Glu Ser Thr Pro Thr Lys Thr
1               5                   10                  15

Gln Ile Val Gly Trp Pro Pro Val Arg Ser Tyr Arg Lys Asn Asn Asn
                20                  25                  30

Ser Val Ser Tyr Val Lys Val Ser Met Asp Gly Ala Pro Tyr Leu Arg
            35                  40                  45

Lys Ile Asp Leu Lys Thr Tyr Lys Asn Tyr Pro Glu Leu Leu Lys Ala
                50                  55                  60

Leu Glu Asn Met Phe Lys Phe Thr Val Gly Glu Tyr Cys Glu Arg
65                  70                  75

<210> SEQ ID NO 45
<211> LENGTH: 70
<212> TYPE: PRT
<213> ORGANISM: Sisymbrium orientale -continued

<400> SEQUENCE: 45

Asn Glu Glu Asn Arg Glu Glu Glu Ser Thr Pro Pro Thr Lys Thr
1               5                   10                  15

Gln Ile Val Gly Trp Pro Val Arg Ser Tyr Val Lys Val Ser Met
            20                  25                  30

Asp Gly Ala Pro Tyr Leu Arg Lys Ile Asp Leu Lys Thr Tyr Lys Asn
        35                  40                  45

Tyr Pro Glu Leu Leu Lys Ala Leu Glu Asn Met Phe Lys Phe Thr Val
50                  55                  60

Gly Glu Tyr Cys Glu Arg
65              70

<210> SEQ ID NO 46
<211> LENGTH: 87
<212> TYPE: PRT
<213> ORGANISM: Phaseolus vulgaris

<400> SEQUENCE: 46

Lys Gly Ser Asn Ala Pro Lys Thr Val Gln Thr Glu Ala Ala Pro Pro
1               5                   10                  15

Ala Lys Ala Lys Ile Val Gly Trp Pro Pro Ile Arg Ser Tyr Arg Lys
            20                  25                  30

Asn Ser Leu Gln Glu Asn Glu Gly Ala Gly Ile Tyr Val Lys Val Ser
        35                  40                  45

Met Asp Gly Ala Pro Tyr Leu Arg Lys Ile Asp Leu Lys Val Tyr Gly
50                  55                  60

Gly Tyr Thr Gln Leu Leu Ile Ala Leu Glu Thr Met Phe Lys Leu Thr
65                  70                  75                  80

Ile Gly Glu Tyr Ser Glu Lys
                85

<210> SEQ ID NO 47
<211> LENGTH: 93
<212> TYPE: PRT
<213> ORGANISM: Beta vulgaris

<400> SEQUENCE: 47

Ser Thr Asn Asn Ser Ser Val Ser Asp Ala Arg Asn Glu Asp Cys Pro
1               5                   10                  15

Pro Pro Ser Lys Thr Gln Ile Val Gly Trp Pro Pro Ile Arg Ser Tyr
            20                  25                  30

Arg Lys Asn Asn Leu Gln Pro Lys Lys Thr Glu Thr Asp Ala Ser Gly
        35                  40                  45

Met Tyr Val Lys Val Ser Met Asp Gly Ala Pro Tyr Leu Arg Lys Ile
50                  55                  60

Asp Leu Lys Met Tyr Gln Ser Tyr Ala Glu Leu Leu Lys Gly Leu Glu
65                  70                  75                  80

Ser Met Phe Arg Ile Cys Ile Gly Lys Tyr Ser Glu Arg
                85                  90

<210> SEQ ID NO 48
<211> LENGTH: 78
<212> TYPE: PRT
<213> ORGANISM: Capsicum annuum

<400> SEQUENCE: 48

Ser Asp Met Ile Asn Ser Asn Asp Asp Glu Pro Ala Pro Lys Ala Gln
1               5                   10                  15

```
Val Val Gly Trp Pro Pro Val Arg Ser Tyr Arg Lys Asn Val Leu Gln
            20                  25                  30

Ala Ser Tyr Val Lys Val Ser Met Asp Gly Ala Ala Tyr Leu Arg Lys
            35                  40                  45

Ile Asn Leu Asn Val Tyr Lys Ser Tyr Pro Gln Leu Leu Lys Ala Leu
50                  55                  60

Asp Asn Met Phe Lys Cys Ser Ile Gly Val Tyr Ser Glu Arg
65                  70                  75
```

<210> SEQ ID NO 49
<211> LENGTH: 76
<212> TYPE: PRT
<213> ORGANISM: Solanum lycopersicum

<400> SEQUENCE: 49

```
Ser His Arg Asn Asn Asn Asp Glu Pro Pro Gln Lys Ala Gln Val Val
1               5                   10                  15

Gly Trp Pro Pro Val Arg Ser Tyr Arg Lys Asn Ile Leu Glu Ala Ser
            20                  25                  30

Tyr Val Lys Val Ser Met Asp Gly Ala Ala Tyr Leu Arg Lys Ile Asp
            35                  40                  45

Leu Asn Thr Tyr Lys Ser Tyr Pro Gln Leu Leu Lys Ala Leu Glu Asn
50                  55                  60

Met Phe Lys Cys Ser Ile Asp Val Tyr Ser Glu Thr
65                  70                  75
```

<210> SEQ ID NO 50
<211> LENGTH: 70
<212> TYPE: PRT
<213> ORGANISM: Solanum tuberosum

<400> SEQUENCE: 50

```
Ser His Ile Asn Asp Glu Pro Pro Lys Ala Gln Val Ile Gly Trp
1               5                   10                  15

Pro Pro Val Arg Ser Tyr Arg Lys Asn Ile Leu Glu Ala Ser Tyr Val
            20                  25                  30

Lys Val Ser Met Asp Gly Ala Ala Tyr Leu Arg Lys Ile Asp Leu Asn
            35                  40                  45

Ile Tyr Lys Ser Tyr Pro Gln Leu Leu Lys Ala Leu Glu Asn Met Phe
50                  55                  60

Lys Cys Ser Ile Glu Thr
65                  70
```

<210> SEQ ID NO 51
<211> LENGTH: 167
<212> TYPE: PRT
<213> ORGANISM: Helianthus annuus

<400> SEQUENCE: 51

```
Met Ser Thr Glu Asp Gln Phe Gly Leu Glu Ile Thr Glu Leu Arg Leu
1               5                   10                  15

Gly Leu Pro Gly Gly Gly Glu Arg Asn Val Lys Lys Arg Val Phe Leu
            20                  25                  30

Asp Ile Leu Gly Gly Gly Asp Glu Val Asp Leu Cys Gly Asn Gly Gly
            35                  40                  45

Gly Lys Asn Arg Asn Met Glu Val Ala Val Gly Trp Pro Pro Val Cys
50                  55                  60
```

```
Ser Tyr Arg Lys Arg Thr Ile Ile Lys Met Tyr Val Lys Val Ser Met
 65                  70                  75                  80

Asp Gly Ala Pro Phe Leu Arg Lys Ile Asp Ile Asn Gly Phe Lys Gly
                 85                  90                  95

Tyr Ser Asp Phe Val Met Ala Leu Glu Lys Leu Phe Gly Leu Gly Asp
            100                 105                 110

Glu Cys Glu Tyr Ile Pro Ile Tyr Glu Asp Asn Asn Gly Asp Trp Met
            115                 120                 125

Leu Val Gly Phe Val Pro Trp Glu Ile Phe Thr Thr Cys Lys Arg
            130                 135                 140

Leu Arg Met Lys Lys Val Leu Asp Gly Gly Leu Gln Thr Lys Asn
145                 150                 155                 160

Leu Met Arg Lys Asn Glu Asn
                165

<210> SEQ ID NO 52
<211> LENGTH: 410
<212> TYPE: PRT
<213> ORGANISM: Vitis vinifera

<400> SEQUENCE: 52

Met Glu Asn Leu Gly Leu Leu Gly Ala Gln Thr Gly Tyr Lys Gly Ile
  1               5                  10                  15

Gly Val Leu Phe Asn Val Met Ser Pro Pro Leu Leu Gly Val Gly Glu
                 20                  25                  30

Glu Glu Gly Gln Ser Asn Val Thr Ile Leu Ala Ser Ser Ala Ser Met
             35                  40                  45

Glu Ser Val Cys Gln Ile Ser Ser Gly Leu Lys Glu Arg Asn Tyr Met
 50                  55                  60

Gly Leu Ser Glu Cys Ser Ser Val Asp Ser Ser Ala Ile Ser Thr Asp
 65                  70                  75                  80

Ser Asp Gly Asn Lys Ser Ser Leu Asn Leu Lys Ala Thr Glu Leu Arg
                 85                  90                  95

Leu Gly Leu Pro Gly Ser Leu Ser Pro Gly Arg Glu Pro Glu Leu Cys
            100                 105                 110

Leu Leu Ser Ser Thr Lys Leu Asp Glu Lys Pro Leu Phe Pro Leu His
            115                 120                 125

Pro Ser Lys Asp Leu Thr Tyr Thr Ser Ser Gln Lys Thr Val Val Ser
            130                 135                 140

Gly Asn Lys Arg Gly Phe Ala Asp Ala Met Asn Gly Phe Ser Glu Gly
145                 150                 155                 160

Lys Phe Leu Ala Asn Ser Glu Val Asn Val Met Leu Ser Pro Arg Pro
                165                 170                 175

Ser Pro Asn Lys Glu Asn Leu Gly Ser Gln Pro Ala Lys Met Lys Glu
            180                 185                 190

Met Ala Ser Pro Lys Ile Val Gln Glu Arg Pro Arg Ala Thr Asn Glu
            195                 200                 205

Thr Pro Pro Asn His Thr Gly Thr Gly Asn Asn Asn Ser Ser Ala Pro
            210                 215                 220

Ala Thr Lys Ala Gln Val Val Gly Trp Pro Pro Ile Arg Ser Phe Arg
225                 230                 235                 240

Lys Asn Thr Leu Ala Thr Thr Ser Lys Asn Thr Glu Val Asp Gly Lys
                245                 250                 255

Ala Gly Pro Gly Ala Leu Phe Val Lys Val Ser Met Asp Gly Ala Pro
            260                 265                 270
```

```
Tyr Leu Arg Lys Val Asp Leu Arg Asn Tyr Ser Ala Tyr Gln Glu Leu
            275                 280                 285

Ser Ser Ala Leu Glu Lys Met Phe Ser Cys Phe Thr Ile Gly Gln Tyr
290                 295                 300

Gly Ser His Gly Ala Pro Gly Arg Glu Met Leu Ser Glu Ser Lys Leu
305                 310                 315                 320

Lys Asp Leu Leu His Gly Ser Glu Tyr Val Leu Thr Tyr Glu Asp Lys
                325                 330                 335

Asp Gly Asp Trp Met Leu Val Gly Asp Val Pro Trp Gln Met Phe Ile
                340                 345                 350

Glu Thr Cys Lys Arg Leu Arg Ile Met Lys Ser Cys Asp Ala Ile Gly
                355                 360                 365

Leu Gly Leu Trp Arg Asn Ala Arg Thr Gly Thr Ser Leu Pro Leu His
            370                 375                 380

Met Val Val Ala Ile His Pro Ala Gly Leu Gly Glu Gly Gly Asn Ala
385                 390                 395                 400

Lys Ala Arg Phe Trp Trp Lys Cys Arg Asn
                405                 410

<210> SEQ ID NO 53
<211> LENGTH: 331
<212> TYPE: PRT
<213> ORGANISM: Glycine max

<400> SEQUENCE: 53

Met Gln Pro Gln Ala Gln Val Pro Gln Ser Tyr Ile Ile Glu Gly Tyr
1               5                   10                  15

His Thr His Ser Leu Ser Leu Val Ile Tyr Ile Ala Lys Gln Thr Lys
                20                  25                  30

Gln His Tyr Asn Arg Lys Arg Thr Gln Ser Glu Arg Glu Gly Ser Tyr
            35                  40                  45

Ser His Lys Glu Lys Asn Phe Gln Arg Gly Glu Ser Lys Arg Val Leu
        50                  55                  60

Leu Phe Leu Phe Tyr Ile Tyr Leu Gly Ala Lys Leu Cys Glu Phe Ile
65                  70                  75                  80

Asp Lys Pro Glu Met Ala Thr Met Leu Thr Lys Glu His Gly Leu Asn
                85                  90                  95

Leu Lys Glu Thr Glu Leu Cys Leu Gly Leu Pro Gly Gly Gly Gly Gly
            100                 105                 110

Gly Gly Gly Gly Gly Gly Gly Gly Glu Val Glu Thr Pro Arg
            115                 120                 125

Ala Thr Gly Lys Arg Gly Phe Ser Glu Thr Val Asp Leu Lys Leu Asn
130                 135                 140

Leu His Ser Lys Glu Asp Leu Asn Glu Asn Leu Lys Asn Val Ser Lys
145                 150                 155                 160

Glu Lys Thr Leu Leu Lys Asp Pro Ala Lys Pro Ala Lys Ala Gln
                165                 170                 175

Val Val Gly Trp Pro Pro Val Arg Ser Tyr Arg Lys Asn Met Met Ala
            180                 185                 190

Val Gln Lys Val Ser Thr Glu Asp Val Ala Glu Lys Thr Thr Ser Ser
        195                 200                 205

Thr Ala Asn Pro Gly Ala Phe Val Lys Val Ser Met Asp Gly Ala Pro
    210                 215                 220

Tyr Leu Arg Lys Val Asp Leu Thr Met Tyr Lys Ser Tyr Lys Glu Leu
```

```
                225                 230                 235                 240
Ser Asp Ala Leu Ala Lys Met Phe Ser Phe Thr Met Gly Asn Tyr
                    245                 250                 255

Gly Ala Gln Gly Met Ile Asp Phe Met Asn Glu Ser Lys Leu Met Asp
                    260                 265                 270

Leu Leu Asn Ser Ser Glu Tyr Val Pro Ser Tyr Glu Lys Asp Gly
                275                 280                 285

Asp Trp Met Leu Val Gly Asp Val Pro Trp Glu Met Phe Val Glu Ser
    290                 295                 300

Cys Lys Arg Leu Arg Ile Met Lys Gly Ser Glu Ala Ile Gly Leu Ala
305                 310                 315                 320

Pro Arg Ala Met Glu Lys Cys Lys Ser Arg Ser
                325                 330

<210> SEQ ID NO 54
<211> LENGTH: 337
<212> TYPE: PRT
<213> ORGANISM: Coffea canephora

<400> SEQUENCE: 54

Met Ser Met Pro Phe Glu Glu His Asp Tyr Ile Gly Leu Ser Glu Val
1               5                   10                  15

Pro Ala Met Glu Asn Ser Glu Lys Asn Asn Gly Leu Pro Leu Gly Asp
                20                  25                  30

Asn Glu Lys Lys Asn Thr Ala Lys Val Leu Asn Leu Lys Ala Thr Glu
            35                  40                  45

Leu Arg Leu Gly Leu Pro Gly Ser Glu Ser Pro Glu Arg Glu Thr Gly
50                  55                  60

His Gly Glu Asp Lys Asn Gly Tyr Gln Leu Gly Val Leu Lys Gly
65                  70                  75                  80

Phe Val Ser Gly Ala Lys Arg Gly Phe Ser Asp Thr Ile Asn Gly Gly
                85                  90                  95

Ser Gly Lys Trp Val Tyr Ser Gly Ser Gly Ser Glu Val Asn Leu
            100                 105                 110

Ala Asn Gly Gly Leu Phe Ser Pro Arg Gly Ala Asn Gly Ala Ala
            115                 120                 125

Lys Ser Ile Gly Ala Gly Gly Val Asp Ser Ala Ser Gln Gln Thr Phe
    130                 135                 140

Val Gly Ser Gly Val Gly Lys Glu Thr Val Pro Gln Ser Pro Lys Pro
145                 150                 155                 160

Val Gln Glu Lys Lys Pro Gln Val Ser Ala Ala Asn Gly His Ala Ala
                165                 170                 175

Ala Pro Ala Ala Lys Ala Gln Val Gly Trp Pro Pro Ile Arg Ser
            180                 185                 190

Phe Arg Lys Asn Ser Met Ala Ile Asn Pro Pro Lys Thr Asp Glu Asp
            195                 200                 205

Ala Asp Ala Lys Leu Gly Thr Gly Cys Leu Tyr Val Lys Val Ser Met
    210                 215                 220

Asp Gly Ala Pro Tyr Leu Arg Lys Val Asp Ile Lys Ile Tyr Ser Ser
225                 230                 235                 240

Tyr Lys Asp Leu Ser Ser Ala Leu Glu Lys Met Phe Ser Cys Phe Thr
                245                 250                 255

Ile Gly Gln Cys Gly Ser His Gly Val His Ile Arg Asp Gly Met Ser
            260                 265                 270
```

```
Glu Ser Arg Leu Met Asp Leu Leu His Gly Ser Glu Tyr Val Leu Thr
            275                 280                 285

Tyr Glu Asp Lys Asp Gly Asp Trp Met Leu Val Gly Asp Val Pro Trp
        290                 295                 300

Glu Met Phe Met Asp Ser Cys Lys Arg Leu Arg Ile Met Lys Ser Ser
305                 310                 315                 320

Asp Ala Ile Gly Leu Ala Pro Arg Ala Met Glu Lys Cys Lys Asn Arg
                325                 330                 335

Asn

<210> SEQ ID NO 55
<211> LENGTH: 134
<212> TYPE: PRT
<213> ORGANISM: Gossypium raimondii

<400> SEQUENCE: 55

Met Glu Gly Ser Val Gly Tyr Asp Asn Asp Leu Asn Leu Lys Ala Thr
1               5                   10                  15

Glu Leu Arg Leu Gly Leu Pro Gly Thr Glu Pro Val Ser Ile Val Arg
            20                  25                  30

Arg Asn Lys Arg Ser Leu Gln Gln Val Ala Asp Asp Cys Gly Val
        35                  40                  45

Asn Gly Cys Lys Ser Asp Asp Gln Asn Glu Thr Ala Pro Pro Pro
    50                  55                  60

Lys Ala Gln Ile Val Gly Trp Pro Pro Ile Arg Ser Tyr Arg Lys Asn
65                  70                  75                  80

Asn Ile Gln Thr Lys Lys Asn Glu Ser Glu Gly Gly Ile Tyr Val
            85                  90                  95

Lys Val Ser Met Asp Gly Ala Pro Tyr Leu Arg Lys Ile Asp Leu Lys
                100                 105                 110

Val Tyr Ser Gly Tyr Pro Glu Leu Leu Gln Ala Ile Glu Asn Met Phe
            115                 120                 125

Lys Phe Thr Ile Val Leu
    130

<210> SEQ ID NO 56
<211> LENGTH: 193
<212> TYPE: PRT
<213> ORGANISM: Phaseolus vulgaris

<400> SEQUENCE: 56

Met Glu Asn Thr Val Thr Tyr Ala Thr Asp Leu Asn Leu Lys Ala Thr
1               5                   10                  15

Glu Leu Arg Leu Gly Leu Pro Gly Thr Glu Glu Ser Glu Gly Lys Thr
            20                  25                  30

Leu Pro Ala Ala Val Arg Ile Thr Asn Lys Arg Pro Leu Asn Glu Thr
        35                  40                  45

Ser Glu Glu Thr Leu Ser Lys Gly Ser Asn Ala Pro Lys Thr Val Gln
    50                  55                  60

Thr Glu Ala Ala Pro Ala Lys Ala Lys Ile Val Gly Trp Pro Pro
65                  70                  75                  80

Ile Arg Ser Tyr Arg Lys Asn Ser Leu Gln Glu Asn Glu Gly Ala Gly
            85                  90                  95

Ile Tyr Val Lys Val Ser Met Asp Gly Ala Pro Tyr Leu Arg Lys Ile
                100                 105                 110

Asp Leu Lys Val Tyr Gly Gly Tyr Thr Gln Leu Leu Ile Ala Leu Glu
```

```
                115                 120                 125
Thr Met Phe Lys Leu Thr Ile Gly Glu Tyr Ser Glu Lys Glu Gly Tyr
    130                 135                 140

Lys Gly Ser Asp Tyr Ala Pro Thr Tyr Glu Asp Lys Asp Gly Asp Trp
145                 150                 155                 160

Met Leu Val Gly Asp Val Pro Trp Asp Met Phe Val Thr Ser Cys Lys
                165                 170                 175

Arg Leu Arg Ile Met Lys Gly Ser Glu Ala Arg Gly Leu Gly Cys Gly
            180                 185                 190

Val

<210> SEQ ID NO 57
<211> LENGTH: 198
<212> TYPE: PRT
<213> ORGANISM: Beta vulgaris

<400> SEQUENCE: 57

Met Ala Arg Ser Glu Thr Tyr Glu Asn Asp Leu His Leu Glu Ala Thr
1               5                   10                  15

Glu Leu Arg Leu Gly Leu Pro Gly Ser Lys Glu Pro Glu Lys Gln Ser
            20                  25                  30

Thr Ser Asn Asn Val Val Arg Ser Asn Lys Arg Ser Ser Pro Asp Gln
        35                  40                  45

Leu Leu Glu Asp Ser Ser Ser Thr Asn Asn Ser Ser Val Ser Asp Ala
    50                  55                  60

Arg Asn Glu Asp Cys Pro Pro Ser Lys Thr Gln Ile Val Gly Trp
65              70                  75                  80

Pro Pro Ile Arg Ser Tyr Arg Lys Asn Asn Leu Gln Pro Lys Lys Thr
                85                  90                  95

Glu Thr Asp Ala Ser Gly Met Tyr Val Lys Val Ser Met Asp Gly Ala
            100                 105                 110

Pro Tyr Leu Arg Lys Ile Asp Leu Lys Met Tyr Gln Ser Tyr Ala Glu
        115                 120                 125

Leu Leu Lys Gly Leu Glu Ser Met Phe Arg Ile Cys Ile Gly Lys Tyr
    130                 135                 140

Ser Glu Arg Asp Gly Tyr Asn Gly Ser Asp Val Ala Pro Thr Tyr Glu
145                 150                 155                 160

Asp Lys Asp Gly Asp Trp Met Leu Val Gly Asp Val Pro Trp Glu Met
                165                 170                 175

Phe Ile Thr Ser Cys Lys Arg Leu Arg Ile Met Lys Ser Ser Glu Ala
            180                 185                 190

Lys Gly Leu Gly Cys Leu
        195

<210> SEQ ID NO 58
<211> LENGTH: 160
<212> TYPE: PRT
<213> ORGANISM: Capsicum annuum

<400> SEQUENCE: 58

Met Glu Met Ala Gly Thr Glu Leu Arg Leu Gly Leu Pro Gly Thr Asp
1               5                   10                  15

Ser Ser Ser Ser Ala Ser Lys Ile Thr Asn Lys Arg Pro Ser Ser
            20                  25                  30

Asp Met Ile Asn Ser Asn Asp Asp Glu Pro Ala Pro Lys Ala Gln Val
        35                  40                  45
```

Val Gly Trp Pro Pro Val Arg Ser Tyr Arg Lys Asn Val Leu Gln Ala
    50                  55                  60

Ser Tyr Val Lys Val Ser Met Asp Gly Ala Ala Tyr Leu Arg Lys Ile
65                  70                  75                  80

Asn Leu Asn Val Tyr Lys Ser Tyr Pro Gln Leu Leu Lys Ala Leu Asp
                85                  90                  95

Asn Met Phe Lys Cys Ser Ile Gly Val Tyr Ser Glu Arg Glu Gly Tyr
            100                 105                 110

Asn Gly Cys Asp Tyr Val Ala Thr Tyr Glu Asp Lys Asp Gly Asp Trp
            115                 120                 125

Met Leu Ala Gly Asp Val Pro Trp Asp Met Phe Ile Asn Ser Cys Arg
            130                 135                 140

Arg Leu Arg Ile Met Lys Gly Ser Glu Ala Lys Gly Leu Ala Cys Leu
145                 150                 155                 160

<210> SEQ ID NO 59
<211> LENGTH: 156
<212> TYPE: PRT
<213> ORGANISM: Solanum lycopersicum

<400> SEQUENCE: 59

Met Glu Met Ala Gly Thr Glu Leu Arg Leu Gly Leu Pro Gly Thr Val
1               5                   10                  15

Pro Ser Ser Thr Ser Lys Ile Ser Asn Lys Arg Cys Ser Ser His Arg
                20                  25                  30

Asn Asn Asn Asp Glu Pro Pro Gln Lys Ala Gln Val Val Gly Trp Pro
            35                  40                  45

Pro Val Arg Ser Tyr Arg Lys Asn Ile Leu Glu Ala Ser Tyr Val Lys
    50                  55                  60

Val Ser Met Asp Gly Ala Ala Tyr Leu Arg Lys Ile Asp Leu Asn Thr
65                  70                  75                  80

Tyr Lys Ser Tyr Pro Gln Leu Leu Lys Ala Leu Glu Asn Met Phe Lys
                85                  90                  95

Cys Ser Ile Asp Val Tyr Ser Glu Thr Asp Gly Tyr Asn Gly Cys Asn
            100                 105                 110

Tyr Ile Pro Thr Tyr Glu Asp Lys Asp Gly Asp Trp Met Leu Ala Gly
            115                 120                 125

Asp Val Pro Trp Asp Met Phe Ile Asn Ser Cys Lys Arg Leu Arg Ile
            130                 135                 140

Met Lys Gly Ser Glu Ala Lys Gly Leu Ala Ser Leu
145                 150                 155

<210> SEQ ID NO 60
<211> LENGTH: 153
<212> TYPE: PRT
<213> ORGANISM: Solanum tuberosum

<400> SEQUENCE: 60

Met Glu Met Ala Gly Thr Glu Leu Arg Leu Gly Leu Pro Gly Thr Glu
1               5                   10                  15

Pro Ser Ser Thr Ser Thr Ser Lys Ile Ser Asn Lys Arg Pro Ser
                20                  25                  30

Ser His Ile Asn Asp Glu Pro Pro Lys Ala Gln Val Ile Gly Trp
            35                  40                  45

Pro Pro Val Arg Ser Tyr Arg Lys Asn Ile Leu Glu Ala Ser Tyr Val
    50                  55                  60

```
Lys Val Ser Met Asp Gly Ala Ala Tyr Leu Arg Lys Ile Asp Leu Asn
 65                  70                  75                  80

Ile Tyr Lys Ser Tyr Pro Gln Leu Leu Lys Ala Leu Glu Asn Met Phe
                 85                  90                  95

Lys Cys Ser Ile Glu Thr Glu Gly Tyr Asn Gly Cys Asn Tyr Val Pro
            100                 105                 110

Thr Tyr Glu Asp Lys Asp Gly Asp Trp Met Leu Ala Gly Asp Val Pro
        115                 120                 125

Trp Asp Met Phe Ile Asn Ser Cys Lys Arg Leu Arg Ile Met Lys Gly
    130                 135                 140

Ser Glu Ala Lys Gly Leu Ala Ser Leu
145                 150

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
aactcaaatc gttggttggc                                              20

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
ctttatcctc gtacgttggt acg                                          23

<210> SEQ ID NO 63
<211> LENGTH: 41
<212> TYPE: DNA
<213> ORGANISM: Artificial Sequence
<220> FEATURE:
<223> OTHER INFORMATION: Primer

<400> SEQUENCE: 63
gaaggtcgga gtcaacggat tctccggtga gatcttatgt g                      41

<210> SEQ ID NO 64
<211> LENGTH: 45
<212> TYPE: DNA
<213> ORGANISM: Artificial Sequence
<220> FEATURE:
<223> OTHER INFORMATION: Primer

<400> SEQUENCE: 64
gaaggtgacc aagttcatgc tcgtaagaac aacaacagtg tgagc                  45

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
attttgcgga ggtatggtgc                                              20
```

```
<210> SEQ ID NO 66
<211> LENGTH: 38
<212> TYPE: DNA
<213> ORGANISM: Artificial Sequence
<220> FEATURE:
<223> OTHER INFORMATION: Primer

<400> SEQUENCE: 66
ttggcgcgcc atggcgtacg agaaagtcaa tgagctta                    38

<210> SEQ ID NO 67
<211> LENGTH: 43
<212> TYPE: DNA
<213> ORGANISM: Artificial Sequence
<220> FEATURE:
<223> OTHER INFORMATION: Primer

<400> SEQUENCE: 67
cgggatcctc ataaggaaga gtcatcagat cctttcatga ttc              43

<210> SEQ ID NO 68
<211> LENGTH: 23
<212> TYPE: DNA
<213> ORGANISM: Artificial Sequence
<220> FEATURE:
<223> OTHER INFORMATION: Primer

<400> SEQUENCE: 68
gaacaacaac agtgtgagct atg                                    23

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
gccttgagaa gctctggata g                                      21

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
ctccggtgag atcttatgtg                                        20

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
ctccggtgag atcttatgtg                                        20

<210> SEQ ID NO 72
<211> LENGTH: 20
<212> TYPE: DNA
<213> ORGANISM: Artificial Sequence
<220> FEATURE:
<223> OTHER INFORMATION: Primer
```

```
<400> SEQUENCE: 72
catgtgccaa ggaggagatt                                              20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
gtgtgcttcc tctcgaagtt                                              20

<210> SEQ ID NO 74
<211> LENGTH: 22
<212> TYPE: DNA
<213> ORGANISM: Artificial Sequence
<220> FEATURE:
<223> OTHER INFORMATION: Primer

<400> SEQUENCE: 74
gtggaaccac tatgttctct gg                                           22

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
ggaggtgcaa cgaccttaat                                              20
```

HERBICIDE TOLERANT PLANTS AND PRODUCTION AND DETECTION OF SAME

CROSS REFERENCE TO RELATED APPLICATIONS

This application is a U.S. National application which claims priority from PCT/US20/22118, filed Mar. 11, 2020 which claims priority to previously filed and co-pending applications U.S. Ser. No. 62/816,773 filed Mar. 11, 2019 and to U.S. Ser. No. 62/963,630, filed Jan. 21, 2020, the contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 10, 2020, is named P13033US02 SEQ LISTING_ST25.txt and is 94,245 bytes in size.

FIELD OF THE INVENTION

The present invention relates in general to compositions and methods for conferring plants with tolerance to herbicides. Particularly, the invention refers to plants that have a deleted or disrupted degron tail region of the IAA2 protein and having an increased tolerance to herbicides, more specifically to synthetic auxin herbicides.

BACKGROUND

Auxin, mainly as indoleacetic acid (IAA), is an important plant hormone essential for plant growth and development. It also plays a key role in the response of plants to changes in their environment. Auxins precipitate in a cascade of reactions, the best described of which is the transport inhibitor response 1 (TIR1)/auxin-binding F-box (AFB) TIR1/AFB-auxin-Aux/IAA co-receptor system that is part of the Skp1-cullin-F-box protein (SCF) E3 ubiquitin ligase complex. Auxin interacts with both TIR1/AFB and the transcriptional repressor protein Aux/IAA. This leads to ubiquitination of the Aux/IAA protein, signaling the 26s proteasome to degrade the Aux/IAA protein resulting in de-repression of auxin response factors (ARFs) and transcription of auxin-regulated genes.

A number of synthetic auxins are used as commercial herbicides, with 2,4-D first being used in 1945. These herbicides belong to several chemical families and can have varying efficacy across plant species. The herbicides bind to the TIR1 receptor and the Aux/IAA repressor as auxin does; however, with herbicides the response leads to hyperaccumulation of ethylene, abscisic acid (ABA), and the production of reactive oxygen species (ROS). The events cause stomatal closure, uncontrolled cell differentiation, and elongation visible through swelling, epinasty, leaf withering, and ultimately senescence.

The intensive use of synthetic auxin herbicides has resulted in the evolution of herbicide resistance in the target weeds. To date, 39 weed species have populations that have evolved resistance to one or more synthetic auxin herbicides. Two different mechanisms have been identified to synthetic auxin herbicides: enhanced herbicide metabolism and reduced translocation of the herbicide from the treated leaves.

Herbicide tolerant plants are useful in systems in which a plurality of such plants are planted, and can produce a crop, and either prior to planting, or after planting, an herbicide is applied that would otherwise kill or harm the plants but for their tolerance to the herbicide. Undesirable plants are killed or damaged, and the tolerant plants survive. There is a need to produce such plants.

SUMMARY

Applicants have surprisingly found that deletion or disruption of the degron tail region an Indole-3-Acetic Acid Inducible (IAA) protein can confer tolerance to herbicides in plants. This novel mutation can be used to generate crops resistant to herbicides, including 2,4-D. Accordingly, the present invention provides for compositions and methods for producing plants that are resistant to herbicides.

The present invention provides plants having increased tolerance to herbicides when compared to a wild-type plant. In particular, the plants of the invention have increased resistance to synthetic auxin herbicides when compared to a wild-type plant. The herbicide-resistant plants of the invention comprise a polynucleotide that encodes an herbicide tolerant IAA protein, preferably IAA2. Such an herbicide tolerant IAA protein comprises a deletion or disruption of the degron tail region. The plants of the invention also include seeds and progeny plants that comprise a polynucleotide encoding an herbicide tolerant IAA protein of the invention.

Using the methods and materials of the present invention, herbicide tolerance may be conferred to a plant by, for example, introducing a heterologous nucleic acid of the present invention or by introducing a mutation or deletion of one or more amino acids of the degron tail region of an IAA protein through the use of a gene editing technique.

In another embodiment, the invention refers to methods for controlling undesired vegetation at a plant cultivation site. The methods comprise the steps of providing, at the site, a plant according to the present invention having a deleted or disrupted degron tail region of an IAA protein which is tolerant to an herbicide and applying to the site an effective amount of the herbicide.

In yet another embodiment, the present invention provides methods for identifying plant lines tolerant to the described herbicides and having a deleted or disrupted degron tail region of an IAA protein. The methods comprise the steps of obtaining a sample from the plant and assaying the plant for the absence or disruption of expression of a nucleic acid molecule encoding the degron tail or the deletion or disruption of the degron tail. The sequence information disclosed herein can be used in resistance diagnostics, including PCR assays and/or protein antibody assays. In another embodiment, kits comprising a primer or probe that detects the presence or absence or disruption of a degron tail region of an IAA protein are provided.

The present invention provides a substantially purified or isolated nucleic acid or nucleic acid fragment encoding an herbicide tolerant IAA protein, complements thereof, and functionally active fragments and variants thereof. The nucleic acid encoding an herbicide tolerant IAA includes those selected from the group consisting of: (a) the sequence shown in SEQ ID NO: 4; (b) a nucleotide sequence encoding the polypeptide shown in SEQ ID NO: 3; (c) complements of the sequences recited in (a) and (b); (d) functionally active fragments of the sequences recited in (a), (b), and (c); and (e) functionally active variants of the sequences recited in (a), (b), (c), and (d). The nucleic acids encode an herbicide tolerant IAA protein comprising a deletion or disruption of the degron tail region as described herein.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1 shows the amino acid sequence of the *Sisymbrium orientale* IAA2 protein with the degron conserved core motif shown in bold (SEQ ID NO: 1).

FIGS. 2A-E show protein sequence alignments of herbicide sensitive (IAA2_full_protein_S, SEQ ID NO: 1) and resistant (IAA2_deletion_protein_R, SEQ ID NO: 3) *Sisymbrium orientale* IAA2 to Brassicaceae species with high similarity to IAA2 (from top to bottom, starting with KFK39590.1 and ending with XP_006406101.1. SEQ ID NOs: 6-38). The conserved degron is noted as indicated with a box as is the degron tail.

FIG. 3 shows a protein sequence alignment of the region comprising the IAA2 degron and degron tail including *Sisymbrium orientale* and 10 other species (from top to bottom, starting with sunflower-HannXRQ_Chr10g0314921 and ending with potato_PGSC0003DMG400020139, SEQ ID NOs: 39-50). Full length sequences of the IAA proteins from the 10 species are shown in SEQ ID NOs: 51-60.

DETAILED DESCRIPTION

Figure 4:
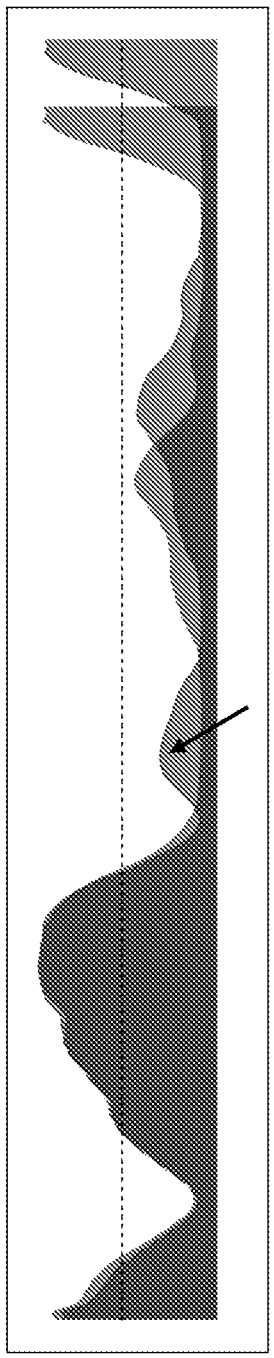
FIG. 4 is a chart representing prediction of disordered protein regions based upon local amino acid sequence information and template proteins. Red is mIAA2 and blue is the wild-type template.

Resistance to 2,4-D in *Sisymbrium orientale* was reported in South Australia in 2005. *S. orientale* is the sixth most costly weed of crops in southern Australia and is most problematic on alkaline soils. Resistance to 2,4-D has occurred in several populations of *S. orientale* in South Australia. This resistance is inherited as a single dominant allele and results in significantly less 2,4-D translocating from the treated leaves to other parts of the plant compared to susceptible plants. A deletion of nine highly conserved amino acids after the degron of the auxin co-receptor IAA2 gene has been identified as a source of reduced translocation of 2,4-D in this species.

Indole-3-Acetic Acid proteins (IAA) are transcriptional repressors, the expression of which is stimulated by the phytohormone auxin. In the presence of a threshold concentration of auxin, the system triggers degradation of the protein. There are 29 gene family member that have been isolated in *Arabidopsis* and 55 from *Brassica*. *Brassica rapa* Aux/IAA family genes are discussed at length in Paul et al. (2016) "Genome-wide analysis and characterization of Aux/ IAA family genes in *Brassica rapa*" PLoS One 6; 11(4).

Degradation signals or degrons are a region of a protein that is involved in regulation of the rate of degradation of protein. It is a minimal element within a protein that is sufficient for targeting the protein for degradation. Degrons may lead to a change in more or less ubiquitination and may be categorized as ubiquitin dependent or may be ubiquitin independent and the presence of the degron is not necessary for polyubiquitination of the protein. A degron may be identified by measuring the increase or decrease in amount of a protein when the region is present or absent.

Aux/IAA genes encode 25 to 35 kD proteins localized to the nuclease. The proteins have four conserved domains, domains I, II, III and IV. Domain II plays a role in destabilizing IAA proteins. The domain has the residues necessary for the receptor, auxin and co-receptor complex modulating the rate of Aux/IAA turnover and contain the degron that is necessary and sufficient for auxin-induced degradation. See Leyser et al. (2018) "Auxin Signaling" *Plant*

*Physiol.* 176(1):465-479 and Zenser et al. (2001) "Auxin modulates the degradation rate of Aux/IAA proteins" *Proc. Natl. Acad. Sci USA* 98(20):11795-11800.

The degron has a conserved core GWPPV motif which is a binding site with TIR/AFB proteins and auxin. The auxin-responsive IAA2 protein of *Sisymbrium orientale* is shown in SEQ ID NO: 1:

```
MAYEKVNELNLKDTELRLGLPGTEQVKEEQEVSCVRSNKRQFQIDNEEN

REEEESTPPTKTQIVGWPPVRSYRKNNNSVSYVKVSMDGAPYLRKIDLK

TYKNYPELLKALENMFKFTVGEYCEREGYKGSEVVPTYEDKDGDWMLVG

DVPWDMFSSSCKRLRIMKGSDDSSL
```

The degron conserved GWPPV motif is identified in bold in FIG. 1.
The IAA2 protein of *Sisymbrium orientale* is encoded by the nucleotide sequence of SEQ ID NO: 2:

```
ATGGCGTACGAGAAAGTCAATGAGCTTAACCTTAAGGACACAGAGCTTC

GTCTTGGATTACCTGGAACAGAGCAAGTTAAAGAAGAACAAGAGGTTTC

TTGCGTTAGAAGCAACAAGCGTCAATTCCAAATCGATAACGAGGAAAAC

CGTGAGGAAGAAGAATCTACACCTCCTACGAAAACTCAAATCGTTGGTT

GGCCTCCGGTGAGATCTTACCGTAAGAACAACAACAGTGTGAGCTATGT

GAAAGTGAGTATGGACGGAGCACCATACCTCCGCAAAATCGATCTCAAA

ACATACAAAAACTATCCAGAGCTTCTCAAGGCGTTAGAAAACATGTTCA

AGTTCACGGTAGGTGAGTACTGTGAAAGAGAAGGATACAAAGGATCTGA

AGTCGTACCAACGTACGAGGATAAAGATGGAGACTGGATGTTGGTTGGT

GATGTTCCATGGGATATGTTCTCATCCTCTTGTAAGAGACTCAGAATCA

TGAAAGGATCTGATGACTCTTCCTTATGA
```

The disordered region following the degron is known as the "degron tail". The degron may be readily identified as described above. In any particular species of plant, the IAA region II degron may be identified and in an embodiment may be identified by alignment with the IAA2 *Sisymbrium orientale* sequence identified here. The disordered region does not have a fixed or ordered three-dimensional structure. Such degron tails may be partially or completely disordered. See, e.g., Uversky, Vladimir N. (2011) Intrinsically disordered proteins from A to Z. http://doi.org/10.1016/j.biocel.2011.04.001. The degron tail described here has been found by the inventors to be highly disordered.

Bioinformatics can identify such disordered regions. For example, Liu et al. describe classification-based predictors of intrinsically disordered proteins (IDPs) and improves on these processes by describing a sequence labeling model based on conditional random fields. Their method uses IDP-FSP which uses three CRF-based predictors designed to predict long, short and generic disordered regions. See Liu et al. "Identification of Intrinsically Disordered Proteins and Regions by Length-Dependent Predictors Based on Conditional Random Fields" *Molecular Therapy Nucleic Acids* Vol. 17: 396-404. Various processes utilized involve machine learning techniques and computational predictors. Their method utilizes a predictor called IDP-FSP based on CRFs. IDP-FSP is a fusion of three CRF-based predictors— IDP-FSP-L, IDP-FSP-S, and IDP-FSP-G—that are specifically designed to predict long, short, and generic disordered regions, respectively.

Figure 2C:
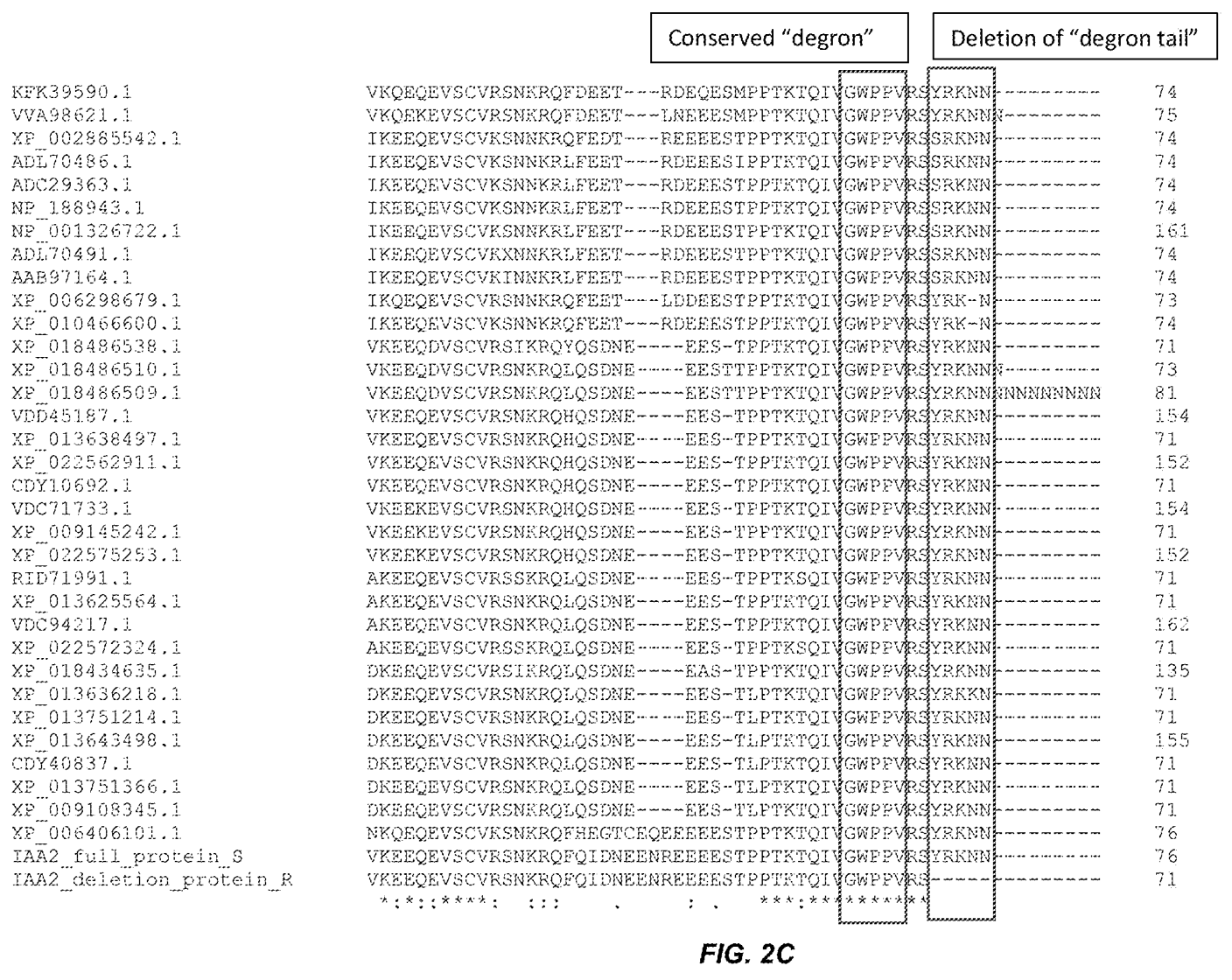

By way of example, here is found that a deletion of the nine amino acid region of the degron tail of the IAA2 protein confers resistance to herbicides. The amino acid sequence deleted is shown in the protein alignment of IAA2 in FIG. 2. As can be seen the deleted amino acids within this degron tail comprise YRKNNNSVS (SEQ ID NO: 5). FIG. 3 shows alignment of BLASTP hits for the region comprising the IAA2 degron and degron tail to 10 species; all other species have sequence in between domain II and III (each highly conserved); the sequence is divergent, but no species have less sequence than IAA2 in the way that the deletion allele has the disordered amino acids missing.

The experimentation here checked how disordered the deletion region is (known as the 'degron tail' for its proximity to the degron in domain II) and found that this region, found in the wild-type IAA2, is highly disordered. Losing this 'flexible intrinsically disordered' region reduces the flexibility of the protein to change its conformation when binding to an herbicide such as 2,4-D. The disassociation rate is faster for this mutant. Therefore, deleting this region affects the binding kinetics with herbicides such as 2,4-D. Less of the protein will be degraded after herbicide application, or not as quickly, preventing in an example the rapid increase in gene expression of 2,4-D regulated genes normally caused by herbicide application.

FIG. 4 shows the disordered region in the degron tail of wild-type IAA2 (see the arrow). It was obtained using the server PrDOS predicting disordered regions by comparison with a template. (See, e.g., Ishida et al. (2007) "PrDOS: prediction of disordered protein regions from amino acid sequence" Nucleic Acids Res. 35:W460-W464. The red area is the plot of mIAA2, note that the disordered degron tail is absent.

Experimentation included running BLASTP using IAA2 protein sequence against entire NCBI sequence database; 33 peptides with sequence identity ≥80%; mostly plants from within Brassicaceae family. See Ramos et al. (2001) "Rapid degradation of auxin/indoleacetic acid proteins requires conserved amino acids of domain II and is proteasome dependent" *Plant Cell* DOI: 10.2307/3871512. IAA2 and FIG. 2 therein. This figure shows multiple sequence alignment of amino acids spanning conserved domain II, equivalent to amino acids 68 to 111 from IAA17, of 22 Aux/IAA proteins from *Arabidopsis* and two Aux/IAA proteins from pea. The shaded regions encompass amino acids outside of the conserved domain II, with the 13-amino acid consensus sequence noted at the bottom of the alignment. Invariant residues among all Aux/IAA proteins shown are underlined in the consensus sequence. Numbers below the 13-amino acid consensus sequences are reference points for mutants and variants tested.

The 'degron tail' is highly conserved among these sequences; a few variants have extra N (Asp) residues, but none are missing the 9 amino acids deleted in the mIAA2 sequence. The experiments also ran BLASTP using just degron and degron tail from IAA2 against 10 species in Ensembl Plants, ran alignment of these sequences; not necessarily the best IAA2 homologue from each species but the best hit based on the IAA2 degron and degron tail.

By way of example without limitation, deletion of the degron tail confers resistance to benzonitrile herbicides, cyclohexanedione herbicides, imidazolinone herbicides, phenoxy herbicides, sulfonylurea herbicides, triazine herbicides, 1-aminocyclopropane-1-carboxylic acid synthase-inhibiting herbicides, 4-hydroxyphenylpyruvate dioxygenase-inhibiting herbicides, acetolactate synthase-inhibiting herbicides, protoporphyrinogen oxidase-inhibiting herbicides, 2,4-dichlorophenoxyacetic acid (2,4-D), bromoxynil, dicamba, glufosinate, glyphosate, nicosulfuron, or quizalofop-p-ethyl. Preferably, the herbicide is a synthetic auxin herbicide. Synthetic auxin herbicides mimic the natural plant hormone and can inhibit cell division and growth. Synthetic auxin herbicides include phenoxy herbicides, benzoic acid herbicides, and carboxylic acid herbicides. In a preferred embodiment, deletion of the degron tail confers resistance to 2,4-D dichlorophenoxyacetic acid.

The inventors have determined a broad cross-resistance pattern of this mutation to other herbicides, in addition to 2,4-D as outlined below.

TABLE 1

| Herbicide | Resistant | Susceptible | Testing in progress |
|---|---|---|---|
| Dicamba | X | | |
| Clopyralid | X | | |
| 2,4-D | X | | |
| Quinclorac | | X | |
| Triclopyr | | X | |
| Picloram | | | X |
| Fluroxypyr | | | X |
| Rinskor (florpyrauxifen-benzyl) | X | | |
| MCPA | X | | |
| Dichlorprop | | | X |

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of an herbicide is an amount that is routinely used in agricultural production systems to kill weeds of interest. Such an amount is known to those of ordinary skill in the art. Herbicidal activity is exhibited by herbicides useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, the herbicide treatments can be applied PPI (Pre Plant Incorporated), PPSA (Post plant surface applied), PRE- or POST-emergent. Postemergent treatment typically occurs to relatively immature undesirable vegetation to achieve the maximum control of weeds.

An embodiment provides for a plant having such a deleted or disrupted degron tail as described herein. The plant is resistance to one or more herbicides as described above. The plant may be any plant species, whether monocotyledonous or dicotyledonous, including but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats (*Avena* spp.), barley (*Hordeum* spp.), vegetables, ornamentals, and conifers. Vegetables include tomatoes (*Solanum lycopersicum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contotta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, the plant is a dicotyledonous plant.

The term plant or plant material or plant part is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like.

The plants here also include progeny which comprise said deleted or disrupted degron tail.

By an "herbicide-tolerant" or "herbicide-resistant" plant, it is intended that a plant that is tolerant or resistant to at least one herbicide at a level that would normally kill, or inhibit the growth of, a normal or wildtype plant. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope. As used herein, in regard to an herbicidal composition useful in various embodiments hereof, terms such as herbicides, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

Alterations to the 'degron tail' in one example alters the binding kinetics to 2,4-D and other synthetic auxin herbicides. Thus, introduction to a plant of the protein having the deleted degron tail, or otherwise causing any type of deletion or alteration via mutation of the region following the degron would confer herbicide resistance and in one example confers resistance to synthetic auxin herbicide resistance. This can be accomplished using transgenic approaches (the mutation is dominant), gene editing, and crossing with a plant not having the deleted degron tail.

In another embodiment, the present invention provides a method for controlling undesired vegetation at a plant cultivation site. The term "control of undesired vegetation or weeds" is to be understood as meaning the killing of weeds and/or otherwise retarding or inhibiting the normal growth of the weeds. Weeds, in the broadest sense, are understood as meaning all those plants which grow in locations where they are undesired. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

In yet another embodiment, the present invention provides a method for identifying plant lines tolerant to the described herbicides comprising supplying a sample from a plant, providing amplification primers for amplifying a region of a plant's genome corresponding to the nucleic acids encoding or the polypeptide of IAA2 with a deleted or disrupted degron tail present in said sample, applying said amplification primers to said nucleic acid sample such that amplification of a region that would comprise the degron tail, if present, and identifying plants tolerant to the herbicides based on the deletion or disruption of the degron tail in said sample and which confers herbicide tolerance. Such primers and probes are exemplified in the examples below. The methods here related to primers and probes with which to detect the presence or absence of the degron tail and/or its mutation. Such nucleic acids can have the sequence of at least 10, 12, 15, 20, 30, 40, 50 or more or less consecutive nucleotides of the region of IAA2 that would include the degron tail, such as SEQ ID NO: 2 from *Sisymbrium orientale*, by way of example. In an exemplary embodiment, the primers are selected from SEQ ID NOs: 61 and 62 or SEQ ID NOs: 63-65.

A kit may likewise be created that employs the use of such primers and/or probes. The presence of absence of the degron tail or its' mutation may be detected by sequencing, amplification and/or hybridization with a specific probe and primers as described here. A sample containing a nucleic acid may be obtained from the plant or plant part or cell. The primers or probes may be labelled using any technique known to those killed in the art. Examples include use of radioactive, fluorescent or enzymatic labelers. The nucleic acids may in embodiments be PCR amplified before detection. Methods are well known and in one example are described at Sambrook et al. *Molecular Cloning—A Laboratory Manual* Second Edition (Cold Spring Harbor Laboratory 1989).

Use of the absence or disruption of the degron tail as a marker for herbicide tolerance is available through the processes here. As used herein, the terms "marker" and "DNA marker" and "molecular marker" in reference to a "selectable marker" refers to a physiological or morphological trait that may be determined as a marker for its own selection or for selection of other traits closely linked to that marker. For example, such a marker could be a gene or trait that associates with herbicide tolerance including, but not limited to, simple sequence repeat (SSR), single nucleotide polymorphism (SNP), genetic insertions and/or deletions and the like.

The present processes provide a method of genotyping a plant comprising a polynucleotide of described here. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in plants (Ed., Andrew H. Paterson) by Academic Press/R.G. Lands Company, Austin, Tex., pp. 7-21.

The particular method of genotyping may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present methods, the nucleic acid probes employed for molecular marker mapping of plant nuclear genomes hybridize, under selective hybridization conditions, to a gene encoding a polynucleotide described here. In preferred embodiments, the probes are selected from polynucleotides of the present methods. Typically, these probes are cDNA probes or restriction enzyme treated genomic clones. The length of the probes is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome compliment. Some exemplary restriction enzymes employed in RFLP mapping are EcoRI, EcoRV, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present invention of the genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present processes further provide a method of genotyping comprising the steps of contacting, under stringent hybridization conditions, a sample suspected of comprising a polynucleotide of the present invention with a nucleic acid probe. Generally, the sample is a plant sample, preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

Other methods employed include use of KASP™, that is, Kompetitive Allele Specific PCR. It is based on competitive allele-specific PCR and allows scoring of single nucleotide polymorphisms (SNPs), as well as deletions and insertions at specific loci. Two allele specific forward primers are used having the target SNP at the 3' end and a common reverse primer is used for both. The primers have a unique "tail" sequence (reporter nucleotide sequence) compatible with a different fluorescent reporter (reporter molecule). The primers are contacted with the sample along with a mix which includes a universal Fluorescence Resonant Energy Transfer (FRET) cassette and Taq polymerase. During rounds of PCR cycling, the tail sequences allow the FRET cassette to bind to the DNA and emit fluorescence. See, e.g. Yan et al. "Introduction of high throughput and cost effective SNP genotyping platforms in soybean" *Plant Genetics, Genomic and Biotechnology* 2(1): 90-94 (2014); Semagn et al. "Single nucleotide polymorphism genotyping using Kompetitive Allele Specific PCR (KASP): overview of the technology and its application in crop improvement" *Molecular Breeding* 33(1): 1-14 (2013). In the present process, emission of one fluorescent signal (reporter molecule) or the other indicates the plant is one of the two species, where presence of both signals indicates a hybrid. Examples here show use of 6-carboxyflurescein (FAM); and 6-carboxy-2', 4,4',5',7,7'-hexachlorofluorescein (HEX) fluorophores, however any convenient means of producing a measurable signal may be used. Examples without intending to be limiting include tetrachlorofluorescein (TET); cyan florescent protein, yellow fluorescent protein, luciferase, SyBR Green I; ViC; CAL Fluor Gold 540, ROX Texas Red; CAL Fluor Red 610; CYS; Quasar 670; Quasar 705; and Fret.

In sum, a first primer is produced recognizing a first target nucleotide sequence in the genome of a first species, a second primer is produced recognizing a second target nucleotide sequence of a second species and the third common reverse primer universal to all genotypes allows for amplification. A "tail" reporter sequence is provided with the primer. The expression cassette comprises sequences complementary to the reporter sequence. With rounds of PCR, the cassette is no longer quenched and a measurable signal is produced.

When referring to the nucleic acid molecules and polypeptides of IAA and the degron and degron tail is intended to include those variants of the sequences retaining the properties so defined.

Methods of alignment of sequences for comparison are well known in the art. Thus, the determination of percent identity between any two sequences can be accomplished using a mathematical algorithm.

Optimal alignment of sequences for comparison can use any means to analyze sequence identity (homology) known in the art, e.g., by the progressive alignment method of termed "PILEUP" (Morrison, (1997) *Mol. Biol. Evol.* 14:428-441, as an example of the use of PILEUP); by the local homology algorithm of Smith & Waterman (*Adv. Appl. Math.* 2: 482 (1981)); by the homology alignment algorithm of Needleman & Wunsch (*J. Mol. Biol.* 48:443-453 (1970)); by the search for similarity method of Pearson (*Proc. Natl. Acad. Sci. USA* 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins (1988), *Gene* 73: 237-244; Corpet (1988), *Nucleic Acids Res.* 16:10881-10890; Huang, *Computer Applications in the Biosciences* 8:155-165 (1992); and Pearson (1994), *Methods in Mol. Biol.* 24:307-331); Pfam (Sonnhammer (1998), *Nucleic Acids Res.* 26:322-325); TreeAlign (Hein (1994), *Methods Mol. Biol.* 25:349-364); MEG-ALIGN, and SAM sequence alignment computer programs; or, by manual visual inspection.

Another example of algorithm that is suitable for determining sequence similarity is the BLAST algorithm, which is described in Altschul et al, (1990) *J Mol. Biol.* 215: 403-410. The BLAST programs (Basic Local Alignment Search Tool) of Altschul, S. F., et al., searches under default parameters for identity to sequences contained in the BLAST "GENEMBL" database. A sequence can be analyzed for identity to all publicly available DNA sequences contained in the GENEMBL database using the BLASTN algorithm under the default parameters.

Software for performing BLAST analyses is publicly available through the National Center for Biotechnology Information, www.ncbi.nlm.nih.gov/; see also Zhang (1997), *Genome Res.* 7:649-656 for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al (1990), *J Mol. Biol.* 215: 403-410). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff (1992), *Proc. Natl. Acad. Sci. USA* 89:10915-10919) alignments (B) of 50, expectation (E) of 10, M=5, N=−4, and a comparison of both strands. The term BLAST refers to the BLAST algorithm which performs a statistical analysis of the similarity between two sequences; see, e.g., Karlin (1993), *Proc. Natl. Acad. Sci. USA* 90:5873-5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch (*J Mol. Biol.* 48:443-453, 1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff (1993), *Proteins* 17: 49-61), which is currently the default choice for BLAST programs. BLOSUM62 uses a combination of three matrices to cover all contingencies. Altschul, J. Mol. Biol. 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) *Proc. Natl. Acad. Sci. USA* 89:10915).

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to the sequence of described would mean a polynucleotide or polypeptide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

As used herein, the terms "nucleic acid" or "polynucleotide" refer to deoxyribonucleotides or ribonucleotides and polymers thereof in either single- or double-stranded form. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. A nucleic acid often comprises standard nucleotides typically found in naturally occurring DNA or RNA (which can include modifications such as methylated nucleobases), joined by phosphodiester bonds. In some embodiments a nucleic acid may comprise one or more non-standard nucleotides, which may be naturally occurring or non-naturally occurring (i.e., artificial; not found in nature) in various embodiments and/or may contain a modified sugar or modified backbone linkage. Nucleic acid modifications (e.g., base, sugar, and/or backbone modifications), non-standard nucleotides or nucleosides, etc., such as those known in the art as being useful in the context of RNA interference (RNAi), aptamer, CRISPR technology, polypeptide production, reprogramming, or antisense-based molecules for research or therapeutic purposes may be incorporated in various embodiments. It will be appreciated that a great variety of modifications have been made to DNA and RNA that serve many useful purposes known to those of skill in the art. Such modifications may, for example, increase stability (e.g., by reducing sensitivity to cleavage by nucleases), decrease clearance in vivo, increase cell uptake, or confer other properties that improve the translation, potency, efficacy, specificity, or otherwise render the nucleic acid more suitable for an intended use. Various non-limiting examples of nucleic acid modifications are described in, e.g., Deleavey G F, et al., Chemical modification of siRNA. Curr. Protoc. Nucleic Acid Chem. 2009; 39:16.3.1-16.3.22; Crooke, S T (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008; U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929, 226; 5,977,296; 6,140,482; 6,455,308 and/or in PCT application publications WO 00/56746 and WO 01/14398. Different modifications may be used in the two strands of a double-stranded nucleic acid. A nucleic acid may be modified uniformly or on only a portion thereof and/or may contain multiple different modifications. Where the length of a nucleic acid or nucleic acid region is given in terms of a number of nucleotides (nt) it should be understood that the number refers to the number of nucleotides in a single-stranded nucleic acid or in each strand of a double-stranded nucleic acid unless otherwise indicated. An "oligonucleotide" is a relatively short nucleic acid, typically between about 5 and about 100 nt long. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J Biol. Chem.* 260:2605-2608; Rossolini et al. (1994) *Mol. Cell. Probes* 8:91-98). The term nucleic acid is used interchangeably with gene, cDNA, and mRNA encoded by a gene.

In certain embodiments, the nucleic acids include at least one base substitution, insertion, or deletion so that they do not recite a naturally occurring nucleic acid sequence.

Unless otherwise indicated, a particular nucleic acid sequence also implicitly encompasses conservatively modified variants thereof (e.g. degenerate codon substitutions) and complementary sequences as well as the sequence explicitly indicated. The term conservatively modified variants applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide is implicit in each described polypeptide sequence and is within the scope of the products and processes described.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., "Basic Methods in Molecular Biology" Appleton & Lange, Norwalk, Conn. (1994).

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., see, e.g., Creighton, Proteins: Structures and Molecular Properties (WH Freeman & Co.; 2nd edition (December 1993)).

The terms "polypeptide," "peptide," and "protein" are used interchangeably herein to refer to a polymer of amino acid residues. In general, a polypeptide may contain only standard amino acids or may comprise one or more non-standard amino acids (which may be naturally occurring or non-naturally occurring amino acids) and/or amino acid analogs in various embodiments. A "standard amino acid" is any of the 20 L-amino acids that are commonly utilized in the synthesis of proteins and are encoded by the genetic code. A "non-standard amino acid" is an amino acid that is not commonly utilized in the synthesis of proteins. Non-standard amino acids include naturally occurring amino acids (other than the 20 standard amino acids) and non-naturally occurring amino acids. An amino acid, e.g., one or more of the amino acids in a polypeptide, may be modified, for example, by addition, e.g., covalent linkage, of a moiety such as an alkyl group, an alkanoyl group, a carbohydrate group, a phosphate group, a lipid, a polysaccharide, a halogen, a linker for conjugation, a protecting group, a small molecule (such as a fluorophore), etc.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

In certain embodiments, a polypeptide disclosed herein may be a chimeric protein. A "chimeric protein" or "fusion protein" is a molecule in which different portions of the protein are derived from different origins such that the entire molecule is not naturally occurring. A chimeric protein may contain amino acid sequences from the same species or different species as long as they are not arranged together in the same way that they exist in a natural state. Examples of a chimeric protein include sequences disclosed herein that contain one, two or more amino acids attached to the C-terminal or N-terminal end that are not identical to any naturally occurring protein, such as in the case of adding an amino acid containing an amine side chain group, e.g., lysine, an amino acid containing a carboxylic acid side chain group such as aspartic acid or glutamic acid, a polyhistidine tag, e.g. typically four or more histidine amino acids.

In certain embodiments, a polypeptide disclosed herein may further comprise a label. A "label" refers to a detectable compound or composition that is conjugated directly or indirectly to another molecule, such as a protein, to facilitate detection of that molecule. Specific, non-limiting examples of labels include fluorescent tags, enzymatic linkages, and radioactive isotopes. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides are known in the art and may be used. Examples of labels for polypeptides include, but are not limited to, the following: radioisotopes or radionucleotides (such as $^{35}S$ or $^{131}I$) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, or predetermined polypeptide epitopes recognized by a secondary reporter (such as a leucine zipper pair sequences, binding sites for secondary antibodies, metal binding domains, epitope tags).

When referring to hybridization techniques, all or part of a known nucleotide sequence can be used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the DNA sequences. Methods for preparation of probes for hybridization and for construction of cDNA and genomic libraries are generally known in the art and are disclosed (Sambrook et al., 2001).

For example, the sequence disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 2001).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 0.1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m=81.5°$ C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can utilize a hybridization and/or wash at 1, 2, 3, or 4° C. lower than the thermal melting point $(T_m)$; moderately stringent conditions can utilize a hybridization and/or wash at 6, 7, 8, 9, or 10° C. lower than the thermal melting point $(T_m)$; low stringency conditions can utilize a hybridization and/or wash at 11, 12, 13, 14, 15, or 20° C. lower than the thermal melting point $(T_m)$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen (1993) *Laboratory Techniques in Biochemistry and Molecular Biology*—Hybridization with Nucleic Acid Probes, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (2001) *Molecular Cloning: A Laboratory Manual* (3rd ed., Cold Spring Harbor Laboratory Press, Plainview, N.Y.) and Haymes et al. (1985) In: *Nucleic Acid Hybridization*, a Practical Approach, IRL Press, Washington, D.C.

In general, sequences that correspond to the nucleotide sequences described and hybridize to the nucleotide sequence disclosed herein will be at least 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range, sharing at least about 50%, about 70%, and even about 85% or more sequence similarity.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

As discussed, the degron tail region of the IAA2 protein may be deleted or may be disrupted. When referring to disruption is meant that expression or activity of the region is reduced or prevented such that when the plant, plant part or cell is exposed to herbicide, in one embodiment the herbicide 2,4-D, the plant is tolerant to the herbicide.

The present invention provides, inter alia, isolated nucleic acids of DNA, RNA, homologs, paralogs and orthologs and/or chimeras thereof, comprising an herbicide tolerant IAA gene polynucleotide. This includes naturally occurring as well as synthetic variants and homologs of the sequences. Sequences homologous, i.e., that share significant sequence identity or similarity, to those provided herein derived from other plants of choice, are also an aspect of the invention.

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may result in two copies of a particular gene, giving rise to two or more genes with similar sequence and often similar function known as paralogs. A paralog is therefore a similar gene formed by duplication within the same species. Paralogs typically cluster together or in the same Glade (a group of similar genes) when a gene family phylogeny is analyzed using programs such as CLUSTAL (Thompson et al. (1994) Nucleic Acids Res. 22: 4673-4680; Higgins et al. (1996) Methods Enzymol. 266: 383-402). Groups of similar genes can also be identified with pair-wise BLAST analysis (Feng and Doolittle (1987) J. Mol. Evol. 25: 351-360).

For example, a clade of very similar MADS domain transcription factors from *Arabidopsis* all share a common function in flowering time (Ratcliffe et al. (2001) Plant Physiol. 126: 122-132), and a group of very similar AP2 domain transcription factors from *Arabidopsis* are involved in tolerance of plants to freezing (Gilmour et al. (1998) Plant J. 16: 433-442). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001), in Bioinformatics: Sequence and Genome Analysis Cold Spring Harbor Laboratory Press, Cold Spring Harbor, N.Y., page 543.)

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) Nucleic Acids Res. 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee et al. (2002) Genome Res. 12: 493-502; Remm et al. (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence).

Exemplary orthologous sequences of *Sisymbrium orientale* IAA2 from *Helianthus annuus, Vitis vinifera, Glycine max, Coffea canephora, Gossypium raimondii, Phaseolus vulgaris, Beta vulgaris, Capsicum annuum, Solarium lycopersicum*, and *Solanum tuberosum* are shown in SEQ ID NOs: 51-60. Additional sequences of orthologs as well as IAA paralogs are known to those of skill in the art and are readily available through sources such as GENBANK® or Ensembl Plants.

As used herein, the term "mutant" or "functional mutant" when made in reference to a gene or to a gene product refers, respectively, to a gene or to a gene product which displays modifications in sequence and/or functional properties (i.e., altered characteristics) when compared to the wild-type gene or gene product. Thus, the terms "modified" and "mutant" when used in reference to a nucleotide sequence refer to a nucleic acid sequence that differs by one or more nucleotides from another such that a disrupted or deleted degron tail region in the IAA protein is produced.

As used herein, "genetically modified plant" includes reference to a plant or ancestor thereof, to which has been introduced a heterologous polynucleotide. In some instances, the heterologous polynucleotide is stably integrated within the genome such that the polynucleotide is passed on to successive generations. In some instances, such as gene editing the heterologous polynucleotide engineers a chromosomal change that is passed to successive generations while the polynucleotide itself is not. The heterologous polynucleotide may be introduced alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by subsequent sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term introduced in the context of inserting a nucleic acid into a cell, includes transfection or transformation or transduction and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). When referring to introduction of a nucleotide sequence into a plant is meant to include transformation into the cell, as well as crossing a plant having the sequence with another plant, so that the second plant contains the heterologous sequence, as in conventional plant breeding techniques. Such breeding techniques are well known to one skilled in the art. For a discussion of plant breeding techniques, see Poehlman (1995) Breeding Field Crops. AVI Publication Co., Westport Conn., 4th Edit. Backcrossing methods may be used to introduce a gene into the plants. This technique has been used for decades to introduce traits into a plant. An example of a description of this and other plant breeding methodologies that are well known can be found in references such as Poehlman, supra, and Plant Breeding Methodology, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

To achieve this one could, for example, perform the following steps:
(a) plant seeds of the first (starting line) and second (donor plant line that comprises a gene of the invention) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:
(a) crossing a plant of a first genotype containing a desired gene, DNA sequence or element to a plant of a second genotype lacking the desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring a desired DNA sequence from a plant of a first genotype to a plant of a second genotype.

The terms "introgress" and "introgressing" and "introgression" refer to conventional (i.e. classic) pollination breeding techniques to incorporate foreign genetic material into a line of breeding stock. For example, the present invention provides for plants introgressed with a modified IAA2 protein having a disrupted or deleted degron tail region for herbicide tolerance by crossing two plant generations.

Transformation of a plant to produce expression of a polypeptide having a disrupted or deleted degron tail are processes well known to one of skill in the art.

A construct is a package of genetic material inserted into the genome of a cell via various techniques. The term nucleic acid construct refers to a coding sequence or sequences operably linked to appropriate regulatory sequences and inserted into a vector for transforming a cell. Such a nucleic acid construct may contain a coding sequence for a gene product of interest, along with a marker gene and/or a reporter gene.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

As used herein, the term vector refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J.

5:3057-3063; U.S. Pat. No. 5,591,439). Examples of non-viral vectors include, but are not limited to, liposomes, polyamine derivatives of DNA, and the like.

As used herein, a nucleotide segment is referred to as operably linked when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Operably linked elements may be contiguous or non-contiguous. When used to refer to the joining of two protein coding regions, by operably linked it is intended that the coding regions are in the same reading frame. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette can include one or more enhancers in addition to the promoter. By enhancer is intended a cis-acting sequence that increases the utilization of a promoter. Such enhancers can be native to a gene or from a heterologous gene. Further, it is recognized that some promoters can contain one or more enhancers or enhancer-like elements. An example of one such enhancer is the 35S enhancer, which can be a single enhancer, or duplicated. See for example, McPherson et al, U.S. Pat. No. 5,322,938.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids, or sclerenchyma. Such promoters are referred to as "tissue-preferred." A "cell type" specific promoter primarily drives expression in certain cell types in one or more organs, for example, vascular cells in roots or leaves. An "inducible" or "regulatable" promoter is a promoter which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the sequence to effect phenotypic changes in the organism. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. (See, for example, Miki and McHugh (2004) *Biotechnol.* 107, 193-232; Klein et al. (1992) *Biotechnology* (NY) 10, 286-291; and Weising et al. (1988) *Annu. Rev. Genet.* 22, 421-477). For example, the DNA construct may be introduced into the genomic DNA of the plant cell using techniques such as microprojectile-mediated delivery (Klein et al. 1992, supra), electroporation (Fromm et al., 1985 *Proc. Natl. Acad. Sci. USA* 82, 5824-5828), polyethylene glycol (PEG) precipitation (Mathur and Koncz, 1998 *Methods Mol. Biol.* 82, 267-276), direct gene transfer (WO 85/01856 and EP-A-275 069), in vitro protoplast transformation (U.S. Pat. No. 4,684,611), and microinjection of plant cell protoplasts or embryogenic callus (Crossway, A. (1985) *Mol. Gen. Genet.* 202, 179-185). *Agrobacterium* transformation methods of Ishida et al. (1996) and also described in U.S. Pat. No. 5,591,616 are yet another option. Co-cultivation of plant tissue with *Agrobacterium tumefaciens* is a variation, where the DNA constructs are placed into a binary vector system (Ishida et al., 1996 *Nat. Biotechnol.* 14, 745-750). The virulence functions of the *Agrobacterium tumefaciens* host will direct the insertion of the construct into the plant cell DNA when the cell is infected by the bacteria. See, for example, Fraley et al. (1983) *Proc. Natl. Acad. Sci. USA,* 80, 4803-4807. *Agrobacterium* is primarily used in dicots, but monocots including maize can be transformed by *Agrobacterium*. See, for example, U.S. Pat. No. 5,550,318. In one of many variations on the method, *Agrobacterium* infection of corn can be used with heat shocking of immature embryos (Wilson et al. U.S. Pat. No. 6,420,630) or with antibiotic selection of Type II callus (Wilson et al., U.S. Pat. No. 6,919,494).

Rice transformation is described by Hiei et al. (1994) *Plant J.* 6, 271-282 and Lee et al. (1991) *Proc. Nat. Acad. Sci. USA* 88, 6389-6393. Standard methods for transformation of canola are described by Moloney et al. (1989) *Plant Cell Reports* 8, 238-242. Corn transformation is described by Fromm et al. (1990) *Biotechnology* (NY) 8, 833-839 and Gordon-Kamm et al. (1990) supra. Wheat can be transformed by techniques similar to those used for transforming corn or rice. Sorghum transformation is described by Casas et al. (Casas et al. (1993) Transgenic sorghum plants via microprojectile bombardment. *Proc. Natl. Acad. Sci. USA* 90, 11212-11216) and barley transformation is described by Wan and Lemaux (Wan and Lemaux (1994) Generation of large numbers of independently transformed fertile barley plants. *Plant Physiol.* 104, 37-48). Soybean transformation is described in a number of publications, including U.S. Pat. No. 5,015,580.

The degron tail may be deleted or disrupted through a variety of gene editing techniques available to one of skill in the art. Any method that can prevent or disrupt expression or activity of the degron tail may be employed. Examples are provided below and are not intended to be limiting.

Methods which provide for targeting of the molecule of interest (MOI) to the target site of the target gene may be utilized in the method as well as means to delete or mutate one or more bases or residues. The following is provided by way of example rather than limitation. A guide nucleic acid molecule is one that directs the nuclease to the specific cut site in the genome, whether via use of a binding domain, recognition domains, guide RNAs or other mechanisms. The guide nucleic acid molecule is introduced into the cell under conditions appropriate for operation of the guide nucleic acid molecule in directing cleavage to the target locus. A person of skill in the art will have available a number of methods that may be used, the most common utilizing a nuclease to cleave the target region of the gene, along with sequences which will recognize sequences at the target locus and direct cleavage to the locus. Any nuclease that can cleave the phosphodiester bond of a polynucleotide chain may be used in the methods described here. By way of example without limitation, available systems include those utilizing site specific nucleases (SSN) such as ZFNs (Zinc finger nuclease), (Whyte, et al. Cell Biology Symposium: Zinc finger nucleases to create custom-designed modifications. *J Anim Sci* 90, 1111-1117 (2012)); TALENs (Transcription activator-like effector nucleases) (see, Carlson, D. F. et al. Efficient TALEN-mediated gene knockout in animals. *Proc Natl Acad Sci USA* 109, 17382-17387 (2012); Tan, W. et al. Efficient nonmeiotic allele introgression in livestock using custom endonucleases. *Proc Natl Acad Sci USA* 110, 16526-16531 (2013); and the CRISPR (Clustered regularly interspaced short palindromic repeats)-associated (Cas) nuclease system (Hai, T., Teng, F., Guo, R., Li, W. & Zhou, Q. One-step generation of knockout pigs by zygote injection of CRISPR/Cas system. *Cell Res* 24, 372-375 (2014)) that have permitted editing of animal genomes. The use of recombinases such as FLP/FRT as described in U.S. Pat. No. 6,720,475, or CRE/LOX as described in U.S. Pat. No. 5,658,772, can be utilized to integrate a polynucleotide sequence into a specific chromosomal site. Meganucleases have been used for targeting donor polynucleotides into a specific chromosomal location as described in Puchta et al., *PNAS USA* 93 (1996) pp. 5055-5060. ZFNs work with proteins or domains of proteins binding to a binding domain having a stabilized structure as a result of use a zinc ion. TALENs utilize domains with repeats of amino acids which can specifically recognize a base pair in a DNA sequence. For a discussion of both systems see Voytas et al. U.S. Pat. No. 8,697,853, incorporated herein by reference in its entirety. These systems utilize enzymes prepared for each target sequence.

A still further example of potential uses provides for introduction into a plant or cell of interfering nucleic acid molecules. For example, double-stranded RNA molecules (dsRNA) may be employed. In this process, in summary, RNA which is double stranded, in part, or completely, is produced based upon the sequence of the target nucleic acid molecule. Specifics of the means of producing the dsRNA may vary as one skilled in the art appreciates, and include, by way of example without intending to be limiting, the approach of Graham et al., U.S. Pat. No. 6,573,099 where two copies of a sequence corresponding to a target sequence is used, or that of Fire et al., U.S. Pat. No. 6,326,193 (both incorporated herein by reference), where the first strand is an RNA sequence corresponding to the target nucleic acid, and the second is one which is complementary to the target sequence, each of which are incorporated herein by reference in their entirety. These strands hybridize with each other to form the inhibiting dsRNA. The strand which corresponds to the target nucleic acid molecule can correspond to all or a portion thereof, as long as a dsRNA is formed. Where a strand is used which is the complement (antisense) of the target nucleic acid is used, it can be complementary to all or a portion of the target nucleic acid molecule, so long as the dsRNA formed interferes with the target nucleic acid molecule. The dsRNA triggers a response in which the RNAse III Dicer enzyme process dsRNA into small interfering RNAs (siRNA) of approximately 21-23 nucleotides, which are formed into a RNA-induced silencing complex RISC which destroys homologous mRNAs. (See, Hammond, S. M., et al., *Nature* (2000) 404:293-296). Generally, sequences of up to 10 nucleotides 20 nucleotides, 30 nucleotides, 40 nucleotides, 50 nucleotides, 100 nucleotides, 200 nucleotides, 300, 500, 550, 500, 550, or greater and any amount in-between may be used.

Any method of deleting or disrupting degron tail expression of activity may be used in the present methods, and a vast variety of such methods are known. A few examples of such methods are provided by way of example below, ranging from physical or chemical mutagen applications, to gene editing which has provided many accurate and precise techniques, cosuppression, antisense silencing, RNA interference, or any of many others available.

Methods are also provided to reduce or eliminate the activity of a degron tail by transforming a plant cell with an expression cassette that expresses a polynucleotide that inhibits the expression of the degron tail. The polynucleotide may inhibit the expression of the degron tail directly, by preventing transcription or translation of the degron tail synthase messenger RNA, or indirectly, by encoding a polypeptide that inhibits the transcription or translation of an degron tail nucleic acid molecule encoding an degron tail polypeptide. Methods for inhibiting or eliminating the expression of a gene in a plant are well known in the art, and any such method may be used in the present invention to inhibit the expression of the degron tail polypeptide. Many methods may be used to reduce or eliminate the activity of a degron tail polypeptide. In addition, more than one method may be used to reduce the activity of a single degron tail polypeptide.

In some embodiments of the present invention, a plant is transformed with an expression cassette that is capable of expressing a polynucleotide that inhibits the expression of a degron tail polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one degron tail polypeptide is an expression cassette capable of producing an RNA molecule that inhibits the transcription and/or translation of at least one degron tail synthase polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an degron tail polypeptide include sense suppression/cosuppression, where an expression cassette is designed to express an RNA molecule corresponding to all or part of a messenger RNA encoding an degron tail polypeptide in the "sense" orientation and over expression of the RNA molecule can result in reduced expression of the native gene. With antisense suppression the expression cassette is designed to express an RNA molecule complementary to all or part of a messenger RNA encoding the degron tail polypeptide and over expression of the antisense RNA molecule can result in reduced expression of the native gene. In double-Stranded RNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA. Hairpin RNA interference and intron-containing hairpin RNA interference utilizes an expression cassette is designed to express an RNA molecule that hybridizes with itself to form a hairpin structure that comprises a single-stranded loop region and a base-paired stem. Small Interfering RNA or Micro RNA employs an expression cassette is designed to express an RNA molecule that is modeled on an endogenous miRNA gene.

In one embodiment, the polynucleotide encodes a zinc finger protein that binds to a gene encoding an degron tail polypeptide, resulting in reduced expression of the gene, Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication Nos. 2003/0037355; each of which is herein incorporated by reference.

In some embodiments, the polynucleotide encodes an antibody that binds to at least one degron tail and reduces the activity of the degron tail polypeptide. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36.

In some embodiments, the activity of a degron tail polypeptide is reduced or eliminated by disrupting the gene encoding the degron tail polypeptide. The gene encoding the degron tail polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced degron tail activity.

Unless otherwise specifically explained, all technical and scientific terms used herein have the same meaning as commonly understood by those of ordinary skill in the art to which this disclosure belongs. It is to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The following is provided by way of exemplification and is not intended to limit the scope of the invention. All references cited herein are herein by reference.

EXAMPLES

Example 1: Candidate Gene Identification Through RNAseq

Plant Material

A population of 2,4-D-resistant *S. orientale* was collected from a wheat field in Port Broughton (PB-R1), a second 2,4-D resistant population was collected 9.2 km away (PB-R2), while the susceptible population originated from Roseworthy (S), South Australia, Australia, about 120 km away from the resistant populations. PB-R1 plants were reported to be 22-fold more resistant to 2,4-D and 20-fold more resistant to MCPA compared to S plants.

Two biparental crosses were made to study inheritance of 2,4-D resistance, using PB-R1 as the male parent for Cross A and PB-R2 as the male parent for Cross B, and Roseworthy S as the female parent for both crosses. Crosses were performed by hand emasculation of S and hand pollination with pollen from the R parent. The F1 progeny were self-pollinated to produce F2 progeny, and F2 individuals were self-pollinated to produce F3 progeny. The F3 progeny were sprayed with 150 g a.i. $ha^{-1}$ 2,4-D (2,4-D amine, Shredder, Winfield) using an overhead track sprayer (DeVries Manufacturing) equipped with a flat-fan nozzle tip (TEEJET® 8002EVS, Spraying System) calibrated to deliver 187 L $ha^{-1}$ of spray solution at 172 kPa to visually determine 2,4-D resistance segregation, evaluated 21 DAT. Homozygous resistant and homozygous susceptible F3 lines were inbred via single-seed descent to create recombinant inbred lines (RILs) to the F4 generation (Cross A). The F3 generation was used for Cross B.

RNA-Sequencing

The transcriptome of six F4 recombinant inbred lines (RILs) from a cross between 2,4-D resistant PB-1 and susceptible S (Cross A), and six F3 RILs from a cross between 2,4-D resistant PB-2 and susceptible S (Cross B) was sequenced. From Cross A, three RILs were homozygous 2,4-D-resistant and three RILs were homozygous 2,4-D-susceptible. From Cross B, two RILs were homozygous 2,4-D-resistant and four RILs were homozygous 2,4-D-susceptible. The samples used for RNA-Sequencing were first germinated on agar plates, transplanted to 3×3 cm pots filled with potting soil, and grown in a growth chamber at 25/20° C., 16/8 h light/dark photoperiod. At the four-leaf stage, the youngest expanded leaf was collected. Samples were frozen immediately in liquid nitrogen and total RNA was extracted using the RNeasy Plant Mini Kit (Qiagen). Sample quality was assessed by RIN score (Agilent TapeStation) as well as by gel electrophoresis. DNAse treatment, library preparation, and sequencing were conducted at the Roy J. Carver Biotechnology Center at the University of Illinois. Libraries were prepared using the TruSeq Stranded mRNA Sample Prep Kit (Illumina). Sequencing was performed on a HiSeq 4000 (Illumina) using bar-coded adapters in two lanes of the Illumina flow-cell for 101 cycles, yielding 1.6 billion paired-end reads. Individual library yields ranged from 52 to 75 million paired-end reads. Fastq files were generated and demultiplexed with bcl2fastq v2.17.1.13 conversion software (Illumina) and adaptors were trimmed from the 3'-end reads.

A de novo reference transcriptome was obtained by separately assembling Illumina reads from a Cross A 2,4-D-resistant RIL (R206) and a susceptible RIL (S242) with Trinity. The assembled contigs were filtered for minimum contig length of 500 bp. The two assemblies were compared using CDHit v4.6.6 with a 95% confidence interval to eliminate redundant contigs and retain all contigs unique to either the R or S assembly. This resulted in a 72-Mb transcriptome with 37,223 contigs. Putative annotations were assigned using Trinotate and the TAIR10 protein database. Read alignments to the de novo reference transcriptome were conducted with Bowtie2 using the default "end-to-end" mode and the "sensitive" option. The minimum allowed fragment length was set to 100 and the maximum to 800 bp.

Differential Expression and SNP Analysis

Raw read counts were extracted using SAMtools. Counts-per-million (CPM) and gene expression differences were calculated with the package 'edgeR' using the statistical software R v3.3 and an expression threshold of ≥1 CPM in at least two samples. After normalization of the RNA composition the data was analyzed using the 'classic approach'. Expression differences were compared between 2,4-D resistant and susceptible RILs within Cross A and B, respectively, as well as between all 2,4-D-resistant and -susceptible RILs. Differentially expressed transcripts were then filtered for a fold-change of ≥|2| and a false discovery rate (FDR) adjusted p-value ≤0.05. Single nucleotide polymorphism (SNP) calling was performed using SAMtools (v. 1.3.1) with the default options and the "mpileup" command. The command "bcftools" was used to retain only SNPs that had a quality score higher than 10 and read depth higher than 10. An additional filtering step was for SNPs that were heterozygous or homozygous in at least three individuals of all R and all S RILs. Contigs with annotations in the TIR1/AFB family and the Aux/IAA gene family were manually inspected for sequence variants between R and S RILs using IGV to view BAM file read alignments.

Figures 5, 6:
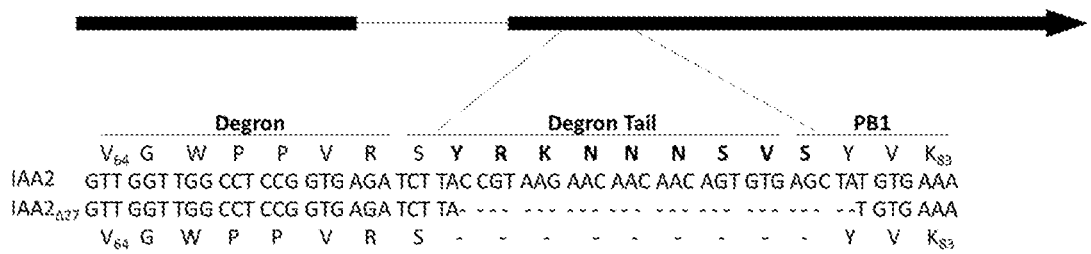
FIG. 5 shows the transcripts that had differential expression between R and S RILs of both Port Broughton and P2 populations based on cutoff criteria of FDR <0.05 and fold change of >|2|.
FIG. 6 shows the deletion of 27 nucleotides from the IAA2 gene results in a 9 amino acid deletion in the degron tail region of IAA2 (SEQ ID NOs: 1-4).

Only three transcripts had differential expression between R and S RILs of both Port Broughton and P2 populations based on cutoff criteria of FDR <0.05 and fold change of >|2| (FIG. 5). These included IAA2 (3.3 fold lower in R than S, FDR<0.0001, homology to AT3G23030), PRP39-2 (10 fold lower in R than S, FDR<0.0001, homology to AT5G46400), and ABCB13 (6 fold higher in R than S, FDR <0.01, homology to AT1G27940). Notably, PRP39-2 and ABCB13 both had at least one RIL replicate inconsistent with the general pattern, while IAA2 had lower read counts in all R RILs compared to all S RILs. No SNPs were identified that were shared among all R RILs and different from all S RILs from the two populations. However, inspection of the read alignments to IAA2 identified a small gap in read coverage for all R RILs, whereas all S RILs had continuous read coverage at this position.

Example 2: Candidate Gene Validation

IAA2 Gene Sequencing

To further investigate and validate the results found for IAA2 through RNAseq, a region of the IAA2 gene was sequenced. A 239 bp region of the IAA2 gene was amplified (forward primer 5'-AACTCAAATCGTTGGTTGGC-3' (SEQ ID NO: 61) and reverse primer 5'-CTT-TATCCTCGTACGTTGGTACG-3' (SEQ ID NO: 62)) and sequenced for 3 R and 3 S RILs and the R allele was found to contain a 27 bp deletion (IAA2$_{\Delta 27}$) (FIG. 6).

The deletion results in a functional, in-frame IAA2 protein, but missing amino acids 73 to 81, removing most of the degron tail region located between the degron and the PB1 domain (FIG. 6). No S alleles contained a deletion in IAA2, suggesting the deletion was correlated with resistance. The deletion also explains the observed lower expression value in R RILs, rather than a reduced transcriptional rate.

Deletion and Resistance Correlation in Other Resistant Populations

The presence of IAA2$_{\Delta 27}$ in other 2,4-D resistant populations of S. orientale was also investigated. Seeds of S. orientale populations were germinated by sowing directly onto the soil surface of seedling trays containing standard potting mix. Once emerged, seedlings were transplanted into 9.5×8.5×9.5 cm punnet pots and grown outdoors at the Waite Campus, University of Adelaide, Australia. At the 4-leaf stage, plants were treated with a single rate of 250 g. a. ha$^{-1}$ 2,4-D (2,4-D amine 650, FMC) to screen for resistance. Herbicide was applied using a laboratory moving boom pesticide applicator and applied at an equivalent of 109 L ha−1 of water at a pressure of 250 kPa and a speed of 1 m s−1 using Tee-Jet 001 nozzles (Tee-Jet 8001E; Spraying Systems Co., Wheaton, Ill.). Leaf curl was assessed 48 h after treatment, with any plants showing signs of leaf curl considered susceptible and tissue harvested, while the remaining plants were considered resistant and allowed to grow for a further 21 days to confirm resistance and tissue subsequently harvested. Eight populations from Southern Australia, including parent populations PB-1R and PB-2R were screened for resistance to 2,4-D, with four identified as resistant.

The IAA2 gene was sequenced to determine the presence or absence of IAA2$_{\Delta 27}$ in a number of individual plants from each populations. Genomic DNA was extracted using the Isolate II Plant DNA kit (Bioline, Alexandria, New South Wales, Australia) according to the manufacturer's instructions. The concentration of nucleic acids was determined spectrophotometrically on a nanodrop ND-1000 (Thermo Scientific, Wilmington, Del., USA) at 260 nm. For polymerase chain reaction (PCR) amplification, ~100 ng of gDNA was added to a standard 25 μL PCR reaction mix containing 1×MyFi reaction buffer (containing 0.2 mM of dNTPs and 0.6 mM of MgCl$_2$), 0.4 μM of each gene-specific primer (as above) and 1 μL of MyFi DNA polymerase (Bioline). Amplification was carried out in an automated DNA thermal cycler (GeneTouch, Bioer Technology, Binjiang, Hangxhou, China) with PCR conditions as follows: 1 min denaturing at 95° C.; 35 cycles of 15 s denaturation at 95° C., 30 s annealing at 58° C., 15 s elongation at 72° C. and a final extension for 7 min at 72° C. PCR products were prepared with 1× Ficoll loading dye [15% (w/v) Ficoll 4000, 0.25% (w/v) bromophenol blue, 0.25% (w/v) xylene cyanol FF] and visualised on SYBR Safe (Life Technologies, Mulgrave, Victoria, Australia) stained agarose gels. Samples were electrophoresed in 1×TAE buffer (40 mM of Trizma base, 1 mM of Na$_2$EDTA, pH to 8 with glacial acetic acid) at 100 V and photographed under UV light (Δ=302 nm). DNA fragment sizes were estimated by comparing their mobility with bands of known sizes of a low-molecular-weight marker (EasyLadder & HyperLadder; Bioline).

Amplified fragments were cloned using the Topo TA cloning kit (Life Technologies) according to the manufacturer's instructions to facilitate sequencing. Colony PCR was performed to determine positive clones carrying the fragment, using the same PCR protocol as used for amplification, but replacing the template DNA with a single clone colony, and increasing the initial denaturing step to 10 min to aid cell lysis. Before addition into the PCR reaction, colonies were streaked onto standard LB/kan plates and plasmid DNA of positive clones isolated from the regrown streaked colonies (Isolate II Plasmid Mini Kit, Bioline). Plasmids were sequenced using the standard M13 vector primers with sequencing conducted by the Australian Genome Research Facility (AGRF). Sequence data were analyzed using ContigExpress from the Vector-NTI Suite 6 programs (Life Technologies).

Only wild type IAA2 was present in individuals from four susceptible populations P15, P31, P49 and P50 (Table 2). All individuals from the two parent resistant populations, PB-1R and PB-2R, contained IAA2$_{\Delta 27}$ Individuals from resistant population P17 were found to contain either IAA2$_{\Delta 27}$ alone, or both IAA2$_{\Delta 27}$ and the wild type IAA2 with no deletion IAA2$_{WT}$, suggesting a segregating population. Population P28, although resistant, did not contain IAA2$_{\Delta 27}$.

TABLE 2

| Population | No. of individuals | Banding pattern | | |
|---|---|---|---|---|
| | | IAA2$_{WT}$ | IAA2$_{Δ27}$ | IAA2$_{WT}$/IAA2$_{Δ27}$ |
| P2 (R) | 20 | | 20 | |
| P13 (R) | 20 | | 20 | |
| P15 (S) | 15 | 15 | | |
| P17 (R) | 20 | | 14 | 6 |
| P28 (R) | 20 | 20 | | |
| P31 (S) | 5 | 5 | | |
| P49 (S) | 5 | 5 | | |
| P50 (S) | 5 | 5 | | |

Segregation Analysis

A KASP genotyping assay was developed using a forward primer specific to the R allele appended with a linker sequence for the HEX fluorophore (gene specific sequence italicized) (5'-GAAGGTCGGAGTCAACGGAT-TCTCCGGTGAGATCTTATGTG-3')(SEQ ID NO:63) and a forward primer specific to the S allele appended with a linker sequence for the FAM fluorophore (5'-GAAGGTGACCAAGTT-CATGCTCGTAAGAACAACAACAGTGTGAGC-3') (SEQ ID NO: 64), together with a universal reverse primer (5'-ATTTTGCGGAGGTATGGTGC-3') (SEQ ID NO: 65). The analysis was performed by mixing a primer master mix containing the 3 primers and a KASP master mix. 4 µl of the master mix was mixed to 4 µl of plant DNA at 20 nM uL$^{-1}$. FAM and HEX fluorescence was obtained and corrected by removing background fluorescence obtained in a non-template control.

A progeny test segregation analysis was performed on 219 F3 plants derived from self-pollination of a heterozygous F2 individual from cross B, identified via progeny test due to segregation of 2,4-D resistance in the F3 progeny. Plants were sprayed with 200 gai ha$^{-1}$ 2,4-D at the 5 true leaf stage. Damage percentage was evaluated at 28 days after treatment. Leaf tissue was harvested and genomic DNA was extracted by CTAB. A KASP assay was performed with primers and methods as described above. To further test the co-segregation between the resistant phenotype and IAA2$_{Δ27}$, nine each of R and S RILs from cross A and three each of R and S RILs from cross B were genotyped using the KASP assay. Two individuals were genotyped from each RIL.

Figure 7:
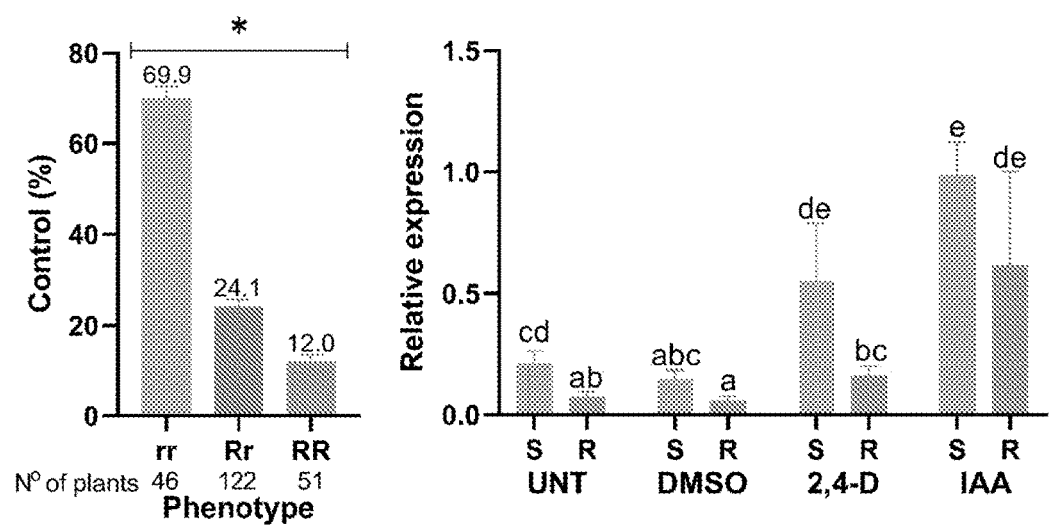
FIG. 7 shows the deletion allele co-segregates with 2,4-D resistance in an F2 population and that 2,4-D treatment increases IAA2 expression in S but not in R.

The association between IAA2$_{Δ27}$ and the resistant phenotype was confirmed by a segregation analysis, where all sensitive plants exhibited 70% visual injury and were homozygous for IAA2$_{WT}$; heterozygous plants showed an average of 24% injury and homozygous resistant 12%. This significant difference between heterozygous and homozygous R is probably due to semi-dominance for the resistant gene. The relative expression (RE) of IAA2 also confirmed the results of the RNAseq, where untreated seedlings showed 3-fold higher expression in S (RE=0.21) compared to R (RE=0.07). Auxin treatment significantly increased the expression of IAA2 in R (2.5-fold for 2,4-D and 9.5-fold for IAA) and S (4-fold for 2,4-D and 7-fold for IAA) seedlings compared to untreated plants and DMSO control. Treated susceptible plants (2,4-D RE=0.55; IAA RE=1) showed significant increased expression compared to resistant (2,4-D RE=0.16; IAA RE=0.62) (FIG. 7).

Example 3: *Arabidopsis* Transformation

*Arabidopsis* transformation was performed based on established protocols with modifications. IAA2 alleles were amplified by PCR from cDNA generated from RNA extracts of homozygous R and S F5 lines (cross A). RNA was extracted using Direct-zol RNA Miniprep Plus Kit (Zymo). cDNA synthesis was performed using oligo(dT)$_{20}$ primers from SuperScript™ II Reverse Transcriptase (Invitrogen). Wild-type and mutant alleles were amplified by PCR using PrimeSTAR HS Premix (Takara), using primers linked with restriction enzyme sites for cloning. Purified PCR amplicons were ligated into the pGEM-T Easy Vector (Promega), transformed into *E. coli*, sequenced by Sanger sequencing, and digested using the restriction sites AscI and BamHI (New England BioLabs). The digested product was then ligated into the binary vector pFGC5941 and cloned into *Agrobacterium tumefaciens* (strain GV3101). For plant transformation, *Agrobacterium* 400 mL liquid cultures were incubated at 28 C overnight and after centrifugation, resuspended in a 300 mL transformation solution (5% sucrose and 0.02% Silwet L-77). Each allele of IAA2 was transformed into *Arabidopsis thaliana* (Col-0) by floral dip and grown to seed production.

For transformant selection, 40 mg of transformed seeds for each IAA2 allele were cleaned with bleach solution (12.5%) and plated at half MS selective media with Cefotaxime (200 mg/L) and glufosinate-ammonium (7.5 mg/L). After two weeks, positive transformants were transferred to a second selective plate with half MS, Cefotaxime (100 mg/L) and glufosinate-ammonium (5 mg/L). After selection, potential transformants were transferred to soil and grown until seed production. For T2 selection, 36 seeds were cleaned and grown on half MS and glufosinate-ammonium (5 mg/L) media. T3 homozygous plants containing just one copy of the T-DNA vector were selected and IAA2 expression was analyzed using the same primers from mustard expression assay (see below), AtCyclophilin and AtActin2 were used as normalization genes. Three expressing homozygous lines from each version of the IAA2 WT and 427 with just one copy of the T-DNA inserted vector were selected and used for the root growth experiments.

Primers Used for Transformation:

```
lAA2-FW-AscI:
                                    (SEQ ID NO: 66)
5'-TTGGCGCGCC ATGGCGTACGAGAAAGTCAATGAGCTTA-3' lAA2-RW-BamHI:
                                    (SEQ ID NO: 67)
5'-CGGGATCCTCATAAGGAAGAGTCATCAGATCCTTTCATGATTC-3'
```

Figure 8:
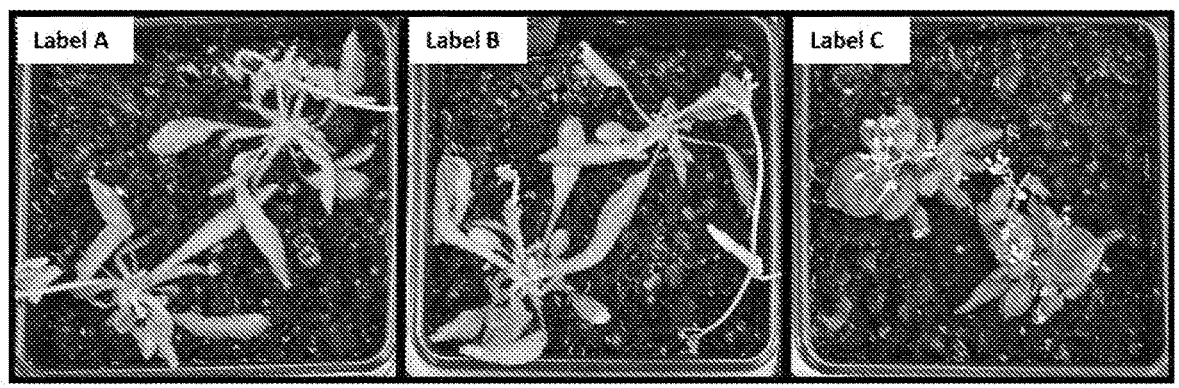
FIG. 8 shows that the wild-type *Arabidopsis* (panel A) and *Arabidopsis* transformed with IAA2 wild-type allele (panel B) are both sensitive to 2,4-D. Panel C shows *Arabidopsis* transformed with IAA2Δ27 that is resistant to 2,4-D treatment.

The wild type *Arabidopsis* and *Arabidopsis* transformed with the wild type *Sisymbrium orientale* IAA2 were susceptible when treated with 200 g a.i. ha$^{-1}$ 2,4-D (FIG. 8). *Arabidopsis* transformed with *Sisymbrium orientale* IAA2$_{Δ27}$ with the 27 base pair deletion, was resistant to 2,4-D. This confirms that the deletion within the degron region of *Sisymbrium orientale* IAA2 was sufficient to provide resistance to 2,4-D.

Root Assays and Gene Expression Analysis of AUX/IAA2 after Auxin Treatment

Figure 9:
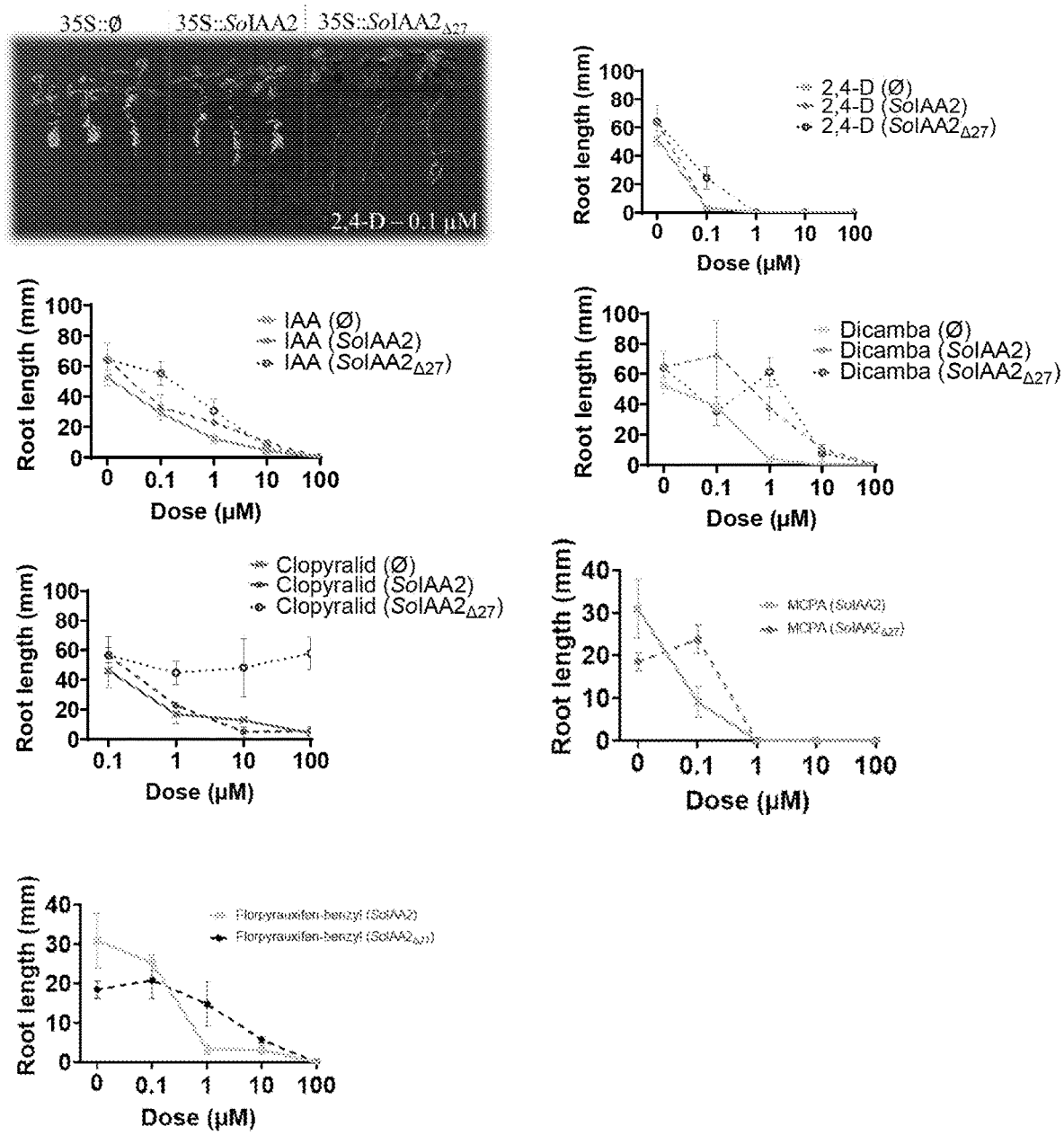
FIG. 9 shows transformation of *Arabidopsis thaliana* with IAA2 wild-type allele and IAA2Δ27 allele from *Sisymbrium orientale* results in different responses of root growth to auxin and herbicides. Upper left panel: only IAA2Δ27 allele can grow on media containing 2,4-D. Right panels: IAA2Δ27 allele expressed in transgenic *Arabidopsis* confers resistance to IAA, 2,4-D, dicamba and clopyralid relative to wild-type *Arabidopsis* and wild-type IAA2 allele. MCPA and florpyrauxifen-benzyl were tested in root growth assays on *S. orientale* inbred lines containing IAA2 wild-type allele (SoIAA2) or deletion mutant allele (SoIAA2Δ27). The SoIAA2Δ27 mutant allele confers resistance to MCPA and florpyrauxifen-benzyl.

Resistance was further confirmed using transformed *Arabidopsis* using a root growth assay. In this assay, germinated seedlings were placed on agar plates containing IAA, 2,4-D, or dicamba and new root growth measured after 7 days. *Arabidopsis* transformed with the null vector, not containing *S. orientale* IAA2 were susceptible to inhibition by 2,4-D, dicamba, and to a lesser extent higher concentrations of IAA (FIG. 9). *Arabidopsis* transformed with the wild type *S. orientale* IAA2 had similar responses to 2,4-D and IAA compared with the null vector. However, these plants were slightly more tolerant to dicamba (FIG. 9). *Arabidopsis* transformed with the mutant *S. orientale* IAA2$_{\Delta27}$ showed higher tolerance in the root growth assay to 2,4-D, dicamba, clopyralid, and IAA compared with either the null vector or wild type gene. From this assay, it is clear that the IAA2$_{\Delta27}$ can provide resistance to dicamba as well as 2,4-D. *S. orientale* RILs homozygous for the IAA2$_{\Delta27}$ showed higher tolerance to MCPA and fluorpyrauxifen-benzyl (FIG. 9).

All root assays were performed on 120 mm square petri dishes with half MS and 1% phytoagar. Natural and synthetic auxins were bought from Caisson Labs (2,4-D, dicamba, and IAA) Stock solutions were made in DMSO at 1 mM and 0.001 mM and finally dissolved into 100 ml depending on the final concentration of the treatment. For the auxin treatments 2,4-D and dicamba were 0.01, 0.05, 0.1, 0.5, 1, 10 and 100 uM; for IAA 0.1, 0.5, 1, 10, 100, and 1000 uM; DMSO at 1 uL mL$^{-1}$ was used for the control. For the mustard root assay, ten seedlings (3 days after germination) of F5 RILs of each phenotype were transferred to an auxin treated or control plate, the root tip of each plant was marked and root growth was evaluated seven days after treatment. For *Arabidopsis*, sterilized seeds were planted directly on the treated petri dish and incubated at 4° C. for seed scarification and moved to the growth chamber after 3 days. T3 homozygous plants of 35::SoIAA2$_{WT}$, 35::SoIAA2$_{\Delta27}$, the T-DNA insertion line on AtIAA$_2$ and the empty T-DNA from PFGC5941 plasmid as control were used in this study. Twelve plants per construct ware used in total and roots were measured three weeks after the plates were moved to the growth conditions. For all root assays, seeds were gas sterilized for 6 hours using bleach and hydrochloric acid. The plants were grown under controlled conditions of 180 uMol m$^{-2}$ light intensity, relative humidity of 60%, 16 hours of day and day/night temperatures of 22/18° C.

To study IAA2 expression under auxin treatments sterilized seeds from F5 RILs for each phenotype were planted in half MS and grown until expanded cotyledon stage (size was about 2 cm from root to cotyledon tips). Four plants of each phenotype were then dipped in different half MS liquid media containing DMSO as control, dicamba, IAA, or 2,4-D for 2 hr. After exposure plants were collected into 2 ml centrifuge tubes and frozen in liquid nitrogen. RNA was extracted using Direct-zol RNA Microprep from Zymo research, DNAase treatment was done using DNaseI from Invitogen—ThermoFisher and cDNA was generated using iScript™ according to each manufacture protocol. Q-PCR (CFX Connect™ Real-Time PCR Detection System thermal cycler, BioRad, Hercules, Calif.) was used to determine IAA2 expression. The qPCR reaction contained 12.5 µl of SYBR Green (PerfeCTa SYBR Green FastMix), 1 µl each of forward and reverse primers (5 µM), and 1 uL of cDNA for a final reaction volume of 25 Q-PCR parameters were 50° C. for 2 min, 95° C. for 10 min, and 40 cycles of 95° C. for 30 s and 60° C. for 1 min. Relative expression quantification was calculated by Expression=$2^{\Delta Ct}$, where $\Delta C_T=C_T$(average of Actin2 and Cyclophilin)–$C_T$(IAA2). Each biological sample was run in two technical replicates.

Primers Used for Expression Measurements:

SoIAA2$_{WT}$:
FW
(SEQ ID NO: 68)
5'-GAACAACAACAGTGTGAGCTATG-3'

RV
(SEQ ID NO: 69)
5'-GCCTTGAGAAGCTCTGGATAG-3'

SoIAA2Δ27:
FW
(SEQ ID NO: 70)
5'-CTCCGGTGAGATCTTATGTG-3'

RV
(SEQ ID NO: 71)
5'-CTCCGGTGAGATCTTATGTG-3'

SoCyclophilin
FW
(SEQ ID NO: 72)
5'-CATGTGCCAAGGAGGAGATT-3'

RV
(SEQ ID NO: 73)
5'-GTGTGCTTCCTCTCGAAGTT-3'

SoActin2
FW
(SEQ ID NO: 74)
5'-GTGGAACCACTATGTTCTCTGG-3'

RV
(SEQ ID NO: 75)
5'-GGAGGTGCAACGACCTTAAT-3'

Example 4: Surface Plasmon Resonance (SPR) Affinity Binding Analysis

Figure 10:
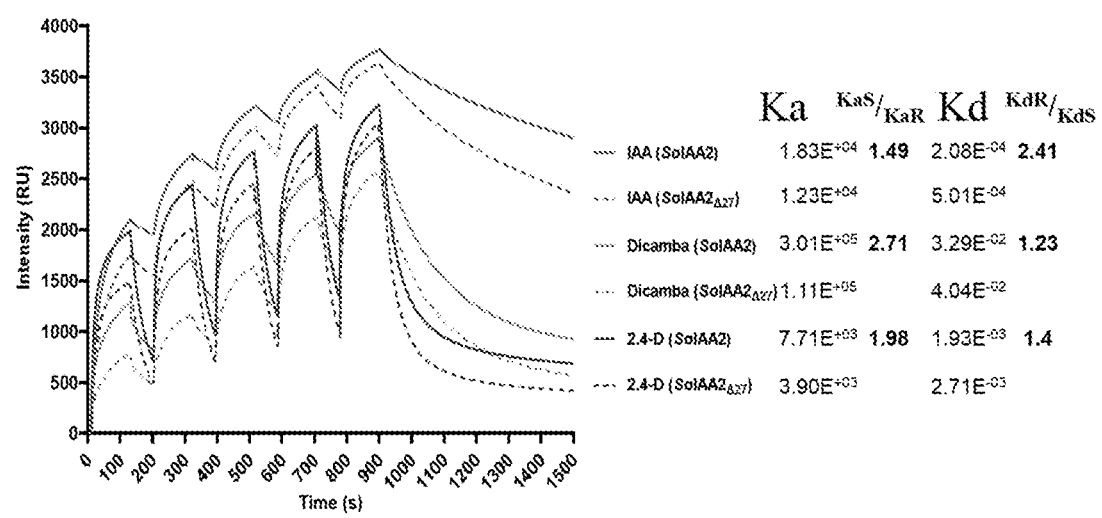
FIG. 10 shows the surface plasmon resonance assay for IAA2 and IAA2427 alleles from *Sisymbrium orientale*. The IAA2427 peptide has a slower association constant (Ka) for the TIR1/auxin/IAA complex than the IAA2 wild-type allele for auxin (IAA), dicamba, and 2,4-D. The IAA2427 peptide has a faster disassociation constant (Kd) for the TIR1/auxin/IAA complex than the IAA2 wild-type allele for auxin (IAA), dicamba, and 2,4-D. Data from Richard Napier and Martin Kubes, University of Warwick, UK.

The mechanism whereby the deletion in IAA2 interferes with auxinic herbicide action was explored using surface plasmon resonance (SPR) assay. In short, this assay measures the binding of auxin and IAA to the receptor protein TIR1 and their unbinding. The assay showed that the presence of the mutant IAA2$_{\Delta27}$ resulted in slower association of the herbicide/IAA/TIR1 complex and more rapid dissociation of the complex (FIG. 10). This was true in the presence of IAA, 2,4-D and dicamba. This shows that the mechanism of action of all three is impaired by the deletion.

Surface plasmon resonance (SPR) experiments were done according to published protocols. TIR1/AFBS was expressed in insect cell culture using a recombinant baculovirus. The construct contained sequences for three affinity tags, namely 6 His, maltose-binding protein (MBP) and FLAG. Initial purification using the His tag was followed by clean-up using FLAG chromatography, the purified protein was used for SPR assays by passing it over a streptavidin chip loaded with biotinylated IAA2/IAA7 degron peptides.

The SPR buffer was Hepes-buffered saline with 10 mM Hepes, 3 mM EDTA, 150 mM NaCl and 0.05% Tween 20. Compounds to be tested were premixed with the protein to a final 50 µM concentration. Binding experiments were run at a flow rate of 30 µl min$^{-1}$ using 2.0 min of injection time and 4.0 min of dissociation time. Data from a control channel (mIAA7) and from a buffer+DMSO-only run were subtracted from each sensogram following the standard double reference subtraction protocol.

Example 5: Mechanistic Model of *S. orientale* IAA2$_{\Delta27}$

Figure 11:
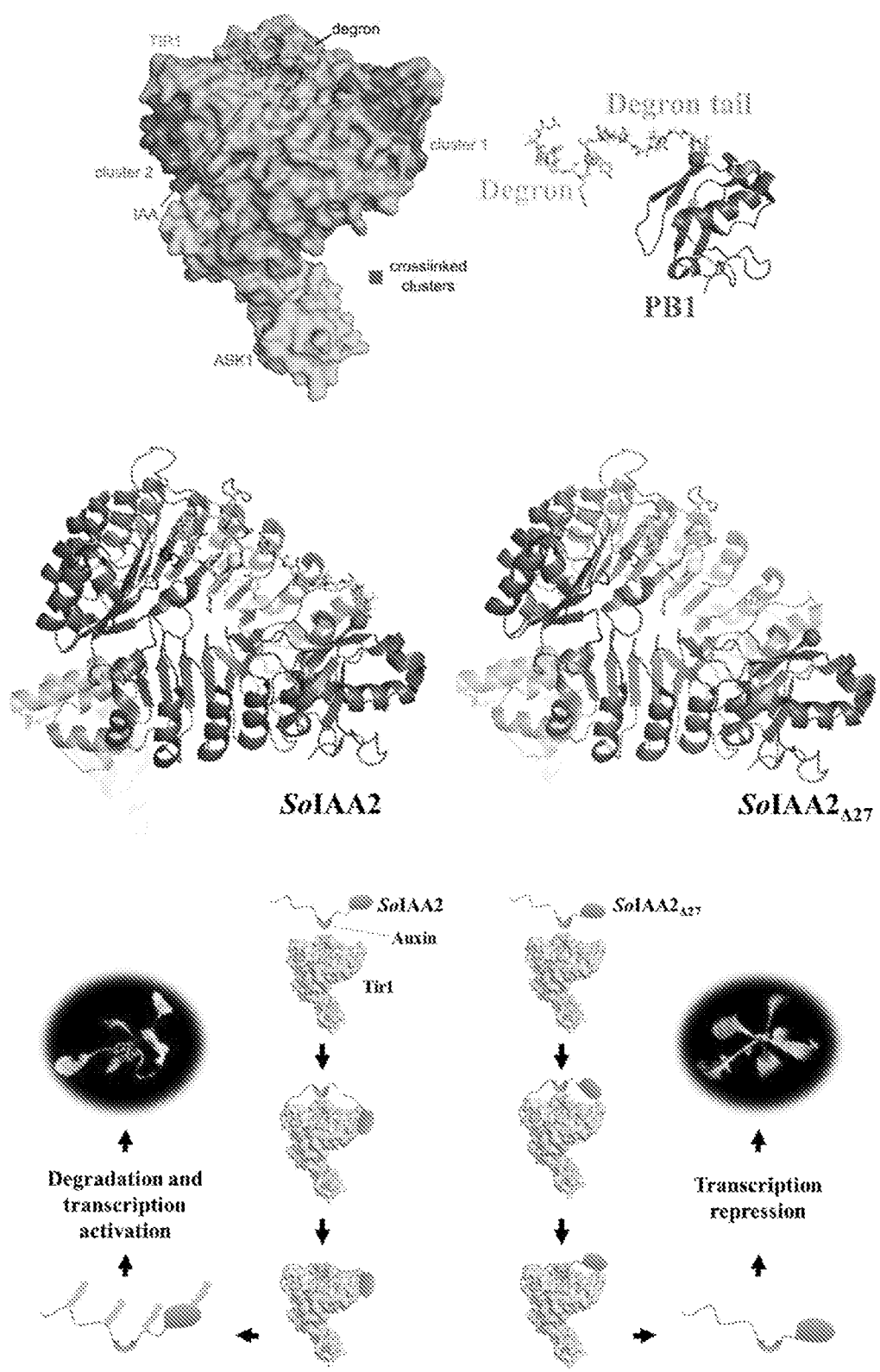
FIG. 11 shows the predicted mechanistic effects of IAA2427 deletion on association with the TIR1/synthetic auxin/IAA protein complex (top panel). The deletion is predicted to reduce the rate of association and increase the rate of dissociation, resulting in less degradation of the IAA2 protein and plant survival. The loss of 9 amino acids reduces the distance of the domain III of IAA2 from domain II by 28 angstroms (middle panel), which is predicted to impair the ability of the IAA2 protein to interact with the TIR1/ synthetic auxin complex (bottom panel).

A mechanistic model, which explains how the deletion within the degron would interfere with the action of auxinic herbicides is presented in FIG. 11. The IAA protein and TIR1 protein form an auxin receptor complex where the auxin, or auxinic herbicide, is bound to the TIR1 protein just under the IAA protein. The complex is recognized by SCF$^{TIR1}$ complexes that ubiquinate lysine residues on the IAA protein leading to degradation of the IAA protein and subsequent signal transduction. The deletion in the degron region reduces the length of the degron tail between Domains II and III by approximately 28 Å. This impairs the ability of the IAA protein to interact with the TIR1 protein, because it is no longer long enough to associate with sites on the TIR1 protein and keep the herbicide at its binding site. The result is that the IAA/herbicide/TIR1 complex dissociates faster and the IAA protein is ubiquitinated more slowly. Failure to ubiquitinate the IAA protein results in preventing the rapid increase in gene expression of 2,4-D regulated genes that is normal in the presence of 2,4-D. This model suggests that the deletion in the IAA2 gene would likely result in varying levels of resistance to any herbicide that binds to the IAA2/TIR1 complex. Our current data shows this includes 2,4-D, MCPA, and dicamba.

What is claimed is:

1. A method of producing a plant having tolerance to an herbicide, the method comprising:
   introducing a heterologous nucleic acid encoding an Aux/IAA polypeptide having a deleted or disrupted degron tail of domain II of the Aux/IAA protein into the plant, wherein the heterologous nucleic acid comprises a nucleotide sequence having at least 80% sequence identity to SEQ ID NO: 4 or encodes a polypeptide comprising an amino acid sequence having at least 80% sequence identity to SEQ ID NO: 3.

2. The method of claim 1, wherein the heterologous nucleic acid comprises a nucleotide sequence having at least 95% sequence identity to SEQ ID NO: 4 or encodes a polypeptide comprising an amino acid sequence having at least 95% sequence identity to SEQ ID NO: 3.

3. The method of claim 1, wherein said herbicide is a synthetic auxin herbicide.

4. The method of claim 3, wherein said herbicide is selected from 2,4-dichlorophenoxyacetic acid, dicamba, dichlorprop, clopyralid, fluroxypyr, florpyrauxifen-benzyl, and 2-methyl-4-chlorophenoxyacetic acid.

5. The method of claim 4, wherein said herbicide is 2,4-dichlorophenoxyacetic acid.

6. The method of claim 1, wherein said plant is a member of the Brassicaceae family.

7. The method of claim 1, wherein the heterologous nucleic acid comprises the nucleotide sequence set forth in SEQ ID NO: 4 or encodes a polypeptide comprising the amino acid sequence set forth in SEQ ID NO: 3.

* * * * *